United States Patent
Cushman et al.

(10) Patent No.: US 11,053,512 B2
(45) Date of Patent: Jul. 6, 2021

(54) METHODS OF ENGINEERED TISSUE SUCCULENCE IN PLANTS

(71) Applicant: BOARD OF REGENTS OF THE NEVADA SYSTEM OF HIGHER EDUCATION ON BEHALF OF THE UNIVERSITY OF NEVADA, Reno, NV (US)

(72) Inventors: John C. Cushman, Reno, NV (US); Sung Don Lim, Reno, NV (US)

(73) Assignee: BOARD OF REGENTS OF THE NEVADA SYSTEM OF HIGHER EDUCATION, ON BEHALF OF THE UNIVERSITY OF NEVADA, RENO, Reno, NV (US)

( * ) Notice: Subject to any disclaimer, the term of this patent is extended or adjusted under 35 U.S.C. 154(b) by 48 days.

(21) Appl. No.: 15/977,930

(22) Filed: May 11, 2018

(65) Prior Publication Data
US 2018/0327772 A1   Nov. 15, 2018

Related U.S. Application Data

(63) Continuation-in-part of application No. PCT/US2016/061677, filed on Nov. 11, 2016.

(60) Provisional application No. 62/255,158, filed on Nov. 13, 2015.

(51) Int. Cl.
*C12N 15/82*   (2006.01)
*C07K 14/415*   (2006.01)

(52) U.S. Cl.
CPC ........ *C12N 15/8273* (2013.01); *C07K 14/415* (2013.01); *C12N 15/8201* (2013.01); *C12N 15/8225* (2013.01); *C12N 15/8226* (2013.01); *C12N 15/8234* (2013.01); *C12N 15/8279* (2013.01); *C12N 15/8294* (2013.01)

(58) Field of Classification Search
None
See application file for complete search history.

(56) References Cited

U.S. PATENT DOCUMENTS 8,224,578 B2 * 7/2012 Raab ............... C07K 14/535 702/19
8,962,921 B2   2/2015 Christensen et al.

FOREIGN PATENT DOCUMENTS

EP   2324703 B1   5/2015
WO   2015069557 A2   5/2015

OTHER PUBLICATIONS

Sequence Accession JQ823168, Mar. 14, 2013 (sequence alignment is attached in the office action) (Year: 2013).*
Nicolas et al, J Exp. Bot., 64 (4): 991-1003, 2013 (Year: 2013).*
NCBI, GenBank accession No. JQ823168.1, Mar. 14, 2013, Whole Document.
Borland et al., "Engineering crassulacean acid metabolism to improve water-use efficiency" Trends in Plant Science, vol. 19, No. 5, pp. 327-338; May 2014.
Lim et al., "Engineering tissue succulence to improve water-use efficiency of bioenergy feedstocks", In:Genomic Science Contractors-Grantees meeting XIV and USDA-DOE Plant Feedstock Genomics for Bioenergy meeting, Mar. 6-9, 2016, Whole document.

* cited by examiner

*Primary Examiner* — Elizabeth F McElwain
(74) *Attorney, Agent, or Firm* — Schwabe, Williamson & Wyatt, P.C.

(57) ABSTRACT

Disclosed herein are methods of altering tissue succulence in plants. In some examples, a disclosed method includes overexpressing a modified helix-loop-helix transcription factor CEB1 in a plant cell, thereby altering plant succulence. The disclosed methods can be used to improve the drought and salinity tolerance of plants, such as in plants in arid or saline environments, and also enhance the ability of plants to perform. Also disclosed are CEB1 nucleic acids and transgenic plants containing such nucleic acids.

15 Claims, 77 Drawing Sheets
Specification includes a Sequence Listing.

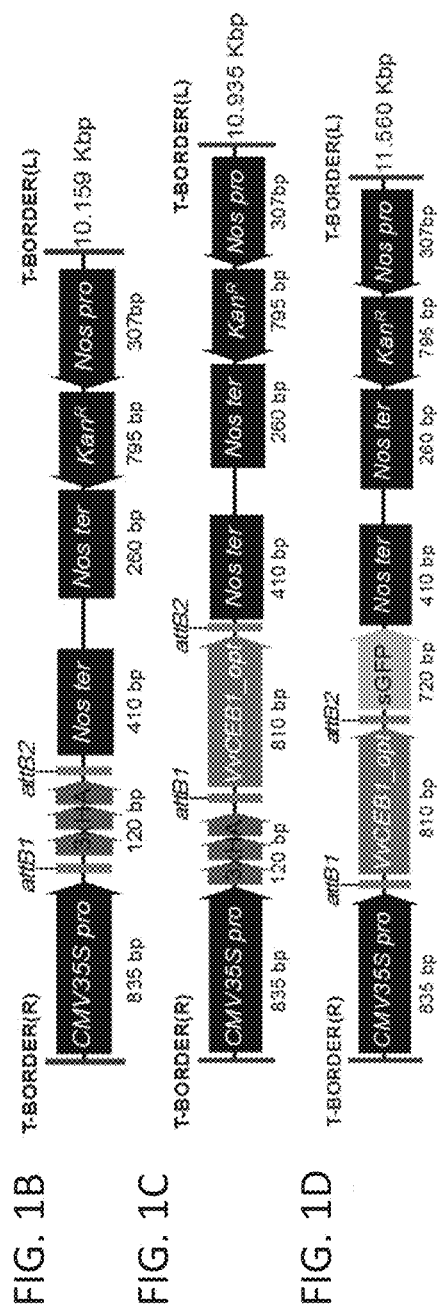
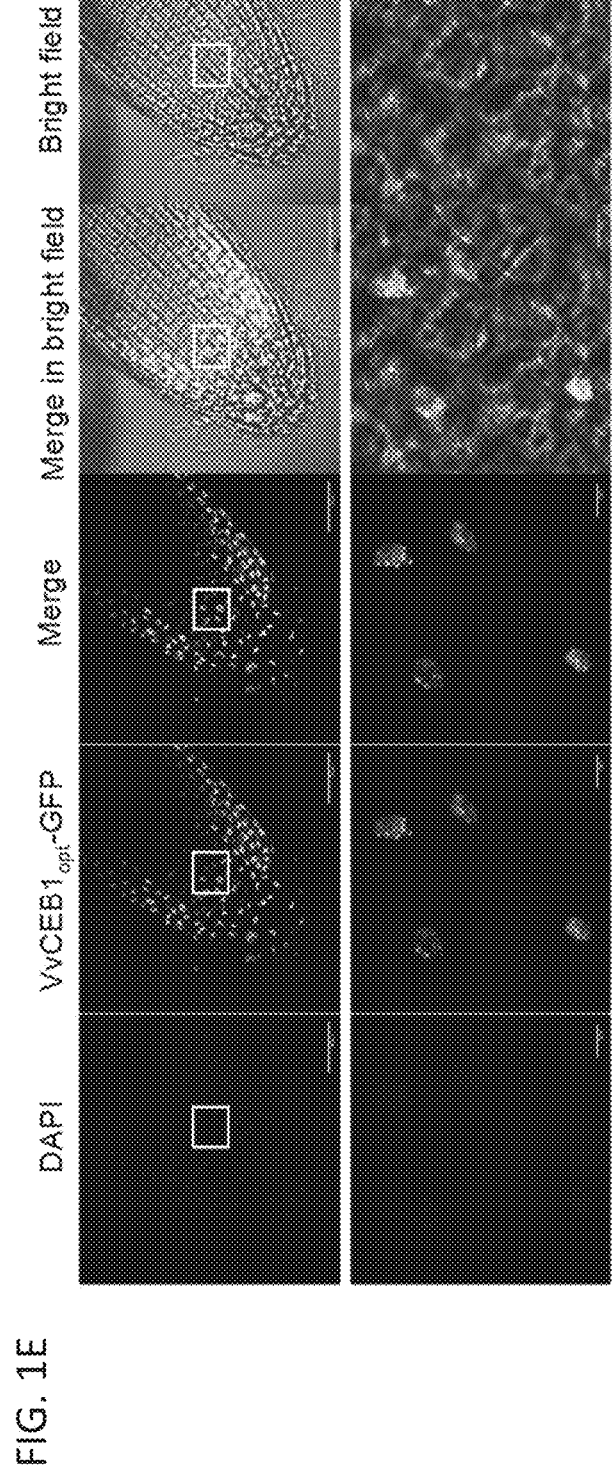
FIG. 1B
FIG. 1C
FIG. 1D
FIG. 1E 2-week-old

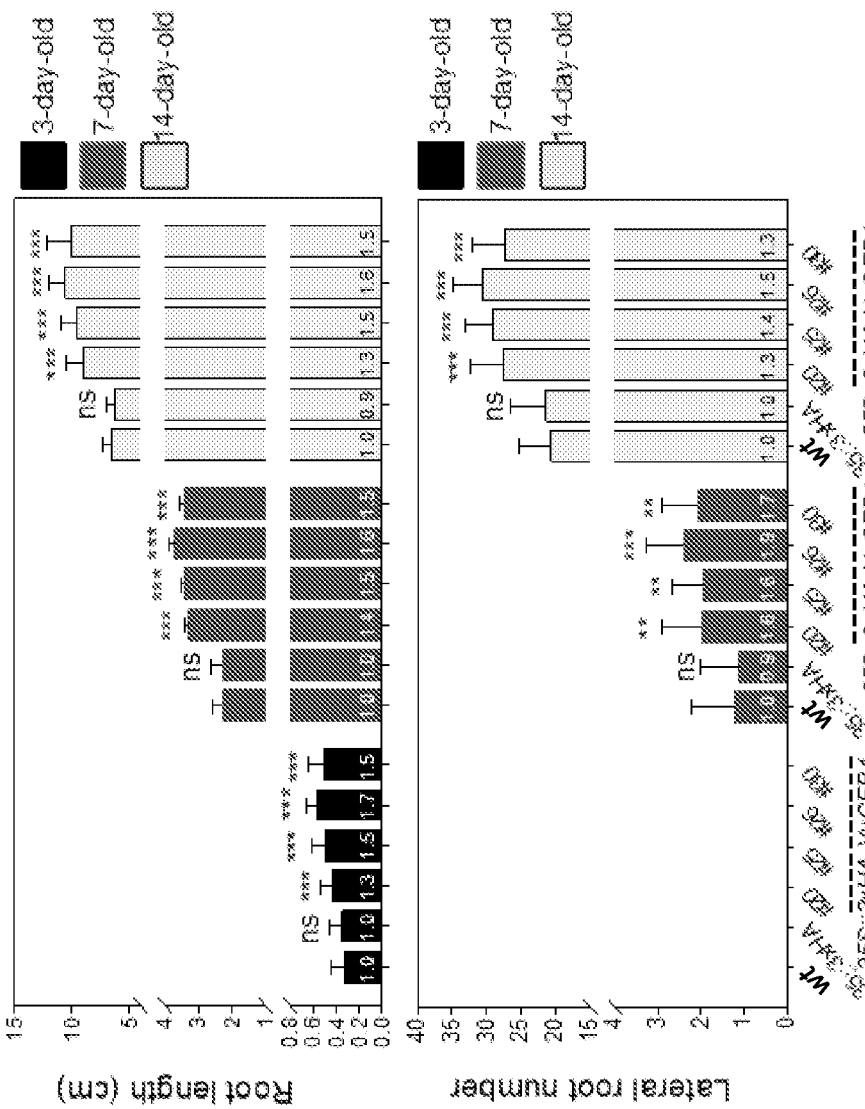
FIG. 8B
FIG. 8C
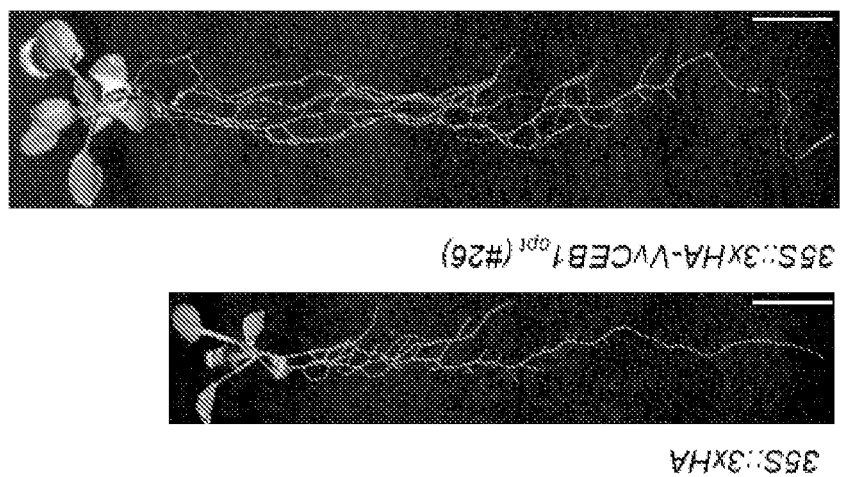
FIG. 8A 3-week-old

35S::3xHA

35S::3xHA-
VvCEB1$_{opt}$ (#26)

35S::3xHA            35S::3xHA-VvCEB1$^{opt}$ (#26)

*35S::3xHA*

*35S::3xHA-VvCEB1$_{opt}$ (#26)*

9 days after 500mM NaCl treatment

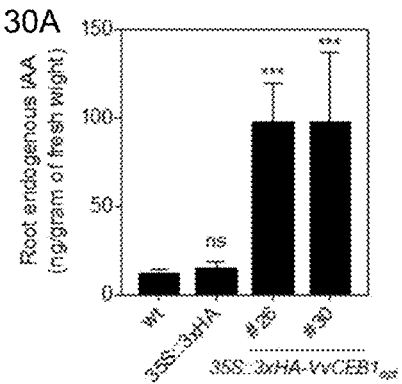
FIG. 30A
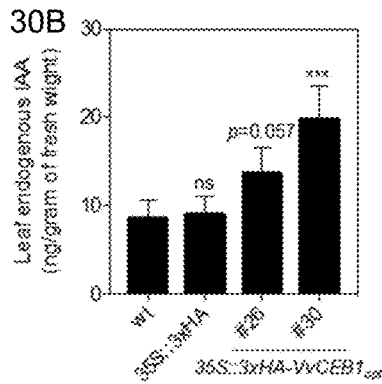
FIG. 30B
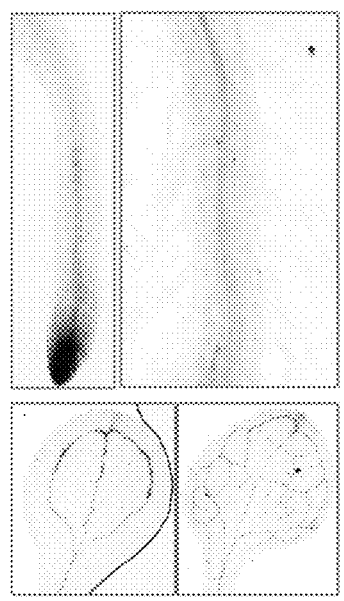
FIG. 30C  *DR5rev::GUS* EV Background
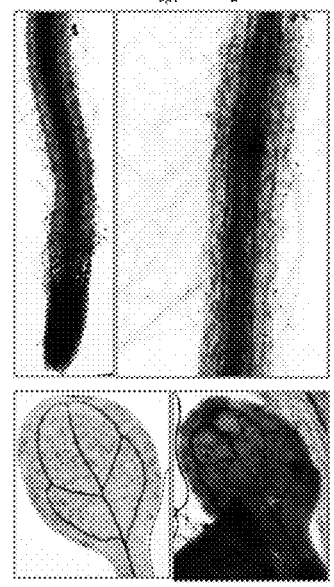
FIG. 30D  *DR5rev::GUS* Ox-VvCEB1$_{opt}$ Background
FIGS. 30A-30D

FIG. 31A
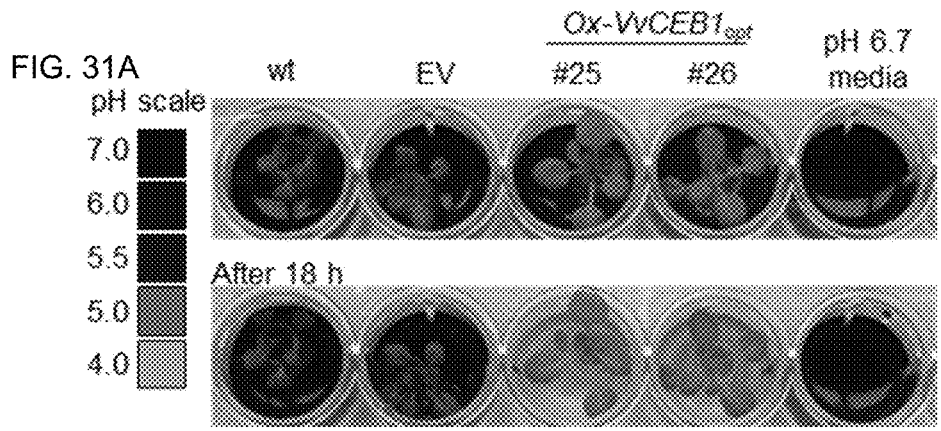
FIG. 31B
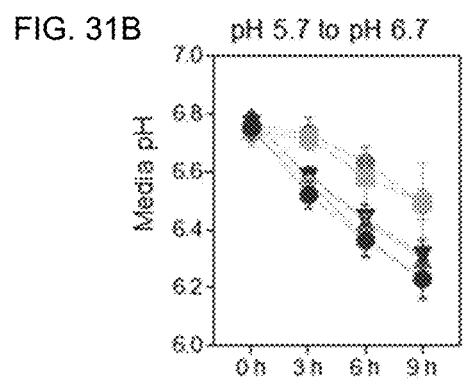
FIG. 31C
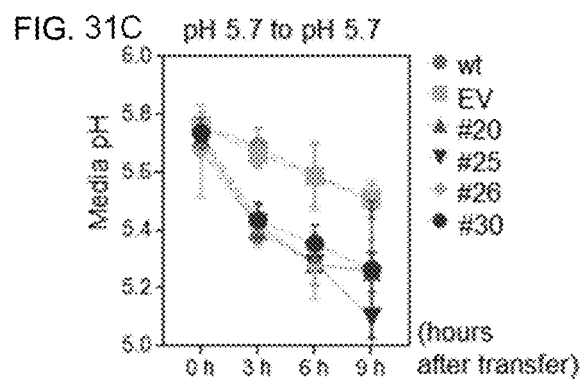
FIG. 31D
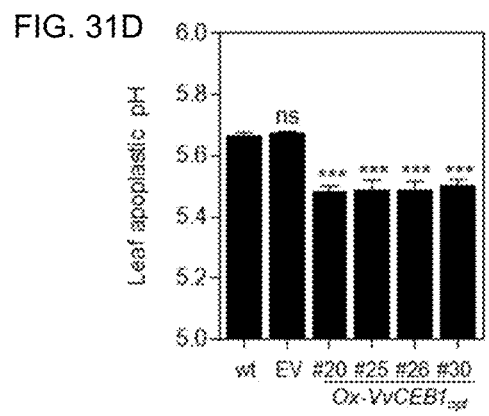
FIGS. 31A-31D

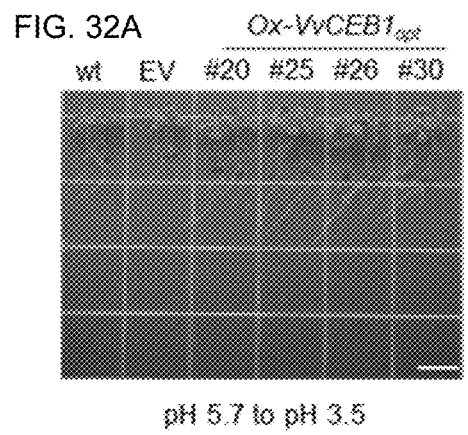
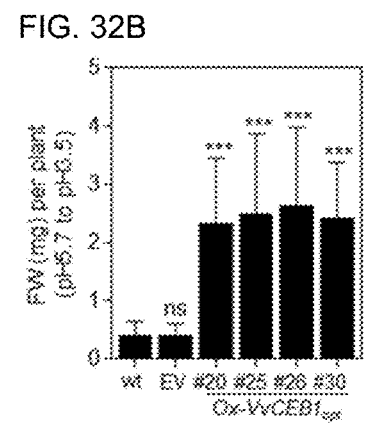
FIG. 32A Ox-VvCEB1_opt
pH 5.7 to pH 3.5
FIG. 32B
FIGS. 32A and 32B

FIGS. 33A-33C

FIG. 34A
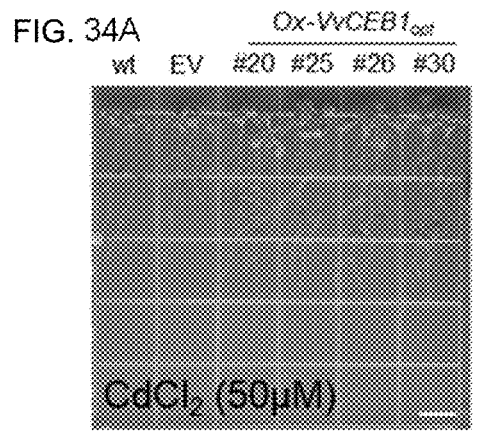
FIG. 34B
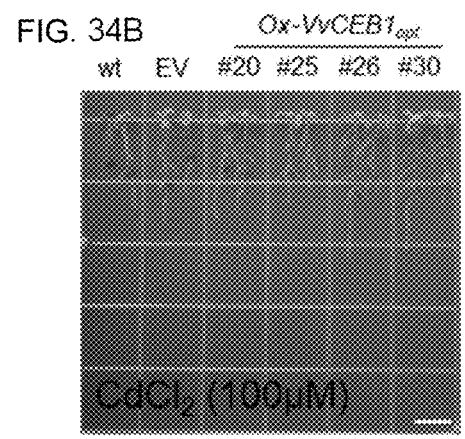
FIG. 34C
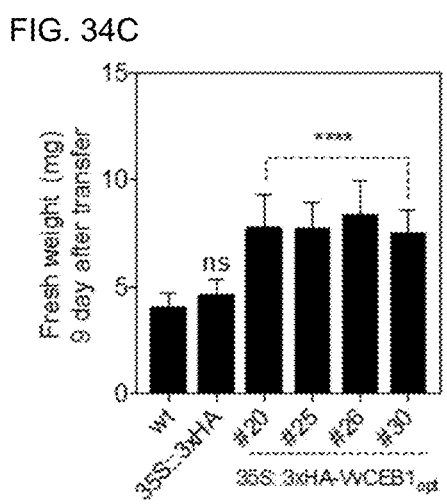
FIG. 34D
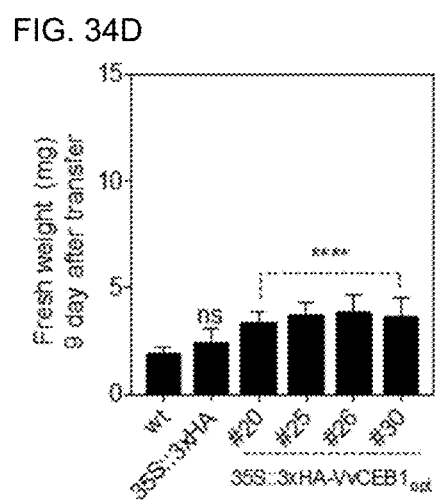
FIGS. 34A-34D

FIGS. 35A-35F

FIG. 36A
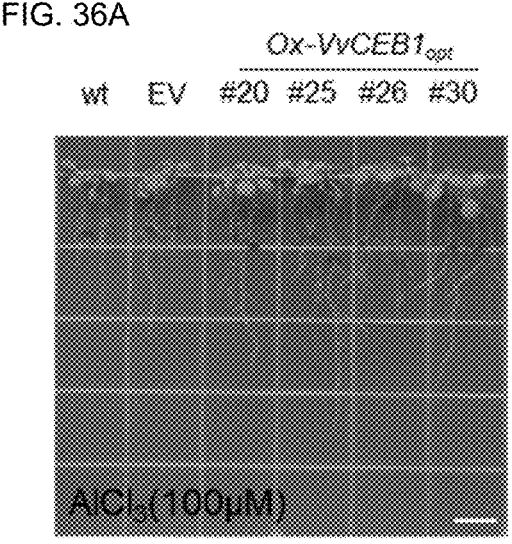
FIG. 36B
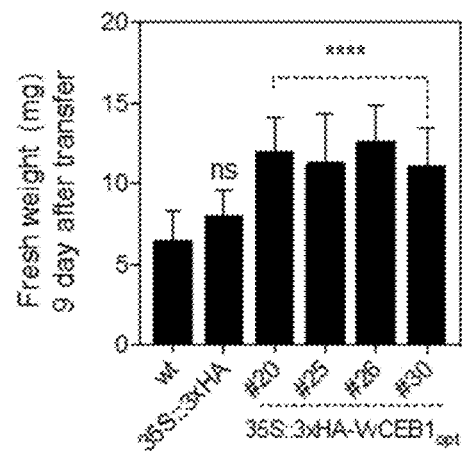
FIGS. 36A and 36B

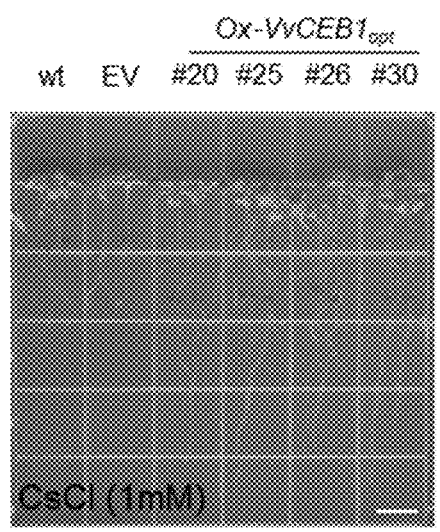 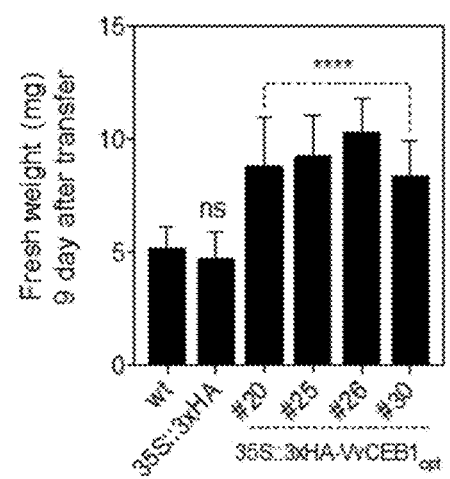
FIG. 37A  FIG. 37B
FIGS. 37A and 37B

FIG. 38A
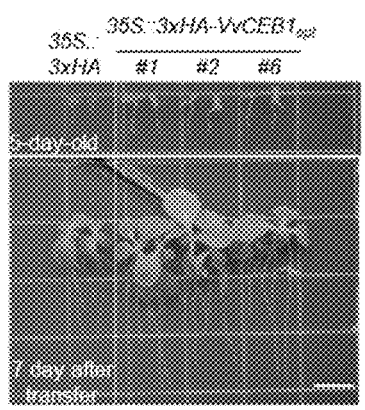
FIG. 38B
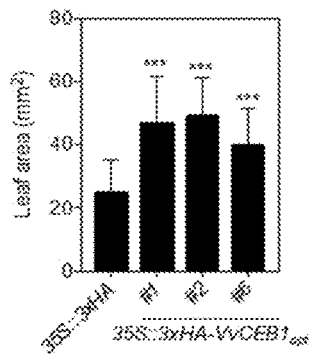
FIG. 38C
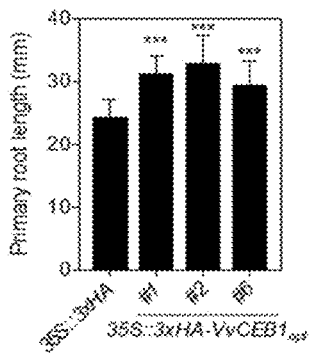
FIG. 38D
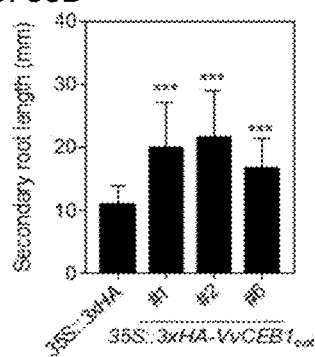
FIG. 38E
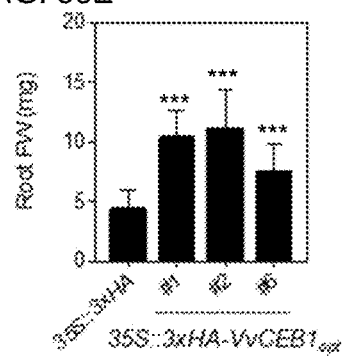
FIG. 38F
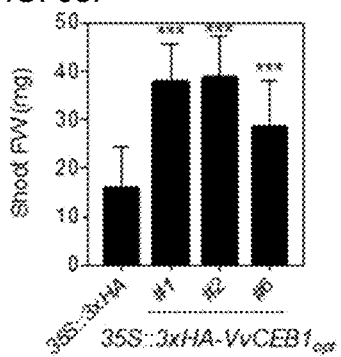
FIGS. 38A-38F FIG. 39A
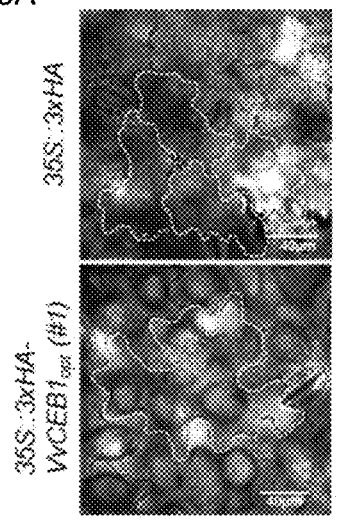
FIG. 39B
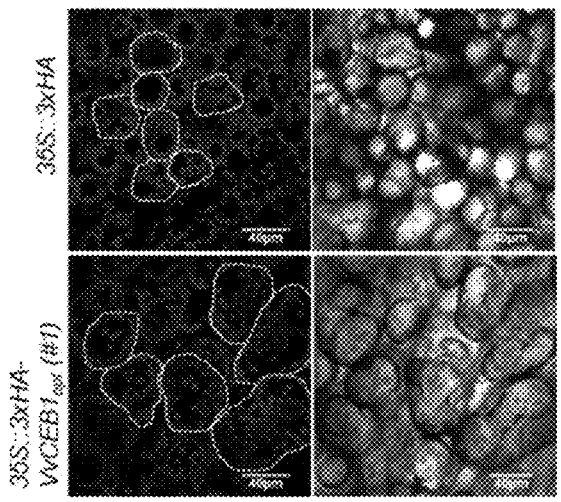
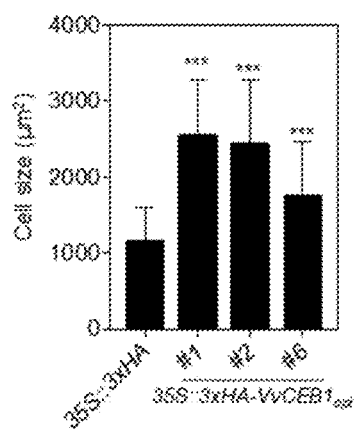
FIG. 39C
FIGS. 39A-39C FIG. 40A
FIG. 40B
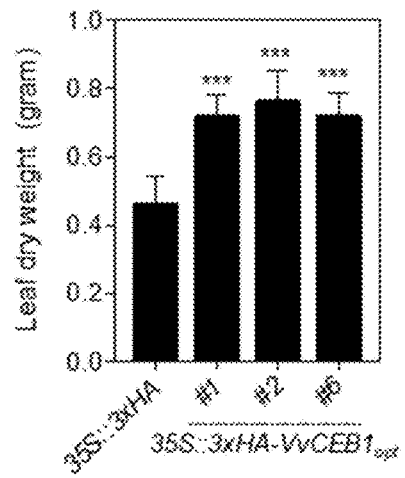
FIGS. 40A and 40B FIG. 43A
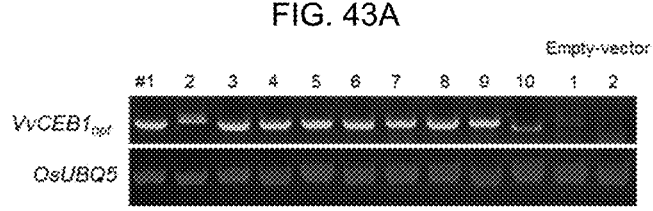
FIG. 43C
FIG. 43B
FIGS. 43A-43C

METHODS OF ENGINEERED TISSUE SUCCULENCE IN PLANTS

CROSS REFERENCE TO RELATED APPLICATION

This application is a continuation-in-part of International Application PCT/US2016/061677, filed Nov. 11, 2016, which claims the priority benefit of the earlier filing date of U.S. Provisional Application No. 62/255,158, filed Nov. 13, 2015, each disclosure of which is hereby incorporated herein by reference in its entirety.

ACKNOWLEDGMENT OF GOVERNMENT SUPPORT

This invention was made with government support under grant no. DE-SC0008834 awarded by the United States Department of Energy. The government has certain rights in the invention.

FIELD

This disclosure relates to the field of plant molecular biology and genetic engineering and specifically to methods of modulating tissue succulence in plants.

BACKGROUND

There is a pressing need to increase global food production world-wide and to improve plant water-use efficiency and drought tolerance. Global climate change is predicted to increase heat, drought, and soil-drying conditions, and thereby increase crop sensitivity to water vapor pressure deficit, resulting in productivity losses. Increasing competition between agricultural freshwater use and municipal or industrial uses suggest that crops with greater heat and drought durability and greater water-use efficiency will be crucial for sustainable biomass production systems in the future. Thus, there is an on-going need to identify genetic mechanisms and factors involved in regulating drought tolerance and overall plant health.

SUMMARY

Disclosed herein are methods of altering plant succulence. In some embodiments, a disclosed method comprises overexpressing a modified basic helix-loop-helix transcription factor (bHLH) protein (CEB1), such as from *Vitis vinifera* (wine grape) (for example VvCEB1), in a plant cell, thereby altering plant succulence. The disclosed methods can be used to improve the ability of plants to attenuate, resist, or tolerate drought, such as in plants in arid environments, to tolerate salinity stress, such as plants in saline environments, enhance the ability of plants to accumulate vegetative biomass, and improve overall reproductive capacity reflected in increased seed production. In some examples, a disclosed method is used to increase plant cell size, increase leaf size, increase leaf number, increase leaf biomass, reduce hypocotyl length, increase hypocotyl width, increase plant inflorescence width, increase plant inflorescence height, increase plant inflorescence stem thickness, increase plant root size, increase plant root length, increase plant root branching, increase plant root biomass, increase plant tissue succulence, increase plant water content, increase leaf chlorophyll content, increase leaf protein content, increase leaf soluble sugar content, increase plant flower size, increase plant floral organ size, increase plant inflorescence number, increase plant silique number, increase plant silique size, increase fruit size, increase fruit number, increase plant seed size, increase plant seed area, increase plant seed mass, increase plant seed number, increase total plant seed production, or any combination thereof. In some examples, the method is used to generate a plant with improved drought tolerance. In some examples, the method is used to delay plant flowering time, such as by day, a week or up to two weeks. In some examples, the method is used to delay leaf senescence, such as by a day, a week or up to four weeks. In other examples, the method is used to stimulate plant flowering. In some examples, the method is used to reduce intracellular air space with the resulting plant becoming an anatomically optimized host for performance of (engineered) Crassulacean acid metabolism (CAM). In some examples, the method is used to increase plant tolerance to salinity and related salts that impose an ionic stress. In some examples, the methods are used to increase plant tolerance to osmotic stress, such as to mannitol or polyethylene glycol (PEG), and related osmotic agents that impose an osmotic stress.

In some examples, a method to stimulate increase leaf auxin content and auxin-related leaf shape, such an increasing leaf teeth number, and leaf margin serrations is disclosed. In some examples, a method to improve plant water-use efficiency is provided. In some examples, a method to reduce leaf stomatal aperture and/or reduce leaf stomatal density is disclosed. In some examples, a method to reduce leaf intracellular air space with the resulting plant becoming an anatomically optimized host for the performance of (engineered) $C_4$ photosynthesis and CAM is provided. In some examples, a method of increased plant tolerance to acute and survival under chronic salinity stress (such as to NaCl and other salts) that imposes an ionic stress is disclosed. In some examples, a method of increased plant tolerance to acute water-deficit (drought) stress imposed by a lack of water availability is disclosed. In some examples, a method of increased plant tolerance to chronic water-deficit (drought) stress imposed by a lack of water availability is disclosed. In some examples, a method of attenuating plant leaf water loss is provided.

Also disclosed are isolated polynucleotide sequences, such as a codon-optimized, synthetic version of the CEB genes or functionally related gene orthologues from one of the following species: *Vitis vinifera*(vV, wine grape, Cabernet sauvignon), *Prunus persica* (peach), *Citrus senensis* (sweet orange), *Theobroma cacao* (Cacao), *Fragaria vesca* (strawberry) or *Ananas cosmosus* (pineapple). In some examples, the isolated polynucleotide sequence is a codon-optimized synthetic version of VvCeb1gene such as a VvCeb1gene. In some examples, an isolated polynucleotide sequence comprises a plant promoter and a disclosed codon-optimized polynucleotide sequence. In some examples, plant transformation vectors comprising a disclosed isolated polynucleotide sequence are also provided. Moreover, transgenic plant cells, plant part, and plants comprising a disclosed vector construct are provided.

The foregoing and other features and advantages of the disclosure will become more apparent from the following detailed description, which proceeds with reference to the accompanying figures.

BRIEF DESCRIPTION OF THE DRAWINGS

FIGS. 1B-1D provide schematic representations of binary vector constructs used for transformation of *Arabidopsis thaliana*. (FIG. 1B) The codon-optimized sequence of VvCeb1 was synthesized and cloned into the ImpGWB415 vector containing the CaMV 35S promoter for transformation of *Arabidopsis*. (FIG. 1C) The synthesized 3×HA tag was cloned into the ImpGWB402 vector and transformed into *Arabidopsis* for the 35S::3×HA empty-vector control. (FIG. 1D) The VvCeb1$_{opt}$fragment was cloned into the ImpGWB405 vector containing the CaMV 35Spromoter and C-terminal synthetic green fluorescent protein (sGFP) to study subcellular localization. Kanamycin (KanR) was used as the selectable marker. T-border (R) and T-border (L) indicate T-DNA right border and T-DNA left borders, respectively.

FIG. 1E provides images illustrating nuclear localization of the VvCEB1 opt-sGFP fusion protein in *A. thaliana*. The 35S::VvCEB1opt-sGFP construct was transformed into *Arabidopsis*. Seven-day-old seedlings (T1) were used to analyze subcellular localization. Images in the lower panel correspond to magnification of the regions indicated by the white squares in the upper panel. Scale bars, 40 μm (top panels) and 5 μm (bottom panels). In summary, the VvCEB1 opt-sGFP fusion protein was strongly expressed and localized to the nucleus in *Arabidopsis*.

(FIGS. 29A to 29G) Concentrations of inorganic ions in wild-type (WT), 35S::3×HA empty-vector control line (EV), and VvCEB1$_{opt}$-overexpressing lines (#20, #25, #26, and #30). Calcium (FIG. 29A), Potassium (FIG. 29B), Sulfur (FIG. 29C), Phosphorus (FIG. 29D), Molybdenum (FIG. 29E), Sodium (FIG. 29F), and Chloride (FIG. 29G) content on a dry weight basis (n=6). Values represent means±s.d., ns=non-significant, *p<0.05, p<0.01, and *p<0.001, one-way ANOVA with Dunnett's multiple comparison test.

FIGS. 30A-30D illustrate VvCEB1$_{opt}$ overexpression increased auxin accumulation in *Arabidopsis*. (FIGS. 30A and 30B) Indole-3-acetic acid (IAA) content was determined in roots (FIG. 30A) and leaves (FIG. 30B) of wild-type (wt), 35S::3×HA empty-vector control line (EV), and VvCEB1$_{opt}$-overexpressing lines (#25 and #26) (n=5)). Values represent means±s.d., ns=non-significant, ***p<0.001, one-way ANOVA with Dunnett's multiple comparison test. (FIG. 30C) Expression of DR5rev::GUS in 35S::3×HA empty-vector (EV) line in root tip, mature root region and root hairs, cotyledon, and 1st leaf tissues of 10-day-old seedlings. (FIG. 30D) Expression of DR5rev::GUS in Ox-VvCEB1$_{opt}$ line (#26) (FIG. 30D) root tip, mature root region and root hairs, cotyledon, and 1st leaf tissues of 10-day-old seedlings.

FIGS. 31A-31D illustrate VvCEB1$_{opt}$ overexpression increased plasma membrane-localized proton pumps (PM-H+-ATPase) activity in *Arabidopsis*. (FIG. 31A) pH=6.7 media acidification by transferred 10-day-old wild-type (wt) plants, 35S::3×HA empty-vector control line (EV), and VvCEB1$_{opt}$-overexpressing lines (#25 and #26). (FIGS. 31B and 31C) Time course of media acidification by roots of transferred 10-day-old wild-type (wt) plants, 35S::3×HA empty-vector control line (EV), and VvCEB1$_{opt}$-overexpressing lines (#20, #25, #26, and #30) to near neutral (FIG. 31B) and standard (FIG. 31C) media. n=4 biological replicates. (FIG. 31D) Leaf apoplastic pH. n=3 biological replicates. Values represent means±s.d., ns=non-significant, ***p<0.001, one-way ANOVA with Dunnett's multiple comparison test.

FIGS. 32A-32B illustrate VvCEB1$_{opt}$ overexpression reduces low-pH sensitivity in *Arabidopsis*. (FIG. 32A) Representative seedlings of wild-type (wt) plants, 35S:: 3×HA empty-vector control line (EV), and VvCEB1$_{opt}$-overexpressing lines (#20, #25, #26, and #30) plants transferred from normal (pH=5.7) media to acidic media (pH=3.5) at 3 days after germination. Image was taken 9 days after transfer. (FIG. 32B) Quantification of fresh weight (FW) at 9 days after transfer (n=20). Values represent means±s.d., ns=non-significant, ***p<0.001, one-way ANOVA with Dunnett's multiple comparison test. Bar=1 cm (FIG. 33A) Representative seedlings of wild-type (wt) plants, 35S:: 3×HA empty-vector control line (EV), and VvCEB1$_{opt}$-overexpressing lines (#20, #25, #26, and #30) plants transferred from normal (pH=5.7) media to media containing 15 mg of hygromycin B (pH=5.7) at 3 day after germination. Image was taken 9 days after transfer. (FIG. 33B) Quantification of fresh weight (FW) grown in the presence of hygromycin B (15 mg per liter) at 9 days after transfer (n=20). (FIG. 33C) Quantification of fresh weight (FW) grown in the presence of hygromycin B (50 mg per liter) at 9 days after transfer (n=20). Values represent means±s.d., ns=non-significant, ***p<0.001, one-way ANOVA with Dunnett's multiple comparison test. Bar=1 cm FIGS. 34A-34D illustrate VvCEB1$_{opt}$ overexpression increases cadmium tolerance in *Arabidopsis*. (FIGS. 34A-34B) Representative seedlings of wild-type (wt) plants, 35S:: 3×HA empty-vector control line (EV), and VvCEB1$_{opt}$-overexpressing lines (#20, #25, #26, and #30) plants transferred from normal (pH=5.7) media to media containing 50 µM (FIG. 34A) or 100 µM (FIG. 34B) of CdCl$_2$ at 3 day after germination. Image was taken 9 days after transfer. (FIG. 34C) Quantification of fresh weight (FW) grown in the presence of CdCl$_2$ (50 µM) at 9 days after transfer (n=20). (FIG. 34D) Quantification of fresh weight (FW) grown in the presence of CdCl$_2$ (100 µM) at 9 days after transfer (n=20). Values represent means±s.d., ns=non-significant, ***p<0.001, one-way ANOVA with Dunnett's multiple comparison test. Bar=1 cm (FIGS. 35A to 35C) Representative seedlings of wild-type (wt) plants, 35S:: 3×HA empty-vector control line (EV), and VvCEB1$_{opt}$-overexpressing lines (#20, #25, #26, and #30) plants transferred from normal media to media containing 100 µM (FIG. 35A), 150 µM (FIG. 35B), 200 µM (FIG. 35C) of As$_2$O$_5$ at 3 day after germination. Image was taken 9 days after transfer. (FIG. 35D) Quantification of fresh weight (FW) grown in the presence of As$_2$O$_5$ (100 µM) at 9 days after transfer (n=20). (FIG. 35E) Quantification of fresh weight (FW) grown in the presence of As$_2$O$_5$ (150 µM) at 9 days after transfer (n=20). (FIG. 35F) Quantification of fresh weight (FW) grown in the presence of As$_2$O$_5$ (200 µM) at 9 days after transfer (n=20). Values represent means±s.d., ns=non-significant, ***p<0.001, one-way ANOVA with Dunnett's multiple comparison test. Bar=1 cm FIGS. 36A-36B illustrate VvCEB1$_{opt}$ overexpression increased aluminum tolerance in *Arabidopsis*. (FIG. 36A) Representative seedlings of wild-type (wt) plants, 35S:: 3×HA empty-vector control line (EV), and VvCEB1$_{opt}$-overexpressing lines (#20, #25, #26, and #30) plants transferred from normal media to media containing 100 µM of AlCl$_3$ at 3 day after germination. Image was taken 9 days after transfer. (FIG. 36B) Quantification of fresh weight (FW) grown in the presence of AlCl$_3$ (100 µM) at 9 days after transfer (n=20). Values represent means±s.d., ns=non-significant, ***p<0.001, one-way ANOVA with Dunnett's multiple comparison test. Bar=1 cm FIGS. 37A-37B illustrate VvCEB1$_{opt}$ overexpression increased cesium tolerance in *Arabidopsis*. (FIG. 37A) Representative seedlings of wild-type (wt), 35S:: 3×HA empty-vector control line (EV), and VvCEB1$_{opt}$-overexpressing lines (#20, #25, #26, and #30) plants transferred from normal media to media containing 1 mM of CsCl at 3 day after germination. Image was taken 9 days after transfer. (FIG. 37B) Quantification of fresh weight (FW) grown in the presence of CsCl (1 mM) at 9 days after transfer (n=20). Values represent means±s.d., ns=non-significant, ***p<0.001, one-way ANOVA with Dunnett's multiple comparison test. Bar=1 cm FIGS. 38A-38F illustrate VvCEB1$_{opt}$ overexpression increased overall plant size in *Nicotiana sylvestris* (flowering tobacco). (FIG. 38A) Representative seedlings of wild-type (wt), 35S:: 3×HA empty-vector control line (EV), and VvCEB1$_{opt}$-overexpressing (#1, #2, and #6) transgenic tobacco plants. Seeds (T1) were grown for 5 days on half-strength MS medium containing kanamycin (200 mg/L) and transferred to kanamycin-free half-strength MS medium (top panel) and grown for 7 days (lower panel). Bar=1 cm. (FIG. 38B) Quantification of the 1st leaf area (n=40). (FIG. 38C) Quantification of primary root length (n=40). (FIG. 38D) Quantification of the secondary root length (n=40). (FIG. 38E) Quantification of the root fresh weight (FW) (n=30). (FIG. 38F) Quantification of the shoot fresh weight (n=30). Values represent means±s.d., ns=non-significant, ***p<0.001, one-way ANOVA with Dunnett's multiple comparison test.

FIGS. 39A-39C illustrate VvCEB1$_{opt}$ overexpression increased cell size in *Nicotiana sylvestris* (flowering tobacco). (FIG. 39A) Lower epidermis cell(s) of the EV and the VvCEB1$_{opt}$-overexpressing lines. White dotted lines indicate the shape of cells. (FIG. 39B) Palisade mesophyll cell(s) and chlorophyll autofluorescence of the EV and the VvCEB1opt-overexpressing lines. White dotted lines indicate the shape of cells. (FIG. 39C) Quantification of the palisade mesophyll cell size (n=60). Values represent means±s.d., ns=non-significant, ***p<0.001, one-way ANOVA with Dunnett's multiple comparison test.

FIGS. 40A-40B illustrate VvCEB1$_{opt}$ overexpression increased leaf biomass in *Nicotiana sylvestris* (flowering tobacco). (FIG. 40A) Representative dry leaves of 35S:: 3×HA empty-vector control line (EV), and VvCEB1$_{opt}$-overexpressing (#1, #2, and #6) transgenic tobacco plants. Seeds (T1) were grown for 5 days on half-strength MS medium containing kanamycin (200 mg/L) and transferred to soil and grown for 3 month (lower panel). Bar=5 cm. (FIG. 40B) Quantification of leaf dry weight (n=20). Values represent means±s.d., ns=non-significant, ***p<0.001, one-way ANOVA with Dunnett's multiple comparison test.

(FIG. 41A) Representative plant size of 35S:: 3×HA empty-vector control line (EV), and VvCEB1$_{opt}$-overexpressing (#1) transgenic tobacco plants. Seeds (T1) were grown for 5 days on half-strength MS medium containing kanamycin (200 mg/L) and transferred to soil and grown for 3 month. Bar=10 cm. (FIG. 41B) Quantification of plant height (n=10). (FIG. 41C) Quantification of seed yield (n>7). Values represent means±s.d., ns=non-significant, p<0.01, *p<0.001, one-way ANOVA with Dunnett's multiple comparison test.

(FIG. 42A) Representative seed size of wild-type (WT) plants, empty-vector control line (EV), and VvCEB1$_{opt}$-expressing transgenic *Camelina* seeds. Seeds (T0) were grown for 10 days on half-strength MS medium containing hygromycin (25 mg/L) and transferred to soil and seeds were harvested. Bar=1 mm. (FIG. 42B) Quantification of seed area (n>44). (FIG. 42C) Quantification of 100-seed weight (n=4). Values represent means±s.d., ns=non-significant, ***p<0.001, one-way ANOVA with Dunnett's multiple comparison test.

FIGS. 43A-43C illustrate VvCEB1$_{opt}$ overexpression increased overall plant size in *Oryza sativa* (cv. dongjin). (FIG. 43A) Semi-quantitative RT-PCR was used to select transgenic VvCEB1$_{opt}$ transgenic plants. OsUBQ5 was used as internal control. (FIGS. 43B and 43C) Seeds (T1) were grown for 10 days on full-strength MS medium containing hygromycin (25 mg/L) and transferred to the field to harvest T2 seeds. Representative field images of 3-month-old (FIG. 43B) and 5-month-old (FIG. 43C) wild-type (WT), empty-vector control line (EV), and VvCEB1$_{opt}$ overexpressing transgenic rice plant.

SEQUENCE LISTING

Figure 1A:
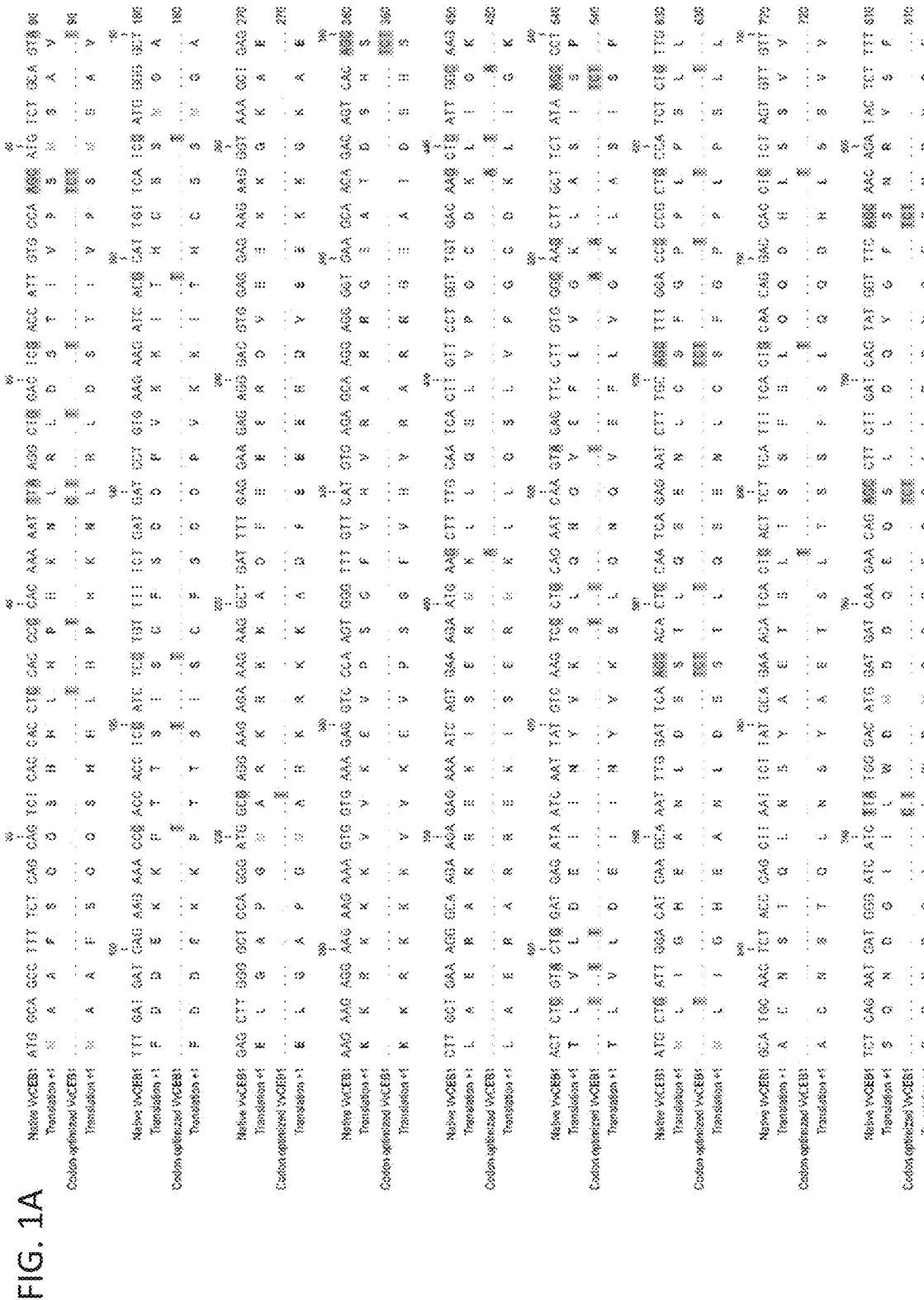
FIG. 1A is a schematic of a native sequence of a basic helix-loop-helix transcription factor (VvCeb1; SEQ ID NO: 1) showing codon optimization corresponding to SEQ ID NO: 3. Highlights in the codon optimized VvCeb1 indicate the modified nucleotides. The resulting amino acid sequence is set forth as SEQ ID NO: 2, which is duplicated to show that the codon optimization did not alter the resulting amino acid sequence. In summary, rare codons of native VvCeb1, which are those with a frequency of less than 15% per thousand codons, were altered to more closely match *Arabidopsis* and *Populus* codon usage. A total of 56 nucleotides (6.9%) out of the 810 nucleotides of VvCEB1 were altered for ectopic overexpression.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt", which is incorporated by reference herein. In the accompanying sequence listing:

SEQ ID NO: 1 is the nucleic acid sequence of native VvCEB1;

SEQ ID NO: 2 is the amino acid sequence of codon optimized VvCEB1; and

SEQ ID NOs: 3-9 are exemplary codon optimized nucleic acid sequences of CEB1.

DETAILED DESCRIPTION

I. Introduction

Tissue succulence is present in about 4% of vascular plant species and is an important plant trait that improves the drought attenuation of plants in arid environments. Tissue succulence also enhances the ability of plants to perform crassulacean acid metabolism (CAM), a specialized form of photosynthesis found in about 6% of vascular plant species. Tissue succulence also serves as an anatomical corequisite in the optimal performance of CAM as the succulent tissue serves to help limit the diffusion of $CO_2$ out of the leaf upon its release within the leaf during the day so that it may be refixed by ribulose 1,5-bisphosphate carboxylase oxygenase. Disclosed herein is the surprising finding that overexpression of a modified basic helix-loop-helix transcription factor CEB1, such as CEB1 from wine grape (VvCEB1), can regulate tissue succulence. In particular, increased tissue succulence from overexpression of a modified VvCEB1 was found to result in up to a 4.2-fold increase plant leaf fresh weight, a 2.4-fold increase in leaf dry weight, up to a 1.4-fold increase in root fresh weight, a 2.1-fold increase in root dry weight, up to a 1.5-fold increase in flower size, and up to a 3-fold increase in seed biomass production. The increased size of these organs also resulted in up to a 1.7-fold increase in leaf thickness, up to a 1.8-fold increase in leaf succulence, and up to a 0.3-fold reduction in intracellular air space (IAS). This reduction in IAS is a feature of the innovation because it limits $CO_2$ diffusion out of the leaf and plays a role in recapture of photorespiratory $CO_2$ loss and $CO_2$ recapture by CAM during the day. The engineered succulent plants displayed greater tolerance to water-deficit stress and greater regrowth following acute water-deficit stress likely due to the ability of the plant to retain and store water within its vegetative tissues. The disclosed methods also have the added agronomic benefit of increasing seed production in crop plants.

Moreover, the transgenic plants had shorter and thicker hypocotyls and floral bolts than wild type plants, which may reduce lodging. In addition, the transgenic plants were more salt tolerant able to grow under 200 to 300 mM NaCl compared to wild type or empty vector control plants; more tolerant to osmotic stresses and were able to grow under increased concentrations of mannitol (400 to 500 mM) and polyethylene glycol (PEG) 8000 (−0.5 to −0.7 MPa); and insensitive to abscisic acid (ABA) at up to 5 µm. Despite having a larger leaf surface area, when grown in soil, the transgenic plants were more tolerant to water-deficit (drought) stress and are able to retain tissue water holding capacity relative to wild type plants. Lastly, the increase cell size did not appear to be associated with an increase in ploidy level of the plants.

Based upon these findings, disclosed herein are methods for the genetic engineering of tissue succulence. The disclosed methods generate a fundamental and global change to plant cell architecture and anatomy resulting in larger cells of all types, which in turn results in greater plant productivity and yield, while also conferring improved drought and salinity tolerance. Furthermore, the disclosed methods resulted in reduced stomatal density and reduced stomatal aperture, which conferred improvement in both instantaneous and integrated water-use efficiency to the plant. It is contemplated that the disclosed methods have broad applicability to many crops including those where increased productivity and drought and salinity tolerance is desired. The disclosed methods benefit the agribusiness sector by improving crop yields while at the same time improving drought and salinity tolerance. In particular, this innovation confers value to agribusiness sector through increased crop yields in terms of both vegetative biomass and seed yields, while also conferring improved drought and salinity tolerance.

II. Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants and reference to "the seed" includes reference to one or more seeds and equivalents thereof known to those skilled in the art, and so forth. The term "or" refers to a single element of stated alternative elements or a combination of two or more elements, unless the context clearly indicates otherwise. For example, the phrase "A or B" refers to A, B, or a combination of both A and B.

Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference. Definitions of common terms in molecular biology may be found in Benjamin Lewin Genes V published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; Harlow and Lane, *Using Antibodies: A Laboratory Manual*, Cold Spring Harbor Laboratory Press, 1999; and Kieser, T., Bibb, M. J., Buttner, M. J., Chater, K. F., and Hopwood, D. A.: Practical *Streptomyces* genetics, John Innes Centre, Norwich Research Park, Colney, Norwich NR4 &UH, England, 2000.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

To facilitate review of the various embodiments of this disclosure, the following explanations of specific terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of a linked gene, are generally located 5' or upstream of the coding region. However, enhancer elements can exert their effect even when located 3' of the promoter element and the coding region. Transcription termination and polyadenylation signals are located 3' or downstream of the coding region.

Agronomic trait: Characteristic of a plant, which characteristics include, but are not limited to, plant morphology, physiology, growth and development, yield, nutritional enhancement, disease or pest resistance, or environmental or chemical tolerance are agronomic traits. An "enhanced agronomic trait" refers to a measurable improvement in an agronomic trait including, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this disclosure can also be used to provide plants having improved growth and development, and ultimately increased yield, as the result of modified expression of plant growth regulators or modification of cell cycle or photosynthesis pathways. Additional examples of agronomic traits, and altering such traits in plants, are provided herein and/or will be recognized by those of ordinary skill in the art.

Alterations: Alterations in a polynucleotide (for example, a polypeptide encoded by a nucleic acid of the present invention), as this term is used herein, comprise any deletions, insertions, and point mutations in the polynucleotide sequence. Included within this definition are alterations to the genomic DNA sequence that encodes the polypeptide. Likewise, the term "alteration" may be used to refer to deletions, insertions, and other mutations in polypeptide sequences.

Altering level of production or expression: Changing, either by increasing or decreasing, the level of production or expression of a nucleic acid molecule or an amino acid molecule (for example an mRNA, a gene, a polypeptide, or a peptide), as compared to a control level of production or expression.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antisense, Sense, and Antigene: DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA (asRNA) is a molecule of RNA complementary to a sense (encoding) nucleic acid molecule.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples.

Cell: Cell as used herein includes a plant cell, whether isolated, in tissue culture or incorporated in a plant or plant part.

Cell elongation bHLH protein (CEB1): A basic helix-loop-helix (bHLH) transcription factor controlling cell expansion in a variety of plants such as in the following species: *Vitis vinifera* (vV, wine grape, Cabernet sauvignon), *Prunus persica* (peach), *Citrus senensis* (sweet orange), *Theobroma cacao* (Cacao), *Fragaria vesca* (strawberry) or *Ananas cosmosus* (pineapple). The nucleic acid and protein sequences for CEB1 are publicly available. An exemplary CEB1 from *Vitis vinifera* wild-type nucleic acid sequence is set forth in SEQ ID NO. 1 (see FIG. 1, top sequence). In one example, CEB1 includes a full-length wild-type (or native) sequence, as well as CEB1 allelic variants, fragments, homologs or fusion sequences that retain the ability to be expressed at increased levels in a plant cell and increase tissue succulence. In certain examples, CEB1 has at least 70% sequence identity, for example at least 75%, 80%, 85%, 90%, 95%, or 98% sequence identity to wild-type CEB1, including between 95% and 100%, 98% and 100%, 80% and 100%, 85% and 100%, 99% and 100%, or 90% and 100%.

Chimeric or Chimera: The product of the fusion of portions of two or more different polynucleotide or polypeptide molecules. For instance, the phrases "chimeric sequence" and "chimeric gene" refer to nucleotide sequences derived from at least two heterologous parts. Chimeric sequence may comprise DNA or RNA.

Chimeric transcription regulatory region: An array of nucleic acid control or regulatory sequences that direct transcription of a nucleic acid operably linked thereto, which array is assembled from different polynucleotide sources. For instance, chimeric transcription regulatory regions as described herein may be produced through manipulation of known promoters or other polynucleotide molecules. Chimeric transcription regulatory regions may combine one or more enhancer domains with one or more promoters, for example, by fusing a heterologous enhancer domain from a first native promoter to a second promoter with its own partial or complete set of regulatory element(s).

Construct: Any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

Control plant: A plant that does not contain a recombinant DNA that confers (for instance) an enhanced or altered agronomic trait in a transgenic plant, is used as a baseline for comparison, for instance in order to identify an enhanced or altered agronomic trait in the transgenic plant. A suitable control plant may be a non-transgenic plant of the parental line used to generate a transgenic plant, or a plant that at least is non-transgenic for the particular trait under examination (that is, the control plant may have been engineered to contain other heterologous sequences or recombinant DNA molecules). Thus, a control plant may in some cases be a transgenic plant line that comprises an empty vector or marker gene, but does not contain the recombinant DNA, or does not contain all of the recombinant DNAs, in the test plant.

Crassulacean Acid Metabolism (CAM): A specialized form of photosynthesis found in about 6% of vascular plants. It is a carbon fixation pathway that evolved in some plants as an adaptation to water-limited (semi-arid and arid environments) or $CO_2$-limited (aquatic environments) conditions. In a plant using full CAM, the stomata in the leaves remain shut during the day to reduce evapotranspiration, but open at night to collect carbon dioxide ($CO_2$). The $CO_2$ is stored as the four-carbon acid malate in vacuoles at night, and then in the daytime, the malate is transported to chloroplasts where it is converted back to $CO_2$, which is then used during photosynthesis. The pre-collected $CO_2$ is concentrated around the enzyme RuBisCO, increasing photosynthetic efficiency. This metabolism was first studied in plants of the Crassulaceae family. These mainly include succulents. The first time it was studied, *Crassula* was used as a model organism.

DNA (deoxyribonucleic acid): DNA is a long chain polymer which comprises the genetic material of most organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule includes the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods known to those skilled in the art, the polynucleotide molecule can be transcribed and/or translated to produce a mRNA for and/or the polypeptide or a fragment thereof. The anti-sense strand is the complement of such a nucleic acid, and the encoding sequence can be deduced therefrom.

Enhancer domain: A cis-acting transcriptional regulatory element (a.k.a. cis-element) that confers an aspect of the overall control of gene expression. An enhancer domain may function to bind transcription factors, which are trans-acting protein factors that regulate transcription. Some enhancer domains bind more than one transcription factor, and transcription factors may interact with different affinities with more than one enhancer domain. Enhancer domains can be identified by a number of techniques, including deletion analysis (deleting one or more nucleotides from the 5' end or internal to a promoter); DNA binding protein analysis using DNase I foot printing, methylation interference, electrophoresis mobility-shift assays, in vivo genomic foot printing by ligation-mediated PCR, and other conventional assays; or by DNA sequence comparison with known cis-element motifs using conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation.

(Gene) Expression: Transcription of a DNA molecule into a transcribed RNA molecule. More generally, the processes by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased). Gene expression may be described as related to temporal, spatial, developmental, or morphological qualities as well as quantitative or qualitative indications.

Gene regulatory activity: The ability of a polynucleotide to affect transcription or translation of an operably linked transcribable or translatable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may include a promoter, intron, leader, or 3' transcription termination region.

Heterologous: A type of sequence that is not normally (e.g., in the wild-type sequence) found adjacent to a second sequence. In one embodiment, the sequence is from a different genetic source, such as a virus or organism or species, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. In RNA molecules, G also will bond to U. Complementary refers to the base pairing that occurs between two distinct nucleic acid sequences or two distinct regions of the same nucleic acid sequence.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions and is not meant to be limiting.

Very High Stringency (Detects Sequences that Share 90% Sequence Identity)
   Hybridization: 5×SSC at 65° C. for 16 hours
   Wash twice: 2×SSC at room temperature (RT) for 15 minutes each
   Wash twice: 0.5×SSC at 65° C. for 20 minutes each High Stringency (Detects Sequences that Share 80% Sequence Identity or Greater)
   Hybridization: 5×-6×SSC at 65° C.-70° C. for 16-20 hours
   Wash twice: 2×SSC at RT for 5-20 minutes each
   Wash twice: 1×SSC at 55° C.-70° C. for 30 minutes each Low Stringency (Detects Sequences that Share Greater than 50% Sequence Identity)
   Hybridization: 6×SSC at RT to 55° C. for 16-20 hours
   Wash at least twice: 2×-3×SSC at RT to 55° C. for 20-30 minutes each.

In cis: Indicates that two sequences are positioned on the same piece of RNA or DNA.

In trans: Indicates that two sequences are positioned on different pieces of RNA or DNA.

Industrial crop: Crops grown primarily for consumption by humans or animals or for use in industrial processes (for example, as a source of fatty acids for manufacturing or sugars for producing alcohol). It will be understood that in many instances either the plant or a product produced from the plant (for example, sweeteners, oil, flour, or meal) can be consumed; thus, a subset of industrial crops are food crops. Examples of food crops include, but are not limited to, corn, soybean, rice, wheat, oilseed rape, tomato, cotton, oats, barley, *Camelina*, tobacco and potato plants. Other examples of industrial crops (including food crops) are listed herein.

Increased Expression: Gene upregulation includes any detectable increase in the production of a gene product. In certain examples, production of a gene product increases by at least 2-fold, for example at least 3-fold or at least 4-fold, as compared to a control (such an amount of gene expression in a wild-type cell).

Isolated: An "isolated" biological component (such as a nucleic acid, peptide or protein) has been substantially separated, produced apart from, or purified away from other biological components in the cell of the organism in which the component naturally occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Metabolome: The complement of relatively low molecular weight molecules (metabolites) that is present in a single organism, a sample, a tissue, a cell, or whatever other division is divided. By way of example, metabolomes may include metabolic intermediates, hormones and other signaling molecules, and secondary metabolites. Representative metabolomes comprise the complement of metabolites found within a biological sample, such as a plant, plant part, or plant sample, or in a suspension or extract thereof. Examples of such molecules include, but are not limited to: acids and related compounds; mono-, di-, and tri-carboxylic acids (saturated, unsaturated, aliphatic and cyclic, aryl, alkaryl); aldo-acids; keto-acids; lactone forms; gibberellins; abscisic acid; alcohols, polyols, derivatives, and related compounds; ethyl alcohol, benzyl alcohol, methanol; propylene glycol, glycerol, phytol; inositol, furfuryl alcohol, menthol; aldehydes, ketones, quinones, derivatives, and related compounds; acetaldehyde, butyraldehyde, benzaldehyde, acrolein, furfural, glyoxal; acetone, butanone; anthraquinone; carbohydrates; mono-, di-, tri-saccharides; alkaloids, amines, and other bases; pyridines (including nicotinic acid, nicotinamide); pyrimidines (including cytidine, thymine); purines (including guanine, adenine, xanthines/hypoxanthines, kinetin); pyrroles; quinolines (including isoquinolines); morphinans, tropanes, cinchonans; nucleotides, oligonucleotides, derivatives, and related compounds; guanosine, cytosine, adeno sine, thymidine, inosine; amino acids, oligopeptides, derivatives, and related compounds; esters; phenols and related compounds; heterocyclic compounds and derivatives; pyrroles, tetrapyrroles (corrinoids and porphines/porphyrins, w/w/o metal-ion); flavonoids; indoles; lipids (including fatty acids and triglycerides), derivatives, and related compounds; carotenoids, phytoene; and sterols, isoprenoids including terpenes.

Native or wild-type relative to a given plant trait or phenotype: A reference to the form in which that trait or phenotype is found in the same variety of plant in nature.

Nucleotide: The term nucleotide includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Oligonucleotide: An oligonucleotide is a plurality of nucleotides joined by phosphodiester bonds, between about 6 and about 300 nucleotides in length. An oligonucleotide analog refers to compounds that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA Operably linked: This term refers to a juxtaposition of components, particularly nucleotide sequences, such that the normal function of the components can be performed. Thus, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. A coding sequence that is "operably linked" to regulatory sequence(s) refers to a configuration of nucleotide sequences wherein the coding sequence can be expressed under the regulatory control (e.g., transcriptional and/or translational control) of the regulatory sequences.

ORF (open reading frame): A series of nucleotide triplets (codons) coding for amino acids without any termination codons. These sequences are usually translatable into a peptide.

Plant: Any plant and progeny thereof. The term also includes parts of plants, including seed, cuttings, tubers, fruit, flowers, etc. In various embodiments, the term plant refers to cultivated plant species, such as corn, cotton, canola, sunflower, soybeans, sorghum, alfalfa, wheat, rice, plants producing fruits and vegetables, and turf and ornamental plant species. The term plant cell, as used herein, refers to the structural and physiological unit of plants, consisting of a protoplast and the surrounding cell wall. The term plant organ, as used herein, refers to a distinct and visibly differentiated part of a plant, such as root, stem, leaf or embryo. More generally, the term plant tissue refers to any tissue of a plant in planta or in culture. This term includes a whole plant, plant cell, plant organ, protoplast, cell culture, or any group of plant cells organized into a structural and functional unit. Plant height. Plant height is taken from the top of the soil to the tip of the plant, and is typically measured in centimeters or inches. Plant parts.

Includes protoplasts, leaves, stems, roots, root tips, anthers, pistils, seed, embryo, pollen, ovules, cotyledon, hypocotyl, flower, shoot, tissue, petiole, cells, calli, pods, meristematic cells and the like. Includes plant cells of a tissue culture from which soybean plants can be regenerated.

Polynucleotide molecule: Single- or double-stranded DNA or RNA of genomic or synthetic origin; that is, a polymer of deoxyribonucleotide or ribonucleotide bases, respectively, read from the 5' (upstream) end to the 3' (downstream) end.

Polypeptide molecule: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

*Populus euphratica* xyloglucan endotransglucosylase/hydrolase (PeXTH): A gene isolated from *P. euphratica* and overexpression of which has been shown to enhance salinity tolerance in tobacco plants. The nucleic acid and protein sequences for PeXTH are publicly available. For example, GENBANK® Accession No.: NM 001304300 discloses a PeXTH nucleic acid sequence which is incorporated by reference as provided by GENBANK® on Nov. 13, 2015. Han et al. (J. Exp. Bot. 64(14): 4225-4238, 2013) provide exemplary sequences for PeXTH. In one example, PeXTH includes a full-length wild-type (or native) sequence, as well as PeXTH allelic variants, fragments, homologs or fusion sequences that retain the ability to be expressed at increased levels in a plant cell and increase tissue succulence. In certain examples, PeXTH has at least 80% sequence identity, for example at least 85%, 90%, 95%, or 98% sequence identity to wild-type PeXTH.

Progeny: Offspring; descendants.

Promoter: An array of nucleic acid control sequences which direct transcription of a nucleic acid, by recognition and binding of e.g., RNA polymerase II and other proteins (trans-acting transcription factors) to initiate transcription. A promoter includes necessary nucleic acid sequences near the start site of transcription, such as, in the case of a polymerase II type promoter, a TATA element. Minimally, a promoter typically includes at least an RNA polymerase binding site together and may also include one or more transcription factor binding sites which modulate transcription in response to occupation by transcription factors. Representative examples of promoters (and elements that can be assembled to produce a promoter) are described herein. Promoters may be defined by their temporal, spatial, or developmental expression pattern.

A plant promoter is a native or non-native promoter that is functional in plant cells.

Protein: A biological molecule, for example a polypeptide, expressed by a gene and comprised of amino acids.

Protoplast: An isolated plant cell without a cell wall, having the potential for being transformed and/or regeneration into cell culture or a whole plant.

Purified: The term purified does not require absolute purity; rather, it is intended as a relative term. Thus, for example, a purified fusion protein preparation is one in which the fusion protein is more enriched than the protein is in its generative environment, for instance within a cell or in a biochemical reaction chamber. Preferably, a preparation of fusion protein is purified such that the fusion protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Regulatable promoter: A promoter with activity of which is regulated (directly or indirectly) by an agent, such as a transcription factor, a chemical compound, an environmental condition, or a nucleic acid molecule.

Regulating gene expression: Processes of controlling the expression of a gene by increasing or decreasing the expression, production, or activity of an agent that affects gene expression. The agent can be a protein, such as a transcription factor, or a nucleic acid molecule which when in contact with the gene or its upstream regulatory sequences, or a mRNA encoded by the gene, either increases or decreases gene expression.

Regulatory sequences or elements: These terms refer generally to a class of polynucleotide molecules (such as DNA molecules, having DNA sequences) that influence or control transcription or translation of an operably linked transcribable polynucleotide molecule, and thereby expression of genes. Included in the term are promoters, enhancers, leaders, introns, locus control regions, boundary elements/ insulators, silencers, matrix attachment regions (also referred to as scaffold attachment regions), repressor, transcriptional terminators (a.k.a. transcription termination regions), origins of replication, centromeres, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also known as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Transcriptional terminators are regions within the gene vicinity that RNA polymerase is released from the template. Origins of replication are regions of the genome that, during DNA synthesis or replication phases of cell division, begin the replication process of DNA. Meiotic recombination hotspots are regions of the genome that recombine more frequently than the average during meiosis. Specific nucleotides within a regulatory region may serve multiple functions. For example, a specific nucleotide may be part of a promoter and participate in the binding of a transcriptional activator protein.

Isolated regulatory elements that function in cells (for instance, in plants or plant cells) are useful for modifying plant phenotypes, for instance through genetic engineering.

RNA: A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum). Total RNA refers to a heterogeneous mixture of all types of RNA molecules.

Regeneration: The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Seed: The part of a flowering plant that typically contains the embryo with its protective coat and stored food and that can develop into a new plant under the proper conditions; fertilized and mature ovule.

Seed quality: The visual rating of the completeness of the seed. The score is based on the completeness of the seed coat and overall soundness of the seed. Scores range from 1 to 5, with a score of 1 indicating good quality seed and a score of 5 indicating the seeds are of poor quality.

Seed yield: The yield in bushels/acre (bu/a) and is the actual yield of the grain at harvest.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the sequences referenced or disclosed herein will possess a relatively high degree of sequence identity when aligned using standard methods.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS.* USA 85: 2444, 1988); Higgins and Sharp (*Gene,* 73: 237-244, 1988); Higgins and Sharp (*CABIOS* 5: 151-153, 1989); Corpet et al. (*Nuc. Acids Res.* 16: 10881-90, 1988); Huang et al. (*Comp. Appls Biosci.* 8: 155-65, 1992); and Pearson et al. (*Methods in Molecular Biology* 24: 307-31, 1994). Altschul et al. (*Nature Genet.,* 6: 119-29, 1994) presents a detailed consideration of sequence alignment methods and homology calculations.

The alignment tools ALIGN (Myers and Miller, *CABIOS* 4: 11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at biology.ncsa.uiuc.edu.

Orthologs or paralogs (more generally, homologs) of the disclosed sequences are typically characterized by possession of greater than 75% sequence identity counted over the full-length alignment with the sequence to which they are compared using ALIGN set to default parameters. Sequences with even greater similarity to the reference sequences will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins. In such an instance, percentage identities will be essentially similar to those discussed for full-length sequence identity.

When significantly less than the entire sequence is being compared for sequence identity, homologs will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods can be found at World Wide Web address biology.ncsa.uiuc.edu. One of skill in the art will appreciate that these sequence identity ranges are provided for guidance only; it is entirely possible that strongly significant homologs could be obtained that fall outside of the ranges provided. The present disclosure provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual,* Cold Spring Harbor, N.Y., 1989) and Tijssen (*Laboratory Techniques in Biochemistry and Molecular Biology* Part I, Ch. 2, Elsevier, New York, 1993). Nucleic acid molecules that hybridize under stringent conditions typically hybridize to a probe based on either the entire fusion protein encoding sequence, an entire binding domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Tissue culture: A composition that includes isolated cells of the same or a different type or a collection of such cells organized into parts of a plant.

Transcription: The production of an RNA molecule by RNA polymerase as a complementary copy of a DNA sequence.

Transcription termination region: Sequences that control formation of the 3' end of a transcript. Self-cleaving ribozymes and polyadenylation sequences are examples of transcription termination sequences.

Transformation: Process by which exogenous DNA enters and changes a recipient cell. It may occur under natural conditions, or artificial conditions using various methods well known in the art. Transformation may rely on any known method for the insertion of foreign nucleic acid sequences into a prokaryotic or eukaryotic host cell. Selection of the method is influenced by the host cell being transformed and may include, but is not limited to, viral infection, *Agrobacterium*-mediated gene transfer, electroporation, lipofection, and particle bombardment.

Transformed: A transformed cell is a cell into which has been introduced a nucleic acid molecule by molecular biology techniques. Transformed cells include stably transformed cells in which the inserted DNA is capable of replication either as an autonomously replicating plasmid or as part of the host chromosome. They also include cells that transiently express the inserted DNA or RNA for limited periods of time. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

Transgenic: This term refers to a plant/cell/other entity or organism that contains recombinant genetic material not normally found in entities of this type/species (that is, heterologous genetic material) and which has been introduced into the entity in question (or into progenitors of the entity) by human manipulation. Thus, a plant that is grown from a plant cell into which recombinant DNA is introduced by transformation (a transformed plant cell) is a transgenic plant, as are all offspring of that plant that contain the introduced transgene (whether produced sexually or asexually).

Transgenic plant: A plant that contains a foreign (heterologous) nucleotide sequence inserted into either its nuclear genome or organellar genome.

Transposon: A nucleotide sequence such as a DNA or RNA sequence that is capable of transferring location or moving within a gene, a chromosome or a genome.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

*Vitis vinifera* bHLH protein (VvCEB1): A basic helix-loop-helix (bHLH) transcription factor controlling cell expansion in grape. The nucleic acid and protein sequences for VvCEB1 are publicly available. For example, GENBANK® Accession No.: JQ823168 discloses a VvCEB1 nucleic acid sequence, and GENBANK® Accession No.: AFM30926.1 a protein sequence, each of which is incorporated by reference as provided by GENBANK® on Nov. 13, 2015. An exemplary VvCEB1 wild-type nucleic acid sequence is set forth in SEQ ID NO. 1 (see FIG. 1, top sequence). Exemplary codon optimized VvCEB1 nucleic acid sequence is set forth in FIG. 1 below the top sequence.

In one example, VvCEB1 includes a full-length wild-type (or native) sequence, as well as VvCEB1 allelic variants, fragments, homologs or fusion sequences that retain the ability to be expressed at increased levels in a plant cell and increase tissue succulence. In certain examples, VvCEB1 has at least 80% sequence identity, for example at least 85%, 90%, 95%, or 98% sequence identity to wild-type VvCEB1.

III. Description of Several Embodiments

A. Methods

Methods of altering plant succulence are disclosed herein. In some embodiments a disclosed method includes overexpressing a modified basic helix-loop-helix transcription factor CEB1, such as a codon optimized CEB1 or functional fragment thereof, in a plant cell, thereby altering plant succulence. In embodiments the methods includes overexpressing a modified helix-loop-helix transcription factor CEB1, such as a codon optimized CEB1 or functional fragment thereof, from one or more of: *Vitis vinifera* (winegrape); *Citrus sinensis* (sweet orange); *Prunus persica* (Peach); *Theobroma cacao* (Cacao); *Ananas comosus* (Pineapple); and *Fragaria vesca* (Strawberry), such as a nucleic acid sequence at least 80%, at least 85%, at least 90%, at least 91%, at least 92%, at least 93%, at least 94%, at least 95%, at least 96%, at least 97%, at least 98%, or at least 99% identical to the sequence set forth as any one of SEQ ID NOs: 3-9, in a plant cell, thereby altering plant succulence. In some examples, the method further comprises overexpressing a codon optimized *Populus euphratica* xyloglucan endotransglucosylase/hydrolase (PeXTH) or functional fragment thereof in a plant cell either alone or with a modified CEB1 nucleic acid sequence, such as a codon optimized CEB1 or functional fragment thereof, for example from one or more of: *Vitis vinifera* (winegrape); *Citrus sinensis* (sweet orange); *Prunus persica* (Peach); *Theobroma cacao* (Cacao); *Ananas comosus* (Pineapple); and *Fragaria vesca* (Strawberry), such as a nucleic acid sequence at least 80%, at least 85%, at least 90%, at least 91%, at least 92%, at least 93%, at least 94%, at least 95%, at least 96%, at least 97%, at least 98%, or at least 99% identical to the sequence set forth as any one of SEQ ID NOs: 3-9, in a plant cell. In some examples, the method further comprises overexpressing a codon optimized *Populus euphratica* xyloglucan endotransglucosylase/hydrolase (PeXTH) in a plant cell either alone or with a modified CEB1 nucleic acid sequence, such as a codon optimized CEB1 or functional fragment thereof, for example from *Vitis vinifera* (winegrape), such as a nucleic acid sequence at least 80%, at least 85%, at least 90%, at least 91%, at least 92%, at least 93%, at least 94%, at least 95%, at least 96%, at least 97%, at least 98% or at least 99% identical to the sequence set forth as SEQ ID NO: 3, in a plant cell. In embodiments, the modified CEB1 comprises a CEB1 with codons with frequencies of less than 0.15% altered. In some examples, method comprises overexpressing a modified VvCEB1 comprising a VvCEB1 with codons with frequencies of less than 15% per thousand codons were altered to more closely match *Arabidopsis* and *Populus* codon usage. In some examples, a total of 56 nucleotides (6.9%) out of the 810 nucleotides of VvCEB1 were altered for ectopic overexpression. In some examples, at least of the highlighted codons in FIG. 1A were modified, such as between 1 and 56, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 codons. In some examples, a modified VvCEB1 nucleic sequence shares at least 80% sequence identity, such as at least 80%, at least 85%, at least 90%, at least 91%, at least 92%, at least 93%, at least 94%, at least 95%, at least 96%, at least 97%, at least 98% or at least 99% sequence identity to SEQ ID NO: 1 and is capable of enhancing a tissue succulent property. In some examples, the nucleic acid sequence of the modified VvCEB1 is set forth as SEQ ID NO: 3. In some embodiments, a modified CEB1 sequence nucleic sequence shares at least 80% sequence identity, such as at least 80%, at least 85%, at least 90%, at least 91%, at least 92%, at least 93%, at least 94%, at least 95%, at least 96%, at least 97%, at least 98% or at least 99% sequence identity to the sequence set forth as any one of SEQ ID NOs: 3-9 and is capable of enhancing a tissue succulent property.

In embodiments, the method includes inserting the a modified helix-loop-helix transcription factor CEB1, such as a codon optimized CEB1, from one or more of: *Vitis vinifera* (winegrape); *Citrus sinensis* (sweet orange); *Prunus persica* (Peach); *Theobroma cacao* (Cacao); *Ananas comosus* (Pineapple); and *Fragaria vesca* (Strawberry), such as a nucleic acid sequence at least 80%, at least 85%, at least 90%, at least 91%, at least 92%, at least 93%, at least 94%, at least 95%, at least 96%, at least 97%, at least 98% or at least 99% identical to the sequence set forth as any one of SEQ ID NOs: 3-9, into a vector construct and transforming the plant cell with the generated vector construct. In some examples, the method includes inserting the a modified basic helix-loop-helix transcription factor CEB1, such as a codon optimized CEB1, from *Vitis vinifera* (winegrape), such as a nucleic acid sequence at least 80%, at least 85%, at least 90%, at least 91%, at least 92%, at least 93%, at least 954%, at least 95%, at least 96%, at least 97%, at least 98% or at least 99% identical to the sequence set forth as SEQ ID NO: 1, into a vector construct and transforming the plant cell with the generated vector construct.

The disclosed methods can be used to improve the drought attenuation or tolerance of plants, such as in plants in arid environments, and also enhance the ability of plants to perform. In some examples, a disclosed method is used to increase one or more of plant cell size, leaf size, leaf number, biomass, hypocotyl width, inflorescence width, inflorescence height, plant root size, plant root length, increase plant root branching, plant root biomass, plant inflorescence stem thickness, plant tissue succulence, plant water content, leaf chlorophyll content, leaf protein content, leaf soluble sugar content, plant flower size, plant floral organ size, plant silique, fruit size, plant seed size, plant seed area, plant seed mass, plant seed number, plant total seed production, leaf auxin content, auxin-related leaf shape, plant inflorescence number, increased leaf instantaneous or integrate water-use efficiency, and increased salinity tolerance or any combination thereof. In some examples, an increase is an at least 1.2-fold increase, such as at least 1.5- or an at least 2-fold increase, including between a 1.2- to 1.5-fold increase, a 1.3- to a 1.6-fold increase, a 1.2- to 2-fold increase, including 1.2-, 1.3-, 1.4-, 1.5-, 1.6-, 1.7-, 1.8-, 1.9-, 2.0-, 2.5-, 3.0-, 3.5-, 4.0-, 4.5- or 5-fold increase as compared to property of interest in a control plant.

In some examples, a disclosed method is used to decrease one or more of hypocotyl length, plant leaf water loss; leaf stomatal aperture, leaf stomatal density, and leaf stomatal conductance, or any combination thereof. In some examples, a decrease is an at least 1.2-fold decrease, such as at least 1.5- or an at least 2-fold decrease, including between a 1.2- to 1.5-fold decrease, a 1.3- to a 1.6-fold decrease, a 1.2- to a 2-fold, including 1.2-, 1.3-, 1.4-1.5-, 1.6-, 1.7-, 1.8-, 1.9-, 2.0-, 2.5-, 3.0-, 3.5-, 4.0-, 4.5- or 5-fold decrease as compared to property of interest in a control plant.

In some examples, the method is used to generate a plant with improved drought and salinity tolerance. In some examples, the method is used to delay plant flowering time, such as up to two weeks. In other examples, the method is used to stimulate plant flowering. In some examples, the method is used to reduce intracellular air space with the resulting plant becoming an anatomically optimized host for performance of (engineered) crassulacean acid metabolism (CAM). In some examples, the method is used to increase plant tolerance to salinity and related salts that impose an ionic stress. In some examples, the methods are used to increase plant tolerance to osmotic stress, such as to mannitol or PEG, and related osmotic agents that impose an osmotic stress. In some examples, the methods are used to increase plant tolerance to acute and/or chronic water-deficit (drought) stress imposed by a lack of water availability.

B. CEB1 Nucleic Acids and Proteins

The present disclosure provides previously unrecognized CEB1 nucleic acids and codon optimized forms thereof, such as cDNA and mRNA from *Vitis vinifera* (winegrape) (SEQ ID NO: 3); *Citrus sinensis* (sweet orange) (SEQ ID NO: 4); *Prunus persica* (Peach) (SEQ ID NO: 5); *Theobroma cacao* (Cacao) (SEQ ID NO: 6); *Ananas comosus* (Pineapple) SEQ ID NO: 7); and *Fragaria vesca* (Strawberry) SEQ ID NO: 8), such as set forth in SEQ ID NOs: 3-9. To optimize codon usage in sequenced genomes of other plant species, codon usage tables were generated from the following species using available gene coding sequences: *Aquilegia coerulea, Aquilegia coerulea, Amaranthus hypochondriacus, Amborella trichopoda, Ananas cosmosus, Arabidopsis halleri, Arabidopsis lyrata, Arabidopsis thaliana columbia, Boechera stricta, Brachypodium distachyon, Brachypodium stacei, Brassica rapa, Capsella grandiflora, Capsella rubella, Carica papaya, Chlamydomonas reinhardtii, Citrus clementina, Citrus sinensis, Coccomyxa subellipsoidea, Cucumis sativus, Daucus carota, Dunaliella salina, Eucalyptus grandis, Eutrema salsugineum, Fragaria vesca, Glycine max, Gossypium raimondii, Kalanchoe laxiflora, Kalanchoe marnieriana, Linum usitatissimum, Malus domestica, Manihot esculenta, Medicago truncatula, Micromonas pusilla, Micromonas sp, Mimulus guttatus, Musa acuminata, Oryza sativa, Ostreococcus lucimarinus, Oropetium thomaeum, Panicum hallii, Panicum virgatum, Panicum virgatum, Phaseolus vulgaris, Physcomitrella patens, Populus trichocarpa, Prunus persica, Ricinus communis, Salix purpurea, Selaginella moellendorffii, Setaria italica, Setaria viridis, Solanum lycopersicum, Solanum tuberosum, Sorghum bicolor, Spirodela polyrhiza, Sphagnum fallax, Theobroma cacao, Trifolium pratense, Triticum aestivum, Vitis vinifera, Volvox carteri,* and *Zea mays.* These codon use tables were then used to design the target codon-optimized gene encoding CEBs. The diversity of codon usage in these plant species represented by the IUPAC ambiguity codes. While particular nucleic acid sequences have been shown for each of the CEB1 nucleic acids set forth as SEQ ID NOS: 3-9, it is understood that a CEB1 nucleic acid sequence includes any nucleic acid sequence redundant by virtue of the degeneracy of genetic code that encodes a protein, or functional fragment thereof. Variants of the disclosed CEB1 nucleic acids, such as cDNA and mRNA, are also contemplated by this disclosure. Variant nucleotide sequences also include synthetically derived nucleotide sequences, such as those generated, for example, by using site-directed mutagenesis, but which when expressed still exhibit CEB1 activity. Methods for mutagenesis and nucleotide sequence alterations are known in the art. See, for example, Kunkel (1985) Proc. Natl. Acad. Sci. USA 52:488-492; Kunkel et al. (1987) Methods in Enzymol. 75:367-382; U.S. Pat. No. 4,873,192; Walker and Gaastra, eds. (1983) Techniques in Molecular Biology (MacMillan Publishing Company, New York) and the references cited therein. It will further be understood that amino acid sequences encoded by the disclosed CEB1 nucleic acids will typically tolerate substitutions in the amino acid sequence and substantially retain biological activity. Thus, disclosed are nucleotide acids having at least 80% sequence identity to a nucleic acid sequence encoding the polypeptide that is encoded by the nucleic acid set forth as one of SEQ ID NOs: 3-9, such as a nucleic acid sequence at least 80%, at least 85%, at least 90%, at least 91%, at least 92%, at least 93%, at least 94%, at least 95%, at least 96%, at least 97%, at least 98% or at least 99% sequence identity or even greater. In some examples, a CEB1 nucleic acid is at least 80% identical to the nucleic acid set forth as one of SEQ ID NOs: 3-9, such as a nucleic acid sequence at least 80%, at least 85%, at least 90%, at least 91%, at least 92%, at least 93%, at least 94%, at least 95%, at least 96%, at least 97%, at least 98% or at least 99% identical to the sequence set forth as one of SEQ ID NOs: 3-9.

To routinely identify biologically active proteins, amino acid substitutions may be based on any characteristic known in the art, including the relative similarity or differences of the amino acid side-chain substituents, for example, their hydrophobicity, hydrophilicity, charge, size, and the like. Generally, nucleotide sequence variants will encode a protein have at least 80% sequence identity to the protein encoded by a disclosed CEB1 nucleic acid, such as a nucleic acid sequence at least 80%, at least 85%, at least 90%, at least 91%, at least 92%, at least 93%, at least 94%, at least 95%, at least 96%, at least 97%, at least 98% or at least 99% sequence identity or even greater to the protein encoded by its respective reference CEB1 nucleotide sequence.

In some embodiments, a disclosed CEB1 nucleic acid encodes a functional fragment of a CEB1 protein. Such functional fragments still exhibit CEB1 activity. Functional fragments include proteins in which residues at the N-terminus, C-terminus and/or internal to the full length protein have been deleted. For example, a deletion of less than about 50, 40, 30, 25, 20, 15, 10, 5, 4, 3, 2, or 1 amino acids from the N-terminus, C-terminus and/or internal loops can be made while maintaining the active site with minimal testing and/or experimentation to determine the activity of the resultant protein. Also disclosed are isolated proteins that have at least 80% sequence homology to the polypeptide encoded by a nucleic acid with nucleic acid sequence set forth by one of SEQ ID NOs: 3-9 or a degenerate nucleic acid, such as a nucleic acid sequence at least 80%, at least 85%, at least 90%, at least 91%, at least 92%, at least 93%, at least 94%, at least 95%, at least 96%, at least 97%, at least 98%, or at least 99% sequence identity or even greater to the protein encoded by a nucleic acid sequence set forth by one of SEQ ID NOs: 3-9 or a degenerate nucleic acid.

The nucleotide sequences for the disclosed CEB1s, such a nucleic acid sequence encoding (such as having at least 80% sequence homologs to the nucleic acid sequence set forth by one of SEQ ID NOs: 3-9, such as at least 80%, at least 85%, at least 90%, at least 91%, at least 92%, at least 93%, at least 94%, at least 95%, at least 96%, at least 97%, at least 98% or at least 99% to the nucleic acid sequence set forth by one of SEQ ID NOs: 3-9 or a degenerate, or functional fragment thereof, are useful in the genetic manipulation plant cells when operably linked with a promoter, such as an indictable or constitutive promoter. In this manner, the nucleotide sequences for the CEB1s are provided in expression cassettes for expression in the plant of interest. Such expression cassettes will typically comprise a transcriptional initiation region comprising a promoter nucleotide sequence operably linked to one or more of the disclosed nucleic acids or variants thereof. Such an expression cassette can be provided with a plurality of restriction sites for insertion of the nucleotide sequence to be under the transcriptional regulation of the regulatory regions. The expression cassette may additionally contain selectable marker genes or sequences. The expression cassettes of this disclosure can be part of and an expression vector, such as a plasmid.

In some embodiments, the transcriptional cassette will include in the 5'-to-3' direction of transcription, a transcriptional and translational initiation region, a nucleic acid sequence encoding CEB1 (such as having at least 80% sequence identity to the nucleic acid sequence set forth by one of SEQ ID NOs: 3-9 or a degenerate nucleic acid) or functional fragment thereof, and a transcriptional and translational termination region functional in plant cells. The termination region may be native with the transcriptional initiation region, may be native with the CEB1, or may be derived from another source. Convenient termination regions are available from the Ti-plasmid of *A. tumefaciens*, such as the octopine synthase and nopaline synthase termination regions. See also, Guerineau et al., Mol. Gen. Genet. 262:141-144, 1991; Proudfoot Cell 64:671-674, 1991; Sanfacon et al., Genes Dev. 5:141-149, 1991; Mogen et al., Plant Cell 2:1261-1272, 1990; Munroe et al., Gene 91:151-158, 1990; Ballas et al., Nucleic Acids Res. 17:7891-7903, 1989; Joshi et al., Nucleic Acid Res. 15:9627-9639, 1987.

An expression cassette including a disclosed CEB1 operably linked to a promoter sequence may also contain at least additional nucleotide sequence for a gene to be cotransformed into the organism. Alternatively, the additional sequence(s) can be provided on another expression cassette. Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., Proc. Nat. Acad.

Sci. USA 86:6126-6130, 1989); potyvirus leaders, for example, TEV leader (Tobacco Etch Virus); MDMV leader (Maize Dwarf Mosaic Virus); human immunoglobulin heavy-chain binding protein (BiP) (Macejak and Sarnow Nature 353:90-94, 1991); untranslated leader from the coat protein mRNA of alfalfa mosaic virus (AMV RNA 4) (Jobling and Gehrke Nature 325:622-625, 1987); tobacco mosaic virus leader (TMV) (Gallie et al. Molecular Biology of RNA, pages 237-256, 1989; and maize chlorotic mottle virus leader (MCMV) (Lommel et al., Virology 81:382-385, 1991). See also Della-Cioppa et al., Plant Physiology 84:965-968, 1987. Other methods known to enhance translation and/or mRNA stability can also be utilized, for example, introns, and the like.

In some embodiments, a disclosed isolated polynucleotide sequences comprises a plant promoter and a codon optimized CEB1 polynucleotide sequence. In some examples, the codon optimized CEB1 polynucleotide sequence comprises a CEB1 polynucleotide sequence with codons with frequencies of less than 0.15% altered. In some examples, a modified CEB1 nucleic sequence shares at least 80%, at least 85%, at least 90%, at least 91%, at least 92%, at least 93%, at least 94%, at least 95%, at least 96%, at least 97%, at least 98%, or at least 99% sequence identity or even greater to a nucleic acid sequence set forth by one of SEQ ID NOs: 3-9, and is capable of enhancing a tissue succulent property. In some examples, the polynucleotide sequence comprises the plant promoter is CaMV35S operably linked to a CEB1 nucleic acid sequence. Numerous promoters useful for heterologous gene expression are available including, but not limited to, E4 (U.S. Pat. Nos. 5,783,393 and 5,783,394), CaMV19S, CaMVV1, Act1, Ubi1, or CsVMV promoters. Also disclosed are isolated polynucleotide sequences comprising a plant promoter and a codon optimized VvCEB1 polynucleotide sequence. In some examples, the codon optimized VvCEB1 polynucleotide sequence comprises a VvCEB1 polynucleotide sequence with codons with frequencies of less than 0.15% altered. In some examples, a total of 56 nucleotides (6.9%) out of the 810 nucleotides of VvCEB1 were altered for ectopic overexpression. In some examples, at least of the highlighted codons in FIG. 1 were modified, such as between 1 and 56, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 codons. In some examples, a modified VvCEB1 nucleic sequence shares at least 90% sequence identity, such as about 93%, 94%, 95%, 96%, 97%, 98% or 99% sequence identity to SEQ ID NO: 1 and is capable of enhancing a tissue succulent property. In some examples, the nucleic acid sequence of the modified VvCEB1 is set forth in SEQ ID NO: 3. In some examples, the polynucleotide sequence comprises the plant promoter is CaMV35S operably linked to a VvCEB1 nucleic acid sequence. Numerous promoters useful for heterologous gene expression are available including, but not limited to, E4 (U.S. Pat. Nos. 5,783,393 and 5,783,394 which are hereby incorporated by reference), CaMV19S, CaMVV1, Act1, Ubi1, or CsVMV promoters.

In those instances where it is desirable to have the expressed product of the CEB1 directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated by methods known in the art, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The expression cassettes may include reporter genes or selectable marker genes. Examples of suitable reporter genes known in the art can be found in, for example, Jefferson et al. in Plant Molecular Biology Manual, ed. Gelvin et al. (Kluwer Academic Publishers), pp. 1-33, 1991; DeWet et al., Mol. Cell. Biol. 7:725-737, 1987; Goff et al., EMBO J. 9:2517-2522, 1990; and Kain et al., BioTechniques 19:650-655, 1995; and Chiu et al., Current Biology 6:325-330, 1996. Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al., EMBO J. 2:987-992, 1983); methotrexate (Herrera Estrella et al., Nature 303:209-213, 1983; Meijer et al., Plant Mol. Biol. 16:807-820, 1991); hygromycin (Waldron et al., Plant Mol. Biol. 5:103-108, 1985; Zhijian et al., Plant Science 108:219-227, 1995); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990); sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); and phosphinothricin (DeBlock et al., EMBO J. 6:2513-2518, 1987).

Other genes that could serve utility in the recovery of transgenic events but might not be required in the final product would include, but are not limited to, such examples as GUS (β-glucuronidase; Jefferson Plant Mol. Biol. Rep. 5:387, 1987), GFP and other related fluorescent proteins, and luciferase.

Plant transformation vectors comprising a disclosed isolated polynucleotide sequence are also provided. Moreover, transgenic plant cells, plant part, and plants comprising a disclosed vector construct whereby the transgenic plant has increased expression levels of CEB1 as compared to a control plant resulting in enhanced tissue succulence relative to control plants are provided.

A wide variety of transformation techniques exist in the art, and new techniques are continually becoming available. Any technique that is suitable for the target host plant can be employed within the scope of the present disclosure. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid construct comprising the CEB1 coding sequence. The transformation of the plant is preferably permanent, i.e. by integration of the introduced expression constructs into the host plant genome, so that the introduced constructs are passed onto successive plant generations.

In one embodiment, binary based vector systems may be used to transfer and confirm the association between enhanced expression of an identified gene with a particular plant trait or phenotype. Standard *Agrobacterium* binary vectors are known to those of skill in the art and many are commercially available. In some examples, the binary vectors pGWB415 and pGWB402 are employed.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, root tissue, floral tissue, and immature embryo tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature.

Depending upon the intended use, a heterologous nucleic acid construct may be made which comprises a CEB1 nucleic acid sequence, and which encodes the entire protein, or a biologically active portion thereof for transformation of plant cells and generation of transgenic plants.

The expression of a CEB1 nucleic acid sequence or an ortholog, homologue, variant or fragment thereof may be carried out under the control of a constitutive, inducible or regulatable promoter. In some cases, expression of the CEB1 nucleic acid sequence or homologue, variant or fragment thereof may regulated in a developmental stage or tissue-associated or tissue-specific manner. Accordingly, expression of the nucleic acid coding sequences described herein may be regulated with respect to the level of expression, the tissue type(s) where expression takes place and/or developmental stage of expression leading to a wide spectrum of applications wherein the expression of a CEB1 coding sequence is modulated in a plant.

Strong promoters with enhancers may result in a high level of expression. Expression of CEB1 nucleic acid sequence or homologue, variant or fragment thereof may also be controlled at the level of transcription, by the use of cell type specific promoters or promoter elements in the plant expression vector.

Standard molecular and genetic tests may be performed to analyze the association between a cloned gene and an observed phenotype. A number of other techniques that are useful for determining (predicting or confirming) the function of a gene or gene product in plants are described below in the Examples.

C. Expression of CEB1s

The present disclosure describes nucleic acids encoding CEB1 proteins obtained from various plant species, such as set forth in SEQ ID NOs: 3-9 or functional fragment thereof. Also provided are DNA constructs comprising the described nucleic acids encoding CEB1 proteins. Host cells including a disclosed nucleic acid are also provided as well as methods of producing CEB1 from such host cells. In one embodiment, the CEB1 confers an agronomic trait to a plant in which it is expressed, for example regulation of tissue succulence. The CEB1 nucleic acids disclosed herein include recombinant DNA which is incorporated into a vector; into an autonomously replicating plasmid or virus; or into the genomic DNA of a prokaryote or eukaryote, or which exists as a separate molecule (for example, a cDNA) independent of other sequences. DNA sequences encoding CEB1, such can be expressed in vitro by DNA transfer into a suitable host cell. The cell may be prokaryotic or eukaryotic. The term also includes any progeny of the subject host cell. It is understood that all progeny may not be identical to the parental cell because there may be mutations that occur during replication. Methods of stable transfer, meaning that the foreign DNA is continuously maintained in the host, are known in the art. Such host cells can be used to CEB1. Thus, disclosed are methods for producing CEB1.

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR. A nucleic acid encoding a CEB1 can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

CEB1 nucleic acids, such as cDNA sequences encoding CEB1 polypeptides, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (for instance, ATG) in front of a protein-encoding gene, splicing signal for introns, maintenance of the correct reading frame of that gene to permit proper translation of mRNA, and stop codons.

Transformation of a host cell with recombinant DNA may be carried out by conventional techniques as are well known to those skilled in the art. Where the host is prokaryotic, such as *E. coli*, competent cells, which are capable of DNA uptake can be prepared from cells harvested after exponential growth phase and subsequently treated by the $CaCl_2$) method using procedures well known in the art. Alternatively, $MgCl_2$, or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed.,).

In some embodiments, inserting CEB1 nucleic acid, such as one or more of SEQ ID Nos: 1, and 3-9 into the genome of a cell, such as a plant cell includes using a genome editing system, such as a CRISPR-Cas system, a TALEN system, a ZFN system, a meganuclease, and the like.

As disclosed herein, mutations in cells, such as the insertion of CEB1 nucleic acids, can be made by way of the CRISPR-Cas system or a Cas9-expressing eukaryotic cell or a Cas-9 expressing eukaryote. The Cas9-expressing eukaryotic cell or eukaryote, can have guide RNA delivered or administered thereto, whereby the RNA targets a loci and induces a desired mutation for use in or as to the invention. With respect to general information on CRISPR-Cas Systems, components thereof, and delivery of such components, including methods, materials, delivery vehicles, vectors, particles, and making and using thereof, including as to amounts and formulations, as well as Cas9-expressing eukaryotic cells, Cas-9 expressing eukaryotes, such as a mouse, reference is made to: U.S. Pat. Nos. 8,697,359, 8,771,945, 8,795,965, 8,865,406, 8,871,445, 8,889,356, 8,889,418, 8,895,308, 8,932,814, 8,945,839, 8,906,616; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents/Patent Applications: EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), and vMultiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013); Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi:10.1038/nbt.3026, each of which is incorporated herein by reference.

As disclosed herein, mutations in cells, such as the insertion of CEB1 nucleic acids, can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

As disclosed herein, mutations in cells, such as the insertion of CEB1 nucleic acid can be made by way of the zinc-finger nucleases (ZFNs) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746, 838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

As disclosed herein, mutations in cells, such as the insertion of CEB1 nucleic acid, can be made by way of meganucleases, which are endodeoxyribonucleases characterized by a large recognition site (double-stranded DNA sequences of 12 to 40 base pairs). Exemplary method for using megonucleases can be found in U.S. Pat. Nos. 8,163, 514; 8,133,697; 8,021,867; 8,119,361; 8,119,381; 8,124, 369; and 8,129,134, which are specifically incorporated by reference.

The expression and purification of any of CEB1 proteins, by standard laboratory techniques, is now enabled. Fragments amplified as described herein can be cloned into standard cloning vectors and expressed in commonly used expression systems consisting of a cloning vector and a cell system in which the vector is replicated and expressed. Purified proteins may be used for functional analyses. Partial or full-length cDNA sequences, which encode for the protein, may be ligated into bacterial expression vectors. Methods for expressing large amounts of protein from a cloned gene introduced into *E. coli* may be utilized for the purification, localization and functional analysis of proteins.

Intact native protein may also be produced in *E. coli* in large amounts for functional studies. Standard prokaryotic cloning vectors may also be used, for example, pBR322, pUC18, or pUC19 as described in Sambrook et al. (Molecular Cloning: A Laboratory Manual, 2nd ed., vol. 1-3, Cold Spring Harbor, N.Y. 1989). Nucleic acids of CEB1 nucleic acids, such as cDNA sequences, may be cloned into such vectors, which may then be transformed into bacteria such as *E. coli*, which may then be cultured so as to express the protein of interest. Other prokaryotic expression systems include, for instance, the arabinose-induced pBAD expression system that allows tightly controlled regulation of expression, the IPTG-induced pRSET system that facilitates rapid purification of recombinant proteins and the IPTG-induced pSE402 system that has been constructed for optimal translation of eukaryotic genes. These three systems are available commercially from INVITROGEN™ and, when used according to the manufacturer's instructions, allow routine expression and purification of proteins.

Methods and plasmid vectors for producing fusion proteins and intact native proteins in bacteria are described in Sambrook et al. (Molecular Cloning: A Laboratory Manual, Cold Spring Harbor, N.Y., 1989, Chapter 17). Such fusion proteins may be made in large amounts and are easy to purify. Proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (Molecular Cloning: A Laboratory Manual, Cold Spring Harbor, N.Y., 1989) and are well known in the art. Often, proteins expressed at high levels are found in insoluble inclusion bodies. Methods for extracting proteins from these aggregates are described by Sambrook et al. (Molecular Cloning: A Laboratory Manual, Cold Spring Harbor, N.Y., 1989, Chapter 17).

A number of viral vectors have been constructed, that can be used to express the disclosed CEB1s, including polyoma, i.e., SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Natl. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Various yeast strains and yeast-derived vectors are commonly used for expressing and purifying proteins, for example, *Pichia pastoris* expression systems are available from INVITROGEN™ (Carlsbad, Calif.). Such systems include suitable *Pichia pastoris* strains, vectors, reagents, transformants, sequencing primers and media. Non-yeast eukaryotic vectors can also be used for expression, such as mMTPSL 1, 2 and 4 through 48 polypeptides. Examples of such systems are the Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are available from INVITROGEN™.

In addition, some vectors contain selectable markers such as the gpt (Mulligan and Berg, Proc. Natl. Acad. Sci. USA 78:2072-6, 1981) or neo (Southern and Berg, J. Mol. Appl. Genet. 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., Mol. Cell. Biol. 1:486, 1981) or Epstein-Barr (Sugden et al., Mol. Cell. Biol. 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., J. Biol. Chem. 253:1357, 1978).

The transfer of DNA into eukaryotic cells is now a conventional technique. The vectors are introduced into the recipient cells as pure DNA (transfection) by, for example, precipitation with calcium phosphate (Graham and vander Eb, 1973, Virology 52:466) or strontium phosphate (Brash et al., Mol. Cell. Biol. 7:2013, 1987), electroporation (Neumann et al., EMBO J. 1:841, 1982), lipofection (Felgner et al., Proc. Natl. Acad. Sci. USA 84:7413, 1987), DEAE dextran (McCuthan et al., J. Natl. Cancer Inst. 41:351, 1968), microinjection (Mueller et al., Cell 15:579, 1978), protoplast fusion (Schather, Proc. Natl. Acad. Sci. USA 77:2163-7, 1980), or pellet guns (Klein et al, Nature 327:70, 1987). Alternatively, the cDNA can be introduced by infection with virus vectors. Systems are developed that use, for example, retroviruses (Bernstein et al., Gen. Engrg. 7:235, 1985), adenoviruses (Ahmad et al., J. Virol. 57:267, 1986), or Herpes virus (Spaete et al., Cell 30:295, 1982).

D. Transgenics

Also provided are transgenic plants. In one embodiment, a transgenic plant is stably transformed with a disclosed nucleic acid construct, such as a construct comprising a CEB1 nucleic acid. In some embodiments, the transgenic plant is a dicotyledon. In other embodiments, the transgenic plant is a monocotyledon. Further provided is a seed of a disclosed transgenic plant. In one embodiment, the seed comprises the disclosed nucleic acid construct. Even further provided is a transgenic plant cell or tissue. In one embodiment, a transgenic plant cell or tissue comprises a disclosed nucleic acid, such as set forth in SEQ ID NOs: 3-9 or functional fragment thereof. In some embodiments, the plant cell or tissue is derived from a dicotyledon. In other embodiments, the plant cell or tissue is from a monocotyledon.

Also provided are methods of producing a disclosed transgenic plant, plant cell, seed or tissue. In some embodiments, the method comprises transforming a plant cell or tissue with a disclosed nucleic acid construct.

Further provided are a plant cell, fruit, leaf, root, shoot, flower, seed, cutting and other reproductive material useful in sexual or asexual propagation, progeny plants inclusive of F1 hybrids, male-sterile plants and all other plants and plant products derivable from the disclosed transgenic plants.

In some embodiments, an expression cassette including a disclosed a nucleic acid sequence encoding CEB1 (such as having at least 80% sequence identity to the nucleic acid sequence set forth by one of SEQ ID NOs: 3-9 or a degenerate nucleic acid) or functional fragment thereof, operably linked to promoter and optionally other heterologous nucleic acids can be used to transform any plant or part thereof, such as a plant cell, for example as a vector, such as a plasmid. In this manner, genetically modified plants, plant cells, plant tissue, seed, and the like can be obtained. Such methods, include introducing into a plant, such a nucleic acid sequence encoding CEB1 (such as having at least 80% sequence identity to the nucleic acid sequence set forth by one of SEQ ID NOs: 3-9 or a degenerate nucleic acid) or functional fragment thereof, operably linked to promoter and optionally other heterologous nucleic acids.

Such methods, include introducing into a plant, a nucleic acid sequence encoding CEB1 (such as having at least 80% sequence identity to the nucleic acid sequence set forth by one of SEQ ID NOs: 3-9 or a degenerate nucleic acid) or functional fragment thereof, operably linked to promoter and optionally other heterologous nucleic acids. The plant can be transiently or stably transformed. Tissue succulence can be determined relative to a relevant control plant. The control plant is generally matched for species, variety, age, and the like and is subjected to the same growing conditions, for example temperature, soil, sunlight, pH, water, and the like. The selection of a suitable control plant is routine for those skilled in the art.

Transformation protocols as well as protocols for introducing nucleotide sequences into plants may vary depending on the type of plant or plant cell, for example, monocot or dicot, targeted for transformation. Suitable methods of introducing nucleotide sequences into plant cells and subsequent insertion into the plant genome include microinjection (Crossway et al., Biotechniques 4:320-334, 1986), electroporation (Riggs et al., Proc. Natl. Acad. Sci. USA 53:5602-5606, 1986), *Agrobacterium*-mediated transformation (U.S. Pat. No. 5,563,055), direct gene transfer (Paszkowski et al., EMBO J. 3:2717-2722, 1984), and Biolistic® particle acceleration (see, for example, U.S. Pat. No. 4,945,050; Tomes et al. "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin), 1995; and McCabe et al., Biotechnology 5:923-926, 1988). Also see Weissinger et al., Ann. Rev. Genet. 22:421-477, 1988; Sanford et al., Paniculate Science and Technology 5:27-37, 1987; Christou et al., Plant Physiol 57:671-674, 1988; McCabe et al., Bio/Technology 5:923-926, 1988; Finer and McMullen, In Vitro Cell Dev. Biol. 27P:175-182, 1991; Singh et al., Theor. Appl Genet. 95:319-324, 1998; Datta et al., Biotechnology 5:736-740, 1990; Klein et al., Proc. Natl. Acad. Sci. USA 55:4305-4309, 1988; Klein et al., Biotechnology 5:559-563, 1988; U.S. Pat. Nos. 5,240,855, 5,322,783 and 5,324,646; Klein et al., Plant Physiol 97:440-444, 1988; Fromm et al. Biotechnology 5:833-839, 1990; Hooykaas-Van Slogteren et al., Nature 377:763-764, 1984; Bytebier et al., Proc. Natl. Acad. Sci. USA 54:5345-5349, 1987; De Wet et al. (1985) in The Experimental Manipulation of Ovule Tissues, ed. Chapman et al. (Longman, N.Y.), pp. 197-209; Kaeppler et al., Plant Cell Reports 9:415-418, 1990; Kaeppler et al., Theor. Appl. Genet. 54:560-566, 1992; D'Halluin et al., Plant Cell 4:1495-1505 1992; Li et al., Plant Cell Reports 72:250-255, 1993; Christou and Ford Annals of Botany 75:407-413, 1995; Osjoda et al., Nature Biotechnology 74:745-750, 1996; and the like. "Introducing" in the context of a plant cell, plant tissue, plant part and/or plant means contacting a nucleic acid molecule with the plant cell, plant tissue, plant part, and/or plant in such a manner that the nucleic acid molecule gains access to the interior of the plant cell or a cell of the plant tissue, plant part or plant. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, for example as part of a breeding protocol.

The cells that have been transformed can be grown into plants in accordance with conventional ways. See, for example, McCormick et al. Plant Cell Reports 5:81-84, 1986. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In some embodiments, the CEB1 nucleic acid sequences disclosed herein, such as a nucleic acid sequence having at least 80% sequence identity to the nucleic acid sequence set forth by one of SEQ ID NOs: 3-9 or a degenerate nucleic acid) or active variant and fragments thereof are used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardiurn occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and various Poplar and *Eucalyptus* species.

In specific embodiments, plants of the present disclosure are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments soybean plants are optimal. Other plants of interest include grain plants that provide seeds of interest, oilseed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, the polynucleotides comprising disclosed CEB1 are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant. These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853.

The transformed plants may be analyzed for the presence of the gene(s) of interest and the expression level. Numerous methods are available to those of ordinary skill in the art for the analysis of transformed plants. For example, methods for plant analysis include Southern and northern blot analysis, PCR-based (or other nucleic acid amplification-based) approaches, biochemical analyses, phenotypic screening methods, field evaluations, and immunodiagnostic assays (e.g., for the detection, localization, and/or quantification of proteins).

The following examples are provided to better describe the present disclosure and to guide those of ordinary skill in the art in the practice of the present disclosure.

EXAMPLES

Example 1

Material and Methods

Complete Codon Optimization of VvCEB1.

The coding sequence (CDS) of VvCEB1 was codon optimized according to *Arabidopsis thaliana* and *Populus trichocarpa* codon usage tabulated from the Codon Usage Database (World Wide Web address kaxusa.or.jp/codon/) in GENNANK®. Rare codons of VvCEB1, which had frequencies of less than 0.15% were altered to more closely match common *Arabidopsis* and *Populus* codon usage (FIG. 1A, SEQ ID NO: 1). The codon-optimized CDS of VvCEB1 and 3× Human influenza hemagglutinin (HA) tag for empty vector control with attachment L1 and L2 sites were synthesized by DNA 2.0 (see World Wide Web address dna20.com/).

Plasmids Construction.

The modified VvCEB1 and 3×HA tags were cloned into plant binary vectors of pGWB415 (35Spro::3×HA-R1-R2-NOS) and pGWB402 (35Spro::R1-R2-NOS) using the Gateway LR reaction, respectively (Nakagawa et al., Bioscience Biotechnology, and Biochemistry 71: 2095-2100, 2007). FIGS. 1B-2D show schematics of exemplary constructs. After LR reactions, the recombinant plasmids of 35S:: 3×HA-VvCEB1 and 35S:: 3×HA-00 were chemically transformed into E. coli (NEB 10-beta competent E. coli, New England BioLabs, M A, USA). The plasmids were extracted and verified fully by DNA sequencing at the Nevada Genomics Center, Reno, Nev., USA. Each plasmid was chemically transformed into the Agrobacterium tumefaciens strains GV3101 and the plasmids were re-extracted from Agrobacterium and verified again by DNA sequencing.

Arabidopsis Transformation.

Agrobacterium strains containing 35S:: 3×HA-VvCEB1 and 35S:: 3×HA-00 (empty vector control) were transformed into Arabidopsis thaliana (Col-0) according to the floral-dip method (Zhang et al., Nature Protocol 1: 641-646, 2006 which is hereby incorporated by reference in its entirety). For selection of stable transgenic lines, $T_2$ seeds were placed on the 1× Murashige and Skoog (MS) agar plates containing 50 µg mL$^{-1}$ kanamycin and assessed for segregation under kanamycin selection to isolate T3 transformants. Four homozygous VvCEB1 overexpressing lines (#20, #25, #26, and #30) and two control lines of 35S:: 3×HA-00 were selected for further analysis.

Plant Materials and Growth Conditions.

Homozygous seeds of the wild-type (WT), 35S:: 3×HA-00 (empty vector control, EV), and 35S:: 3×HA-VvCEB1 Arabidopsis thaliana (Col-0) were harvested at the same time and used for the phenotypic characterization of the overexpressing-VvCEB1. For MS medium grown conditions, seeds were incubated with sterilized water and subjected to 4° C. for 3 days. After seed stratification, sterilized seeds were sown onto solid ½-strength MS medium containing 0.7% phytoagar that had been supplemented with 1% sucrose. The seedlings were grown in a growth chamber under 16 h/8 h (light, 135 µmol m-$^{2}$ s$^{-1}$/dark) cycles at 23° C./21° C. (day/night). For soil-grown conditions, seeds were sown on the soil (Sunshine 781, custom blend, 45-50% peat moss, Scotts Sierra Horticultural Products, Marysville, Ohio) and covered by plastic wrap for 2 days. The seedlings were grown in a growth chamber under 12 h/12 h (light, 135 µmol m-$^{2}$ s$^{-1}$/dark) cycles at 23° C./21° C. (day/night).

Subcellular Localization.

The modified VvCEB1 was cloned into plant binary vector of pGWB405 (35Spro::R1-R2-sGFP-NOS) using the Gateway LR reaction. Agrobacterium strain GV3101 harboring the construction of 35S::VvCEB1-sGFP was transformed into Arabidopsis and harvested $T_0$ seed. Seeds were screened on the 1×MS medium containing kanamycin and survival transformants were incubated with nuclear counterstain DAPI solution (Fluoreshield™ with DAPI, Sigma-Aldrich, F6182) for 10 min at room temperature. Root samples of 35S::VvCEB1-sGFP plants were observed using confocal laser-scanning microscopy (Olympus Fluoview FV 1000, Japan).

Measurement of Growth and Development.

The wild-type, 35S:: 3×HA-00, and 35S:: 3×HA-VvCEB1 seeds were germinated and grown on ½-strength MS medium for 21 days and fresh and dry weight of seedlings and leaf fresh and dry weight were measured at 7, 14, and 21 days after germination. After measuring fresh weight, plants were fully dehydrated at 60° C. for 24 h and dry weight were measured. For hypocotyl growth, plants were vertically positioned and grown on the ½ MS medium. 14-day-old plants were photographed and hypocotyl length and width were measured by image J software (see World Wide Web address imagej.nih.gov/ij/). After germination, seedlings were grown vertically on ½-strength MS medium for 21 days and root length, fresh weight, and dry weight were measured. Rosette diameter, leaf area, leaf number per plant were measured using soil-grown plants at 28 days after germination. Seeds were germinated onto the soil and grown for 28 days before bolting. Rosette and detached leaves were photographed and rosette diameter and leaf surface area were measured by image J. For analysis of leaf thickness and inflorescence stem diameter, fully expanded 5th leaves of 28 days after germination and primary inflorescence stem were measured using a digital micrometer (Model no. PK-1015, Mitutoyo Corp., Kawasaki, Japan).

Measurement of Leaf Succulence.

Four-week-old 35S:: 3×HA-00 and 35S:: 3×HA-VvCEB1 plants were grown in soil and the fully expanded 5th leaves were harvested for succulence analysis. Detached leaves were incubated with sterilized water for 16 h and water on the leaf surface was removed by blotting with a paper towel. The fresh weight (FW) was determined immediately and the leaf area was captured and quantified using image J software (World Wide Web address imagej.nih.gov/ij/). The dry weight (DW) was obtained after the leaf samples were oven dried at 60° C. for 24 hours. The saturated water content (SWC) was calculated as follows (Ogburn and Edwards, Plant, Cell & Environment 35: 1533-1542, 2012 which is hereby incorporated by reference in its entirety):

$$SWC=(FW-DW)/DW$$

The leaf succulence degree (LSD) was calculated as follow (Reinman and Breckle, New Phytologist. 1995; 130: 37-45):

$$LSD(gH_2O\ cm^{-2})=(FW-DW)/leaf\ area$$

Measurement of Flowering Time, Flower Size, and Seed Size.

Plants were grown in soil at 23° C./21° C. (day/night) in a growth chamber under 12 h/12 h (light, 135 µmol m-$^{2}$ s$^{-1}$/dark) conditions for six weeks. For the long-day conditions, sterilized seeds were germinated and grown on ½-strength MS medium at 23° C./21° C. (day/night) in a growth chamber under 16 h/8 h (light, 135 µmol m-$^{2}$ s$^{-1}$/dark) conditions for six weeks. Flowering times were determined by counting the days to bolting. Thirty-five plants of 35S:: 3×HA-00 and 35S:: 3×HA-VvCEB1 were counted at 7-day intervals for six weeks. To detect the effect of ABA on flowering time, seeds were germinated and grown vertically on ½ MS medium containing with different concentrations (1, 2.5, and 5 µM) of ABA for three weeks. Thirty plants per line were measured to estimate a mean value of flower size, petal number per flower, silique size, seed number per silique, seed size, and 100-seed weight. Flowers and siliques were photographed using a zoom stereomicroscope (SMZ800, Nikon Instruments Inc., Melville, N.Y., USA) and analyzed by using Image J software. Plants were harvested at maturity, and the seeds were cleaned using a sieve. Mean seed area was estimated from a sample of 100 seeds with a document scanner and analyzed using Image J software.

Seed Yield Analysis.

Plants were grown in both soil and fertilizer-supplemented soil conditions at 23° C./21° C. (day/night) in a growth chamber under 12 h/12 h (light, 135 µmol m-$^{2}$ s⁻¹/dark). To estimate maximum seed yield of 35S:: 3×HA-00 and 35S:: 3×HA-VvCEB1 plants, 2-week-old plants were applied 300 mL of 0.07% (w/v) 24-8-16/N-P-K fertilizer with micronutrients (Miracle-Gro, Marysville, Ohio, USA) every two weeks. Seeds were harvested at maturity and total seed weight per plants was measured using an electronic analytical balance (AS313, Ohaus Corp., Parsippany, N.J., USA).

Measurement of Cell Size and Number.

To measure palisade, spongy mesophyll cell size, and percentage of intercellular air space (IAS), soil-grown fully expanded $5^{th}$ leaves were sampled at 28 days after germination. Transverse sections of 3 leaves of each of 35S:: 3×HA-00 and 35S:: 3×HA-VvCEB1 plants were prepared. Small pieces of leaf (approximately 1-2×2-3 mm) were fixed in 1.5% v/v glutaraldehyde solution by vacuum infiltration for 30 min and incubated at 4° C. for 16 h. Nine leaf samples of each line were dehydrated in increasing concentrations (20, 30, 50, 70, 95, and 100%) of ethanol series for 20 min each dilution. The samples were embedded in Spurr's/Epon combination formula. Sections of 1 µm thickness were cut using an ultramicrotome (Ultracut UCT, Leica Biosystems Inc., Buffalo Grove, Ill.) and diamond knife (Diatome A G, Biel, Switzerland) and stained with toluidine blue O. Images were captured under 10× and 20× magnifications by light microscopy (Eclipse E400, Nikon Inc., Melville, N.Y., USA) and analyzed palisade, spongy mesophylls, and IAS.

To measure cell size and number of epidermis, palisade mesophylls, and stomata, tangential section were made. Fully expanded 5th leaves from soil-grown 28-day-old plants were sampled and photographed to estimate total cell numbers per leaf. Small pieces of leaf (approximately 0.5× 0.5 cm) were submerged with propidium iodide (Sigma-Aldrich) and subjected to vacuum infiltration for 20 min. Samples were washed three times with sterilized water and images were captured by laser scanning confocal microscopy (Olympus Fluoview FV 1000).

To analyze both transverse and tangential sections, cell outlines were drawn using a Wacom Cintique 13HD tablet (World Wide Web address wacom.com/) display to trace the cell size, cell number, and IAS. Each of the different cell types and IAS were assigned a unique color using Adobe Photoshop CC (World Wide Web address adobe.com/). Cell size and IAS were measured using Image J software.

Soil Drought Stress.

For water-deficit stress treatments, each combination of wild-type (WT) or 35S:: 3×HA-00 (Empty-vector control) with 35S:: 3×HA-VvCEB1 plants were grown under well-watered conditions in soil for 14 days after germination. Irrigation was withheld for 30 days and then plants rewatered for nine days. For measuring leaf water content, five leaves from each line in triplicate were detached at 3-day intervals and fresh weight measured at the indicated days. For measuring dry weight, detached leaf samples were dried at 60° C. for 24 hours and weighed using an electronic analytical balance. Measurement of polyploidy level. The wild-type, 35S:: 3×HA-00, and 35S:: 3×HA-VvCEB1 seedlings were grown on ½-strength MS medium for 21 days after germination. Roots and leaves were sampled separately in triplicate and put in between moist paper towels in a zip-lock bag and sent to Benaroya Research Institute Flow Cytometry and Imaging Core Laboratory (Seattle, Wash.) for analysis. Intact nuclei suspensions were prepared by chopping plant tissues and lysing protoplasts in $MgSO_4$ buffer. Chicken erythrocyte nuclei were used as an internal standard for these measurements. Nuclear DNA content was performed by flow cytometry (FACSort flow cytometer, Becton Dickenson, Inc., Franklin Lakes, N.J., USA) as described (Arumuganathan and Earle (Plant Molecular Biology Reporter 9: 229-241, 1991).

In Vitro Abiotic and Biotic Stress Assay.

For seed germination and green cotyledon rates, seeds of the wild-type (WT), 35S:: 3×HA-00 (empty vector control, EV), and 35S:: 3×HA-VvCEB1 were sterilized in a solution containing 30% sodium hypochlorite and 0.1% Triton X-100 for 10 min, washed five times with sterilized water, and sown on ½-strength MS medium containing different concentrations (0, 150, 200, 250, and 300 mM) of NaCl, (200, 300, 400, and 500 mM) Mannitol (Sigma-Aldrich, St. Louis, Mo., USA), (0.5, 1, 2.5, and 5 µM) abscisic acid (ABA) (Sigma-Aldrich), and (−0.25, −0.5, −0.7, −1.2, and −0.17 MPa) of polyethlylene glycol (PEG) 8000 (Sigma-Aldrich). Briefly, 20 ml of ½-strength MS with 1.5% phytoagar was solidified and then overlaid with 30 ml of a PEG solution containing 0, 250, 400, 550, and 700 g per liter of PEG 8000, yielding water potentials of −0.25, −0.5, −0.7, −1.2, or −1.7 MPa, respectively. The PEG solution was allowed to stand for 16 h and was then removed from the plates. Germination and green cotyledon percentages were scored and calculated at 1-day intervals for 7 days. For analysis of abiotic stress tolerance during vegetative stage, 7-day-old seedlings on nylon mesh (1 mm pore size) were transferred to ½-strength MS medium containing different concentrations of NaCl, Mannitol, ABA, and PEG as described above. Fresh weight and dry weight were measured at 14 days after stress treatment.

Example 2

Engineered Tissue Succulence in Plants

This example illustrates methods and constructs for regulating tissue succulence in plants.

FIG. 1A is a schematic of a native sequence of a helix-loop-helix transcription factor (VvCEB1; SEQ ID NO: 1) showing codon optimization. Highlights in the codon optimized VvCEB1 indicate the modified nucleotides. The resulting amino acid sequence is set forth as SEQ ID NO: 2, which is duplicated to show that the codon optimization did not alter the resulting amino acid sequence. FIGS. 1B-1D provide schematic representations of binary vector construct used for transformation of *Arabidopsis thaliana*. In particular, the codon-optimized sequence of VvCeb1 was synthesized and cloned into the ImpGWB415 vector containing the CaMV 35S promoter for transformation of *Arabidopsis* (shown in FIG. 1B). The synthesized 3×HA tag was cloned into the ImpGWB402 vector and transformed into *Arabidopsis* for the 35S::3×HA empty-vector control (FIG. 1C). The VvCeb1$_{opt}$ fragment was cloned into the ImpGWB405 vector containing the CaMV 35Spromoter and C-terminal synthetic green fluorescent protein (sGFP) to study subcellular localization. Kanamycin (KanR) was used as the selectable marker (FIG. 1D). T-border (R) and T-border (L) indicate T-DNA right border and T-DNA left borders, respectively.

FIG. 1E provides images illustrating nuclear localization of the VvCEB1opt-sGFP fusion protein in *A. thaliana*. The 35S::VvCEB1opt-sGFP construct was transformed into *Arabidopsis*. Seven-day-old seedlings (T1) were used to analyze subcellular localization. Images in the lower panel correspond to magnification of the regions indicated by the white squares in the upper panel. Scale bars, 40 µm (top panels) and 5 µm (bottom panels). In summary, the VvCEB1opt-sGFP fusion protein was strongly expressed and localized to the nucleus in *Arabidopsis*.

Figure 2A:
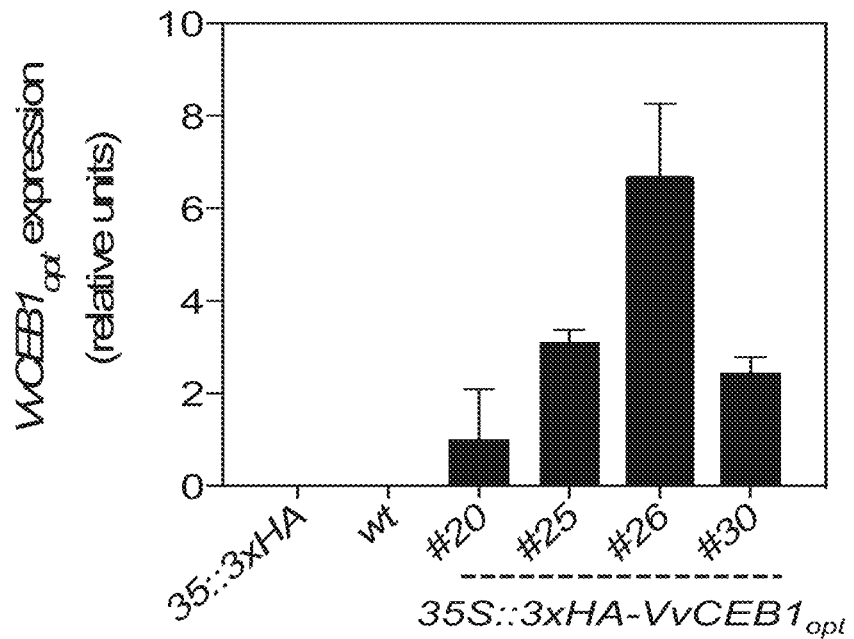
FIGS. 2A and 2B provide results of mRNA and protein expression characterization studies of VvCEB1$_{opt}$-overexpressing *Arabidopsis* lines and the 35S::3×HA empty-vector control line, respectively.
Figure 2B:
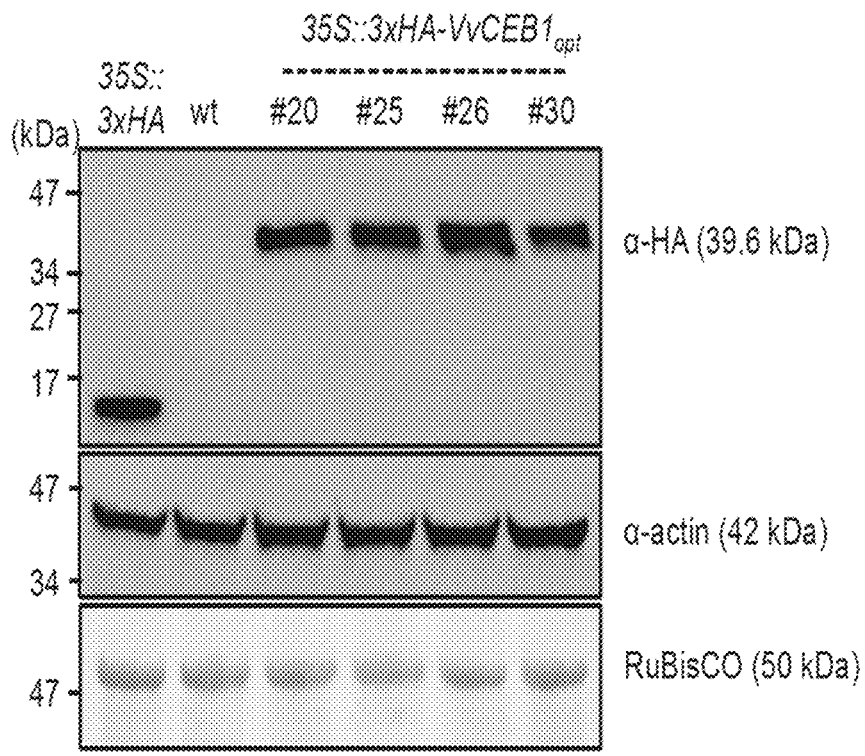

FIGS. 2A and 2B provide results of characterization studies of VvCEB1$_{opt}$-overexpressing *Arabidopsis* lines and the 35S::3×HA empty-vector control line. (FIG. 2A) Quantitative real-time PCR analysis of VvCeb1 opt transcript abundance in four independent VvCEB1$_{opt}$-overexpressing lines (#20, #25, #26, and #30), wild-type *A. thaliana* ecotype Col-0, and the 35S::3×HA empty-vector control lines. Transcript levels of VvCeb1$_{opt}$ in four different lines were quantified using TIP41-like (AT4G34270) expression as a normalization standard. Values represent means±s.d. of three biological replicates. Immunoblot analysis with anti-HA antibody (clone 3F10, Roche Applied Science, Indianapolis, Ind., USA) was performed to measure protein abundance within the 3×HA-VvCEB1 opttransgenic lines (FIG. 1D). Immunodetection of actin and Ponceau S staining of RuBisCO were used as loading controls. In summary, the 3×HA-VvCEB1$_{opt}$ fusion protein was strongly expressed in four independent transgenic lines.

Figure 3:
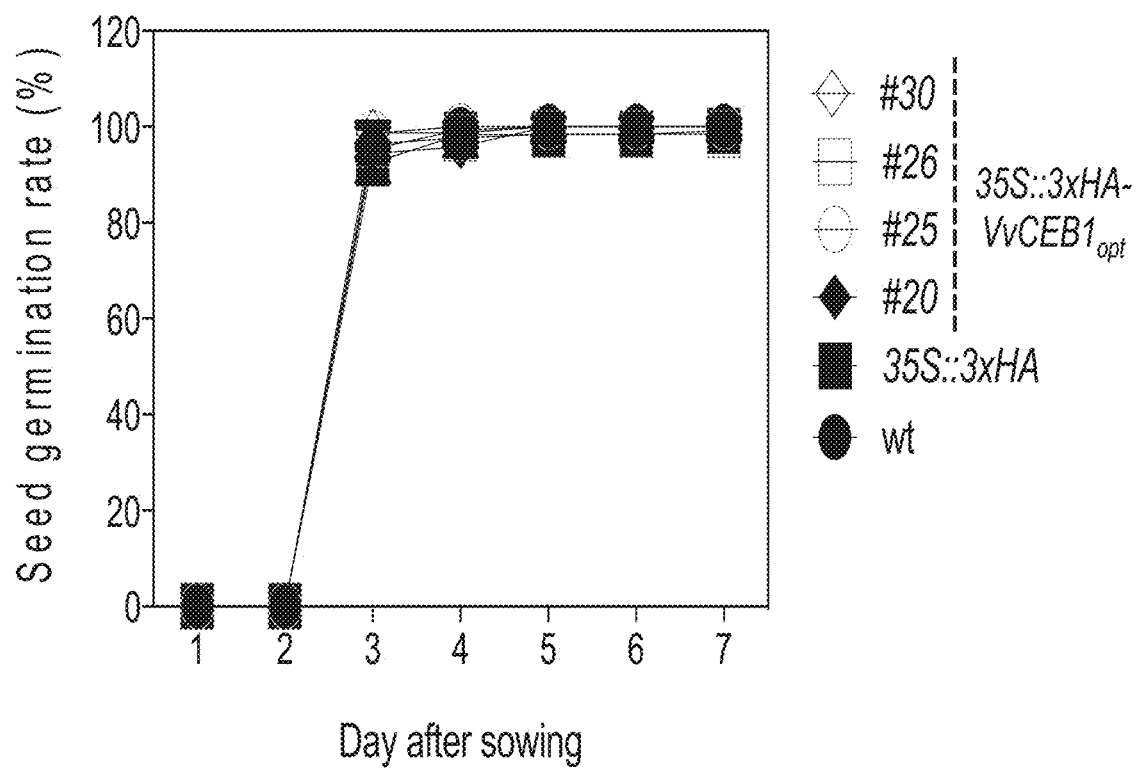
FIG. 3 illustrates seed germination rate of VvCEB1$_{opt}$ overexpression and control lines.

FIG. 3 illustrates seed germination rate of VvCEB1$_{opt}$ overexpression and control lines. Seeds were germinated and grown on MS agar medium for 7 days under a 16-hour photoperiod. Seed germination rates of four independent VvCEB1opt-overexpressing lines (#20, #25, #26, and #30), wild-type (wt) *A. thaliana* ecotype Col-0, and the 35S::3× HAempty-vector control line were scored for 7 days (n=3 replicates). In summary, the VvCEB1$_{opt}$-overexpression did not affect seed germination rate in *Arabidopsis*.

Figure 4B:
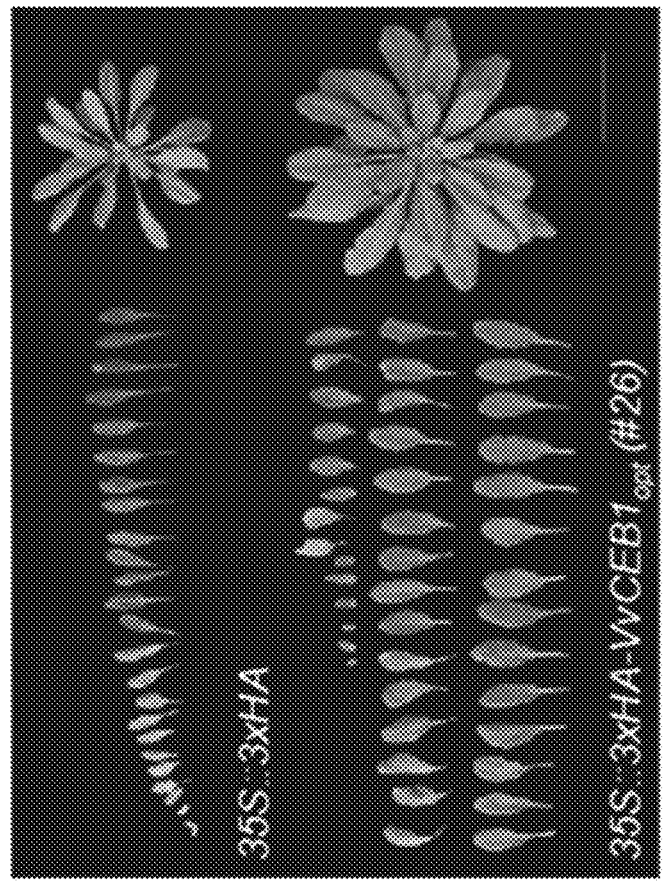
FIGS. 4A-4I illustrate overexpression of VvCEB1$_{opt}$ increases plant vegetative biomass in *Arabidopis*.
Figure 4A:
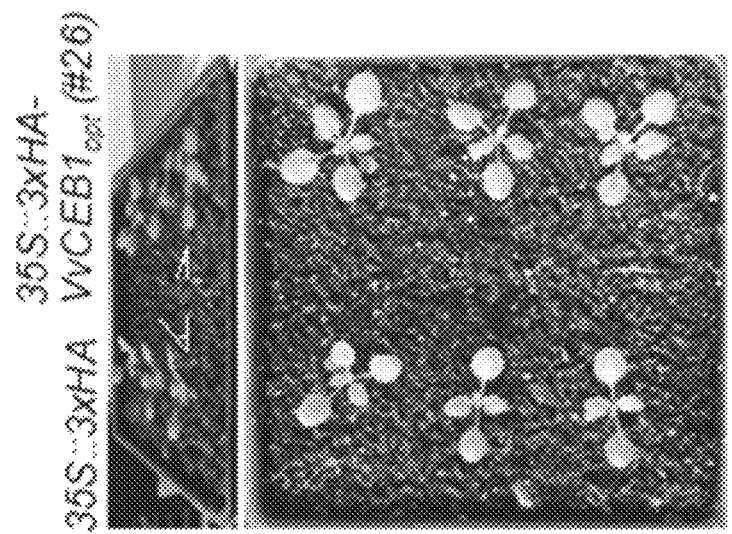
Figure 4C:
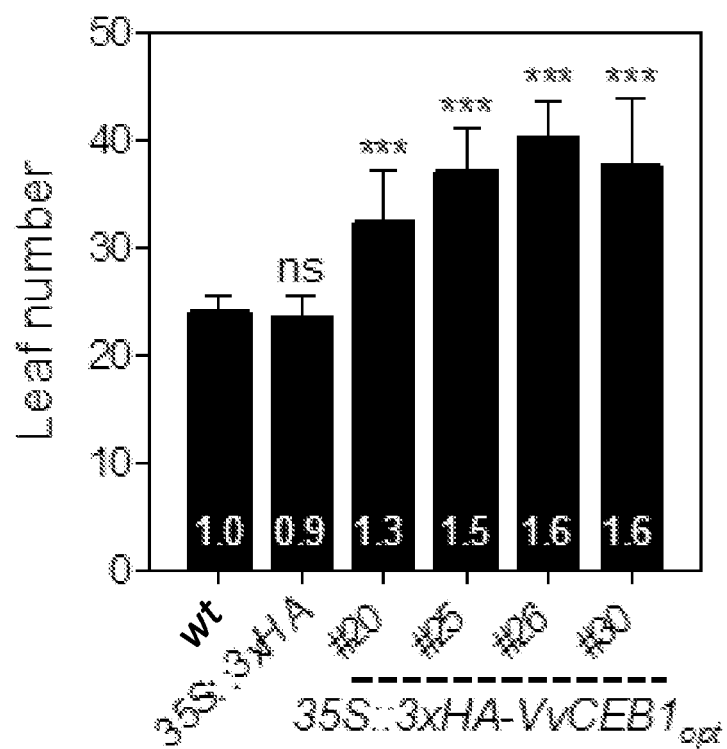
Figure 4D:
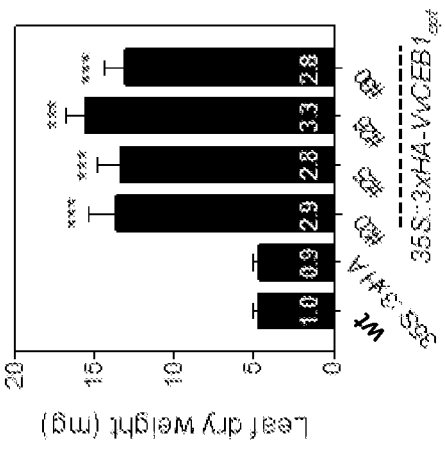
Figure 4E:
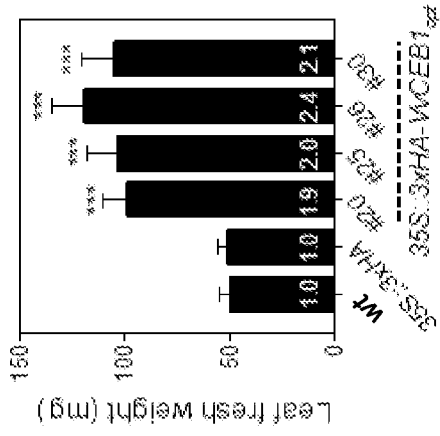
Figure 4F:
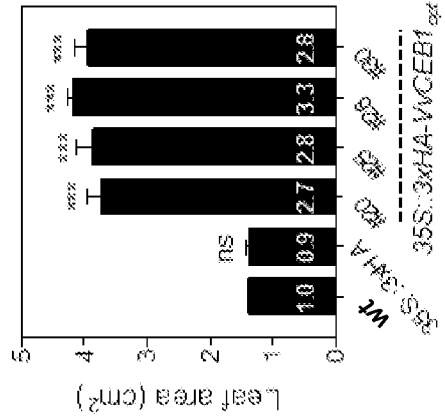
Figure 4G:
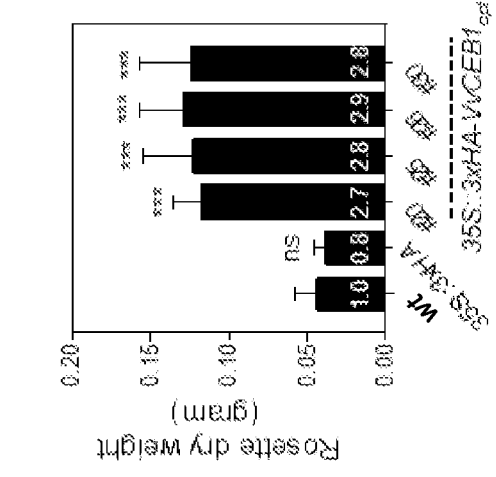
Figure 4H:
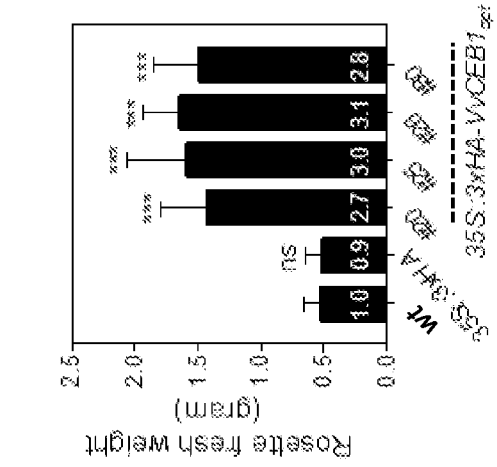
Figure 4I:
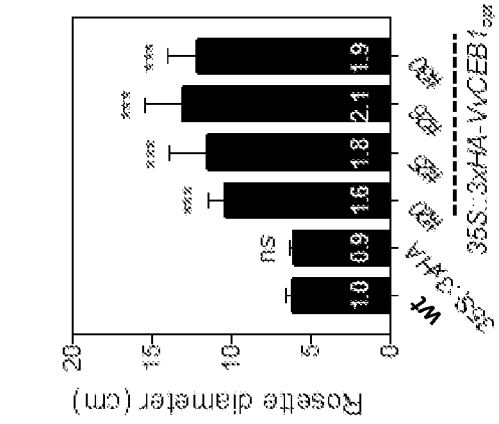
Figure 5A:
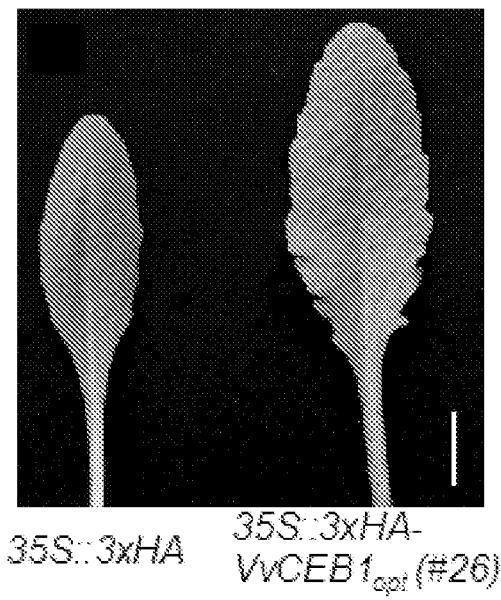
FIGS. 5A-5E illustrate overexpression of modified VvCEB1 (VvCEB1$_{opt}$) increases leaf teeth number and modulate serration along the leaf margin and increases auxin (IAA) content in leaves of *Arabidopis*.
Figure 5B:
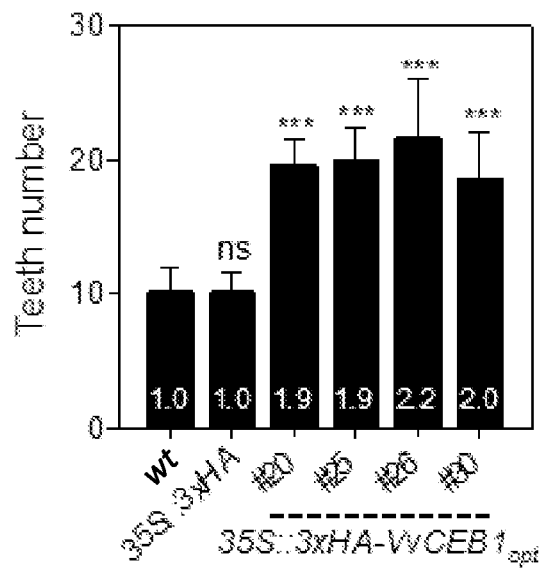
Figure 5C:
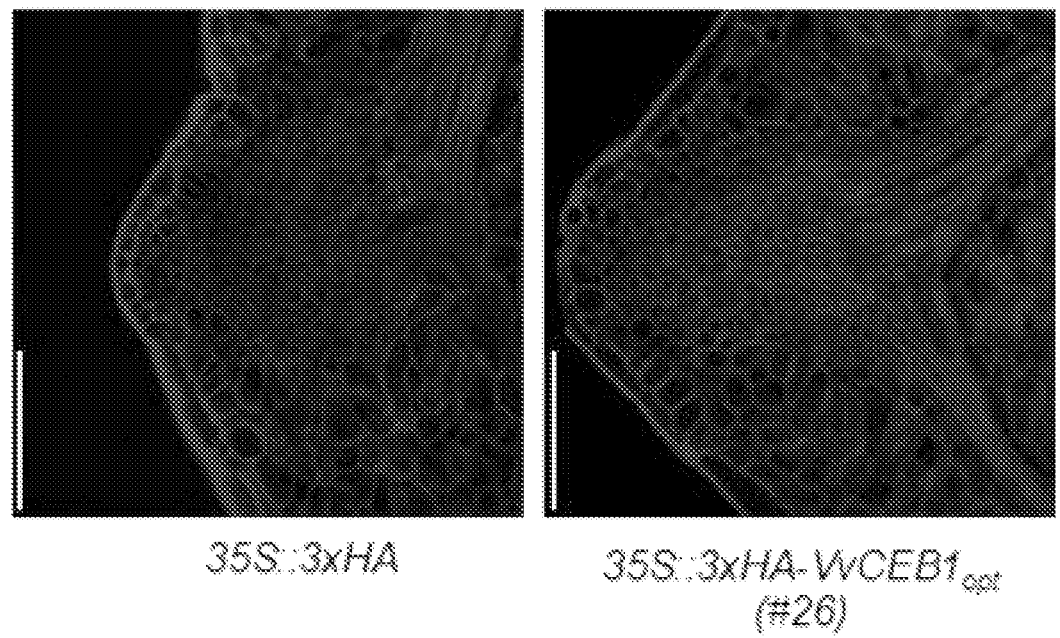
Figure 5D:
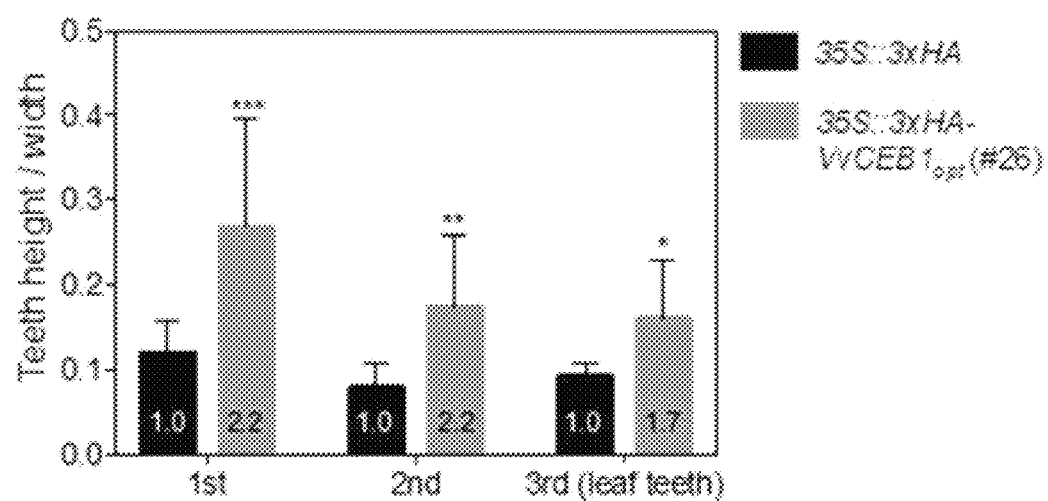
Figure 5E:
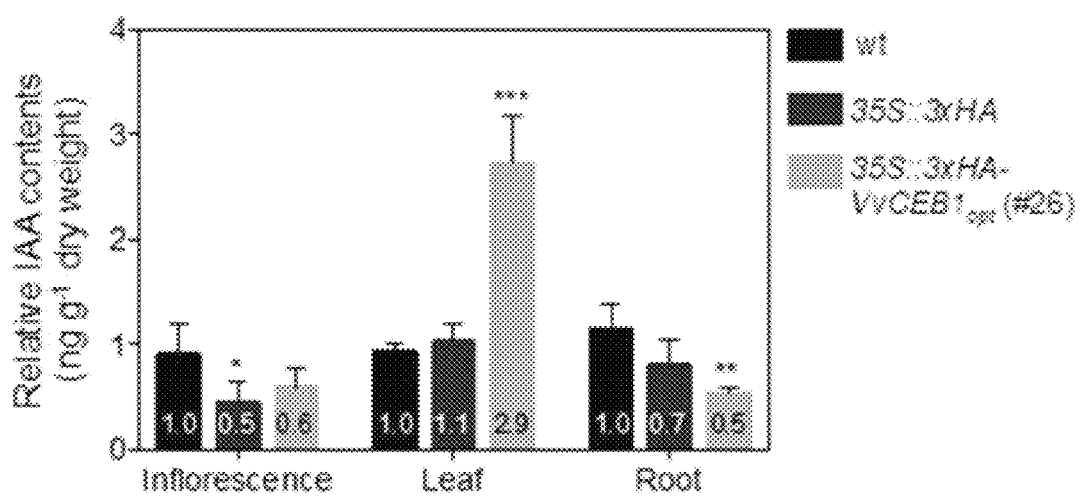
Figure 6A:
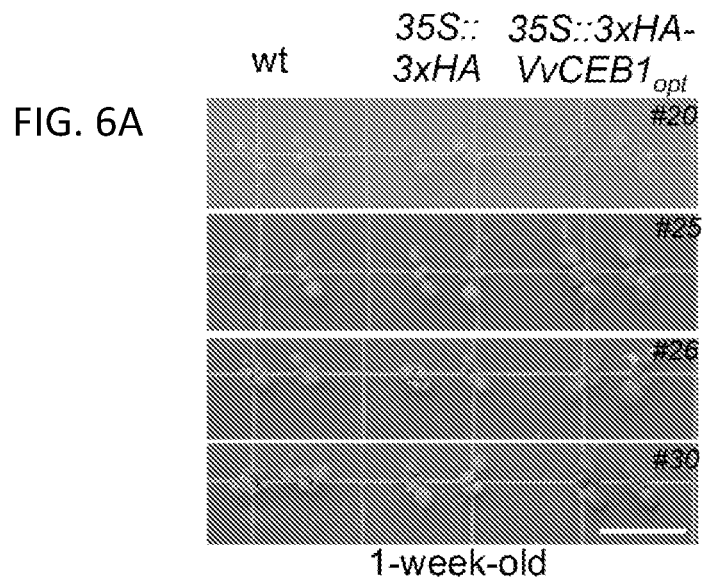
FIGS. 6A-6I illustrate overexpression of modified VvCEB1 (VvCEB1$_{opt}$) increase biomass mass in seedlings of *Arabidopsis*.
Figure 6B:
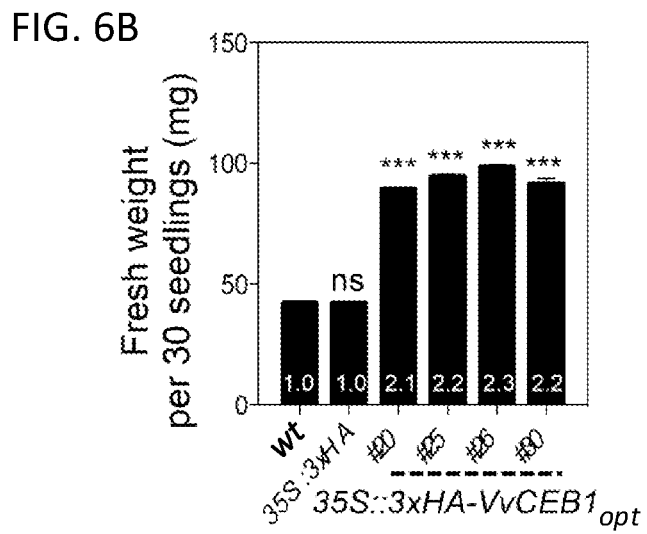
Figure 6C:
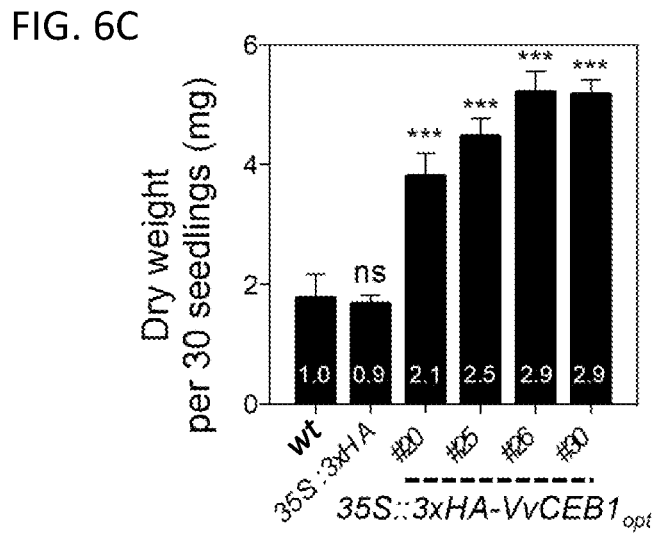
Figure 6D:
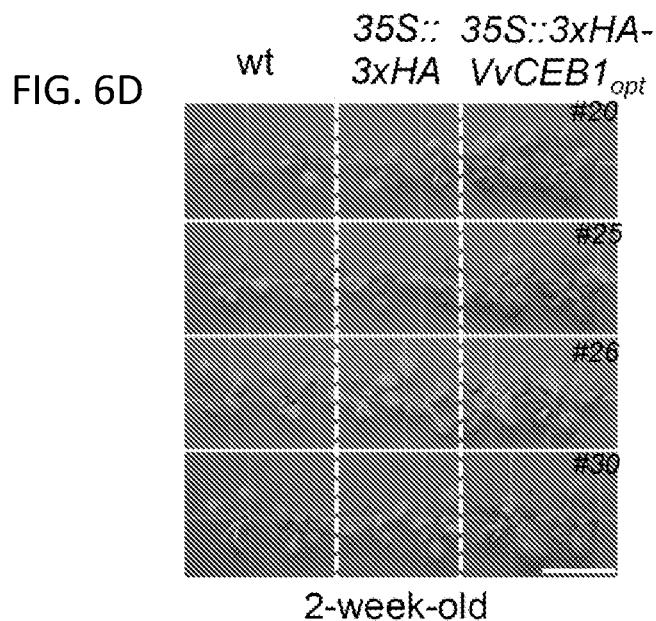
Figure 6E:
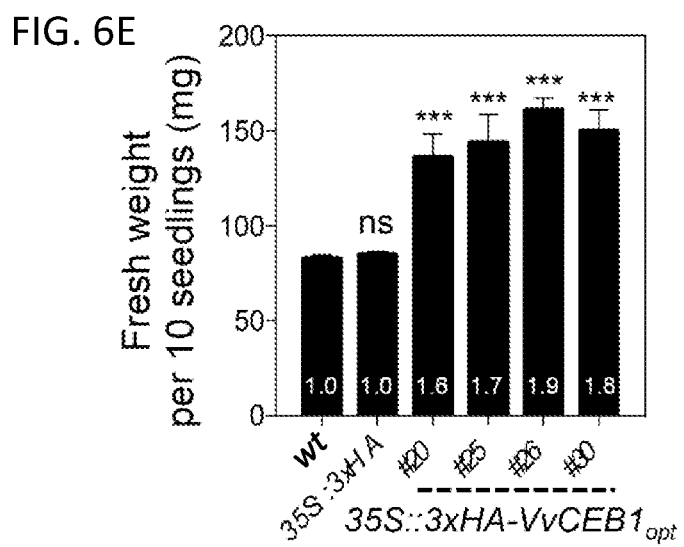
Figure 6F:
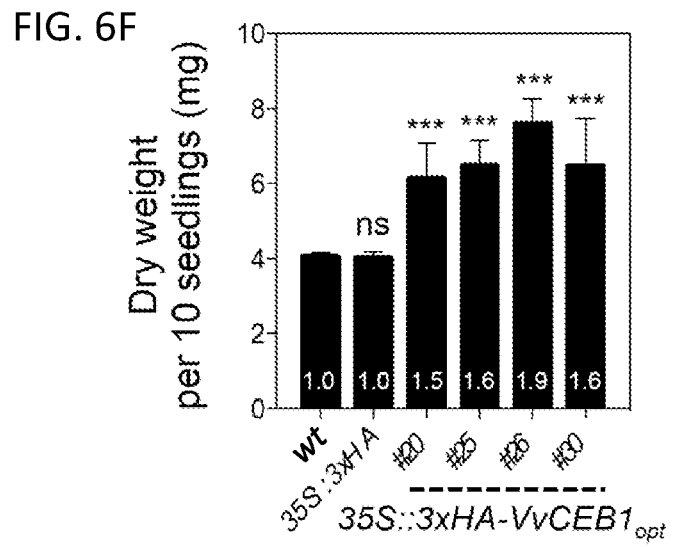
Figure 6G:
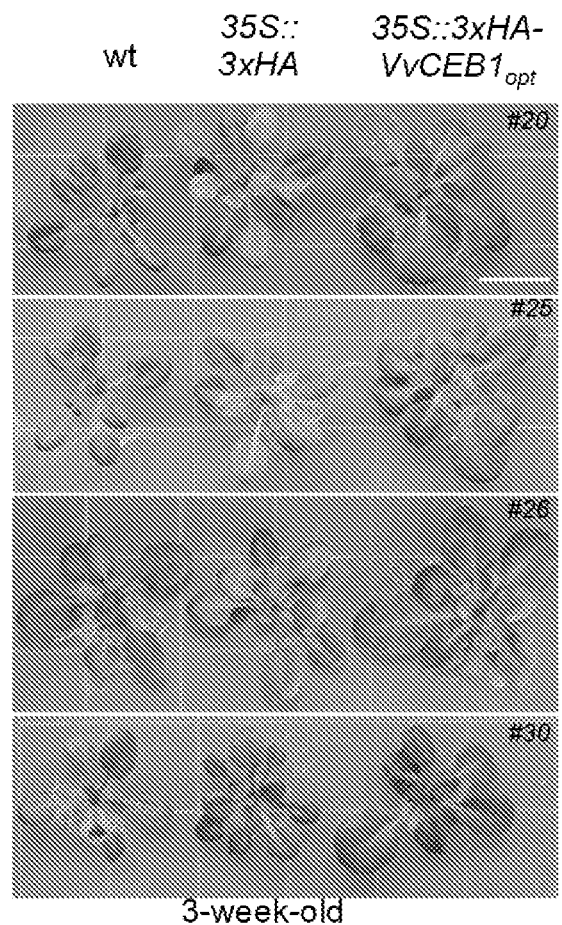
Figure 6H:
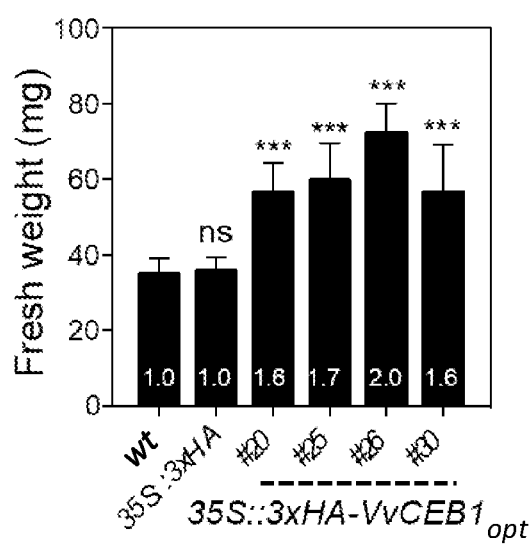
Figure 6I:
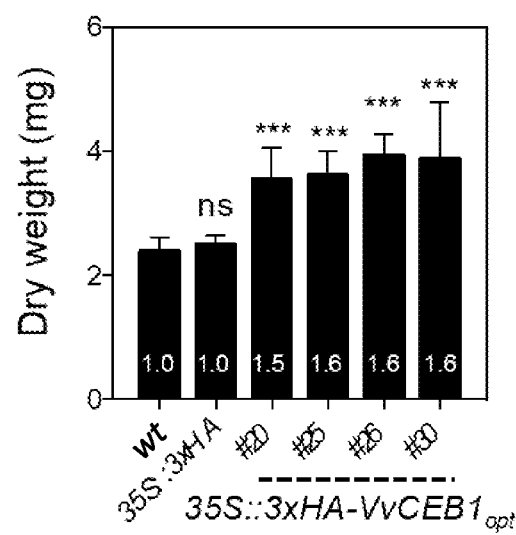

FIGS. 4A-4I illustrate that VvCEB1$_{opt}$-overexpression was found to increase biomass in *Arabidopsis*. Seedling images (1-week-old) of VvCEB1opt-overexpressing line (#26) and the 35S::3×HAempty-vector control line are shown in FIG. 4A. Leaf and rosette images (4-week-old) of VvCEB1opt-overexpressing line (#26) and the 35S::3× HAempty-vector control line are shown in FIG. 4B. Scale bar, 5 cm. A comparison of leaf number (n=15) is provided in FIG. 4C. Leaf area of fifth leaf (n=10) is shown in FIG. 4D. Leaf fresh weight (n=12) is summarized in FIG. 4E and Leaf dry weight (n=12) in FIG. 4F. Rosette diameter (n=20) is provided in FIG. 4G, Rosette fresh weight (n=12) in 4H and Rosette dry weight (n=12) in 4I. For studies shown in 4A-I, seeds of four independent 35S::3×HA-VvCEB1optlines (#20, #25, #26, and #30), Col-0 wild-type (wt), and the 35S::3×HA(empty-vector control) line were germinated and grown in soil mix for 4 weeks under a 16-h photoperiod. Values represent means±s.d., ns=non-significant, ***$p<0.001$ using a one-way ANOVA with Dunnett's multiple comparison test. In summary, the VvCEB1opt-overexpression showed significant increases in leaf number, leaf size, and rosette size in transgenic plants of *Arabidopsis* under soil-grown condition FIGS. 5A-5E illustrate VvCEB1$_{opt}$-overexpressing *Arabidopsis* plants exhibit increased leaf teeth number and modulate serration along the leaf margin. (FIGS. 5A to 5D) Seeds of the VvCEB1$_{opt}$-overexpressing lines (#20, #25, #26, and #30), Col-0 wild-type (wt), and the 35S:: 3×HA empty-vector control were germinated and grown in soil mix for 4 weeks under a 12-h photoperiod. Representative images of fifth leaves of VvCEB1$_{opt}$-overexpressing line and the 35S:: 3×HA empty-vector control line are shown in FIG. 5A (Scale bar, 1 cm). Quantification of teeth number per leaf (n=12) is provided in FIG. 5B. Confocal laser scanning images of 1st leaf teeth from petiole are provided in FIG. 5C. Fifth leaves of four-week-old plants were stained with propidium iodide (PI). Scale bar, 100 µm. Quantification of leaf teeth height/length ratio (n=14) is provided in FIG. 5D. Relative auxin content of inflorescence, leaf, and root tissues of the VvCEB1$_{opt}$-overexpressing line (#26) and Col-0 wild-type (wt), and the 35S:: 3×HA empty-vector control lines (n=4 replicates) are provided in 5E. Values represents means±s.d., ns=non-significant, *$p<0.05$, * *$p<0.01$, and ***$p<0.001$, One-way ANOVA with Dunnett's multiple comparison test. In summary, the VvCEB1$_{opt}$-overexpression showed significant increases in leaf teeth number and height in transgenic plants of *Arabidopsis*.

FIGS. 6A-6I illustrate VvCEB1$_{opt}$ overexpression in *Arabidopsis* increases biomass. (FIGS. 6A to 6C) Seeds were germinated and grown on MS agar medium for 7 days for quantification of the seedling biomass. (FIG. 6A) Representative images of one-week-old seedlings of VvCEB1$_{opt}$-overexpressing lines, and the Col-0 wild type, and the 35S:: 3×HA empty-vector control lines. Scale bar, 1 cm. (FIG. 6B) Quantification of fresh weight of 30 seedlings (n=3 replicates). (FIG. 6C) Dry weight of 30 seedlings (n=3 replicates). (FIGS. 6D to 6F) Seeds were germinated and grown on MS agar medium for 2 weeks for quantification of shoot biomass. (FIG. 6D) Representative images of two-week-old seedlings of four independent VvCEB1$_{opt}$-overexpressing lines, Col-0 wild type, and the 35S:: 3×HA empty-vector control line. Scale bar, 1 cm. (FIG. 6E) Quantification of fresh weight of 10 seedlings (n=3 replicates). (FIG. 6F) Dry weight of 10 seedlings (n=3 replicates). (FIGS. 6G to 6I) Seeds were germinated and grown on MS agar medium for 3 weeks for quantification of plant biomass. (FIG. 6G) Representative images of three-week-old seedlings of four independent VvCEB1$_{opt}$-overexpressing lines, Col-0 wild type, and the 35S:: 3×HA empty-vector control line. Scale bar, 1 cm. (FIG. 6H) Quantification of fresh weight per plant (n=10). (FIG. 6I) Dry weight of three-week-old seedlings (n=10). Values represent means±s.d., ns=non-significant, ***$p<0.001$, One-way ANOVA with Dunnett's multiple comparison test. In summary, the VvCEB1$_{opt}$-overexpression resulted in a significant increase in plant biomass under MS medium-grown condition.

Figure 7A:
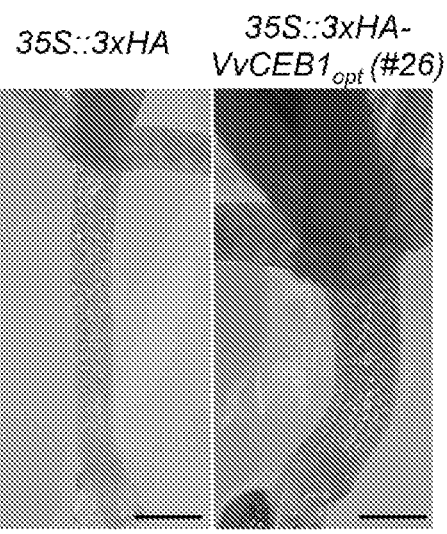
FIGS. 7A-7C illustrate VvCEB1$_{opt}$ overexpression increases hypocotyl thickness in *Arabidopsis*.
Figure 7B:
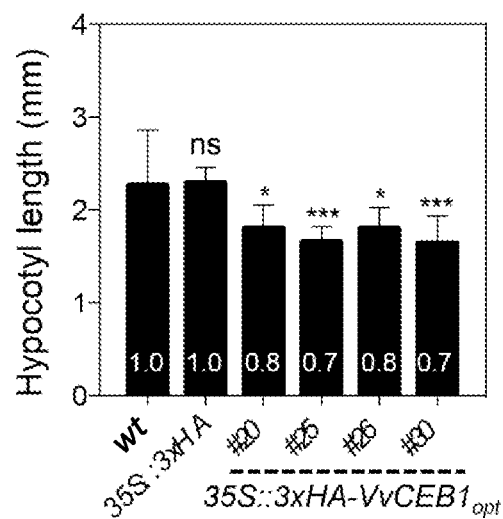
Figure 7C:
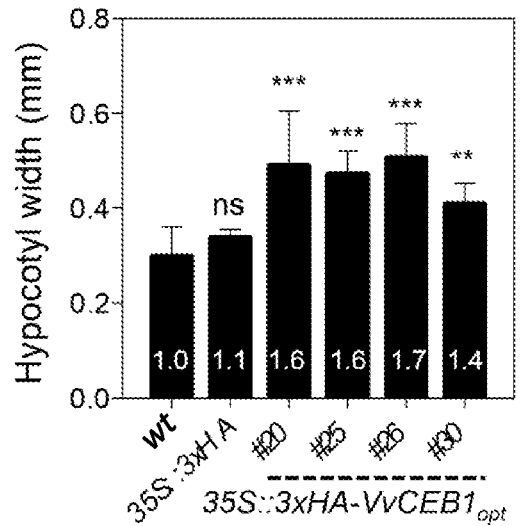

FIGS. 7A-7C illustrate VvCEB1$_{opt}$ overexpression increases hypocotyl thickness in *Arabidopsis*. Seeds of four VvCEB1$_{opt}$-overexpressing lines, Col-0 wild-type, and the 35S:: 3×HA empty-vector control line were germinated and grown vertically on half-strength Murashige and Skoog (MS) agar medium for 14 days under a 16-h photoperiod. Images of hypocotyls from VvCEB1$_{opt}$-overexpressing line (#26) and the 35S:: 3×HA empty-vector control are provided in FIG. 7A. Scale bar, 0.5 mm. Comparison of hypocotyl length (n=10) is provided in FIG. 7B and hypocotyl width (n=10) in FIG. 7C. Values represent means±s.d., ns=non-significant, *$p<0.05$, * *$p<0.01$, and ***$p<0.001$, One-way ANOVA with Dunnett's multiple comparison test. In summary, the VvCEB1$_{opt}$-overexpression showed significant increases in hypocotyl thickness.

Figure 8D:
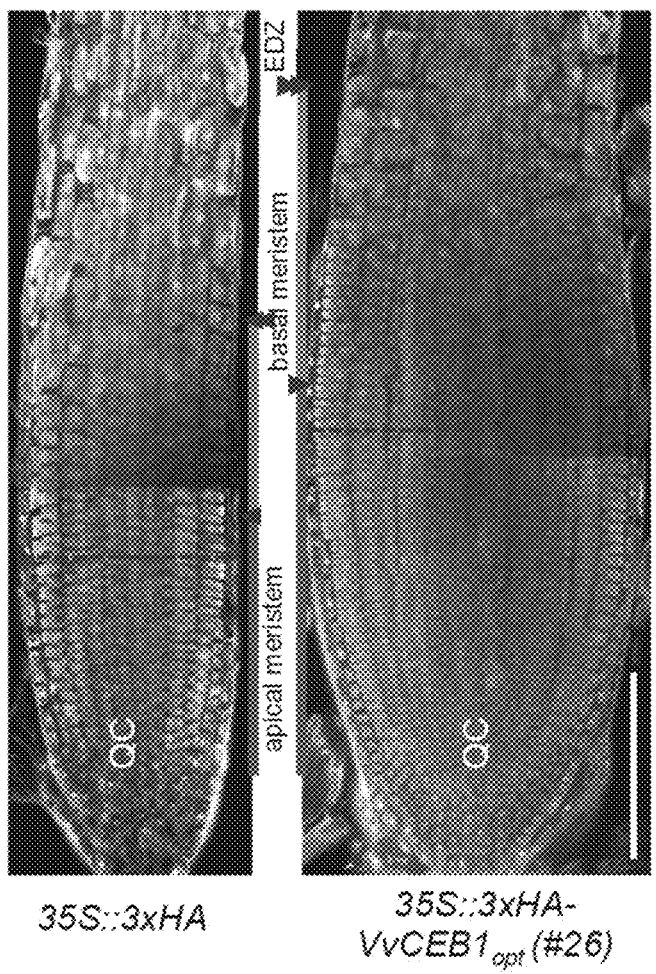
FIGS. 8A-8N illustrate VvCEB1$_{opt}$ overexpression increases root size, number, and biomass in *Arabidopsis*.
Figure 8E:
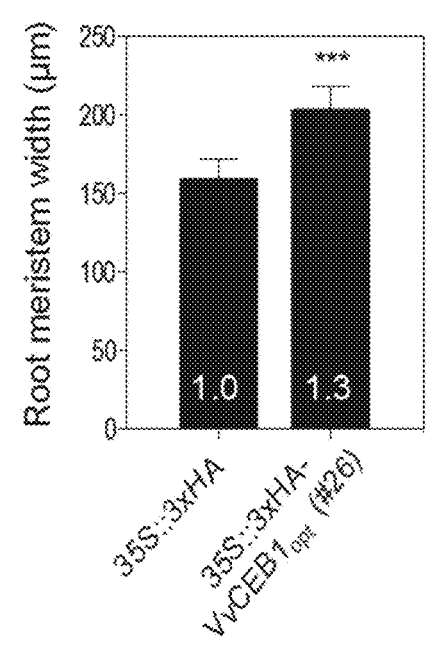
Figures 8F, 8G, 8H, 8I, 8J, 8K, 8L, 8M, 8N:
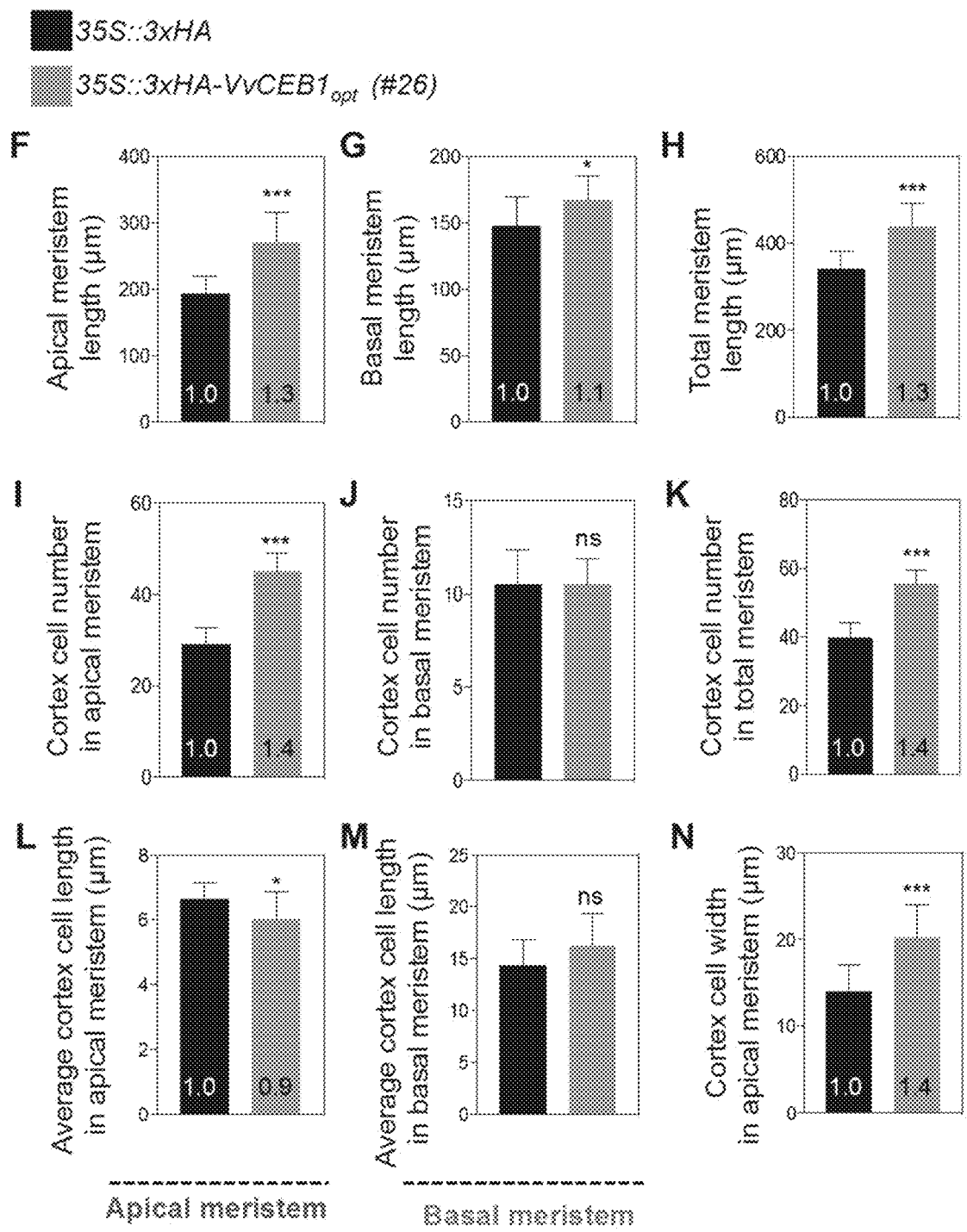

FIGS. 8A-8N illustrate VvCEB1$_{opt}$ overexpression increases root biomass in *Arabidopsis*. FIG. 8A provides root images (2-week-old) of VvCEB1$_{opt}$-overexpressing line (#26) and the 35S:: 3×HA empty-vector control line. Scale bar, 1 cm. FIG. 8B provides comparison of primary root length (n=30) and FIG. 8C lateral root number (n=30). FIG. 8D provides confocal laser scanning images of root meristem cells of VvCEB1$_{opt}$-overexpressing line (#26) and the 35S:: 3×HA empty-vector control. Two-week-old roots were double-stained with FM4-64 and PI. Broken lines indicate root meristem widths. Lines represent the lengths of the apical meristem, the basal meristem, and the elongation/differentiation zone. Single and double arrowheads indicate the borders of the apical meristem and basal meristem, respectively. QC indicates the quiescent center. Scale bar, 150 µm. (FIG. 8E) Comparison of root meristem width (n=16). (FIGS. 8F to 8H) Quantification of the length of root meristem (n=12). (FIG. 8F), Apical meristem. (FIG. 8G), Basal meristem length. (FIG. 8H) Total meristem length. FIGS. 8I to 8K provide the quantification of cortical meristem cell number (n=12). Cortical cell number in apical meristem zone is shown in FIG. 8I. FIG. 8J provides the cortical cell number in basal meristem zone. FIG. 8K provides total cortical cell number. FIGS. 8L and 8M illustrate the average cortical cell number in apical meristem zone (FIG. 8L) and basal meristem zone (FIG. 8M) (n=12). FIG. 8N provides the cortical cell width in apical meristem zone (n=120). Seeds of four independent 35S:: 3×HA-VvCEB1$_{opt}$ lines (#20, #25, #26, and #30), Col-0 wild-type (wt), and the 35S:: 3×HA line were germinated and grown on half-strength MS agar medium for 14 days under a 16-h photoperiod (16 hours of light per day). Values represent means±s.d., ns=non-significant, *p<0.05, * *p<0.01, and ***p<0.001, One-way ANOVA with Dunnett's multiple comparison test (FIGS. 8B and 8C) and Student's t-test (FIGS. 8E to 8N). In summary, the VvCEB1$_{opt}$-overexpression showed significant increases in root length, lateral root number, and root meristem number, and root meristem size of transgenic plants of Arabidopsis.

Figure 9A:
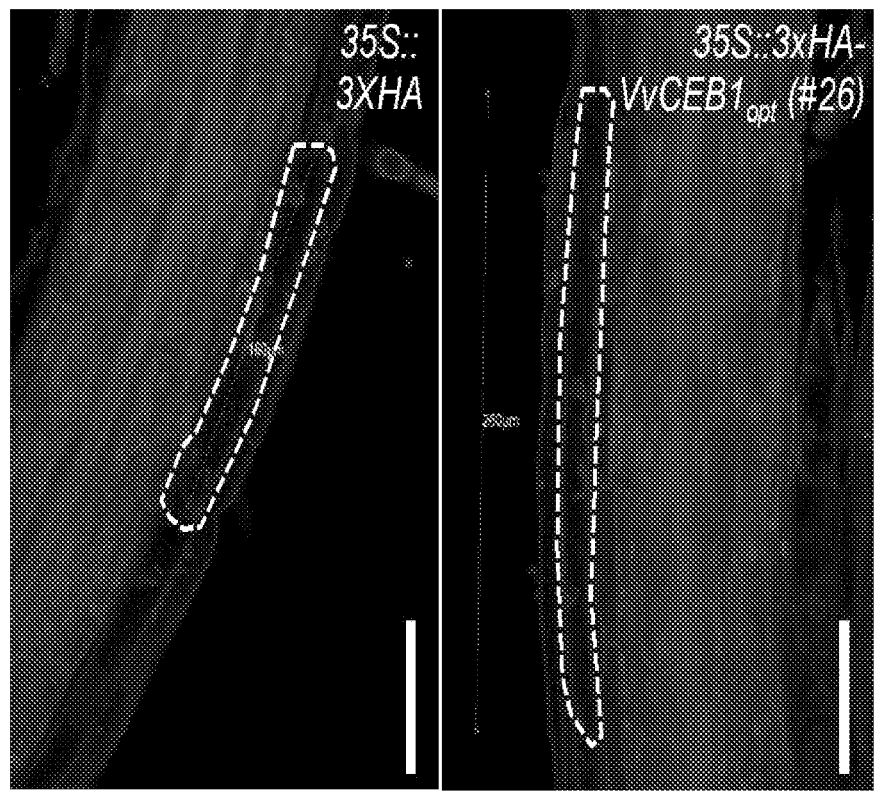
FIGS. 9A-9D illustrate VvCEB1$_{opt}$-overexpression in *Arabidopsis* plants affects root cell size in the mature zone of the root.
Figure 9B:
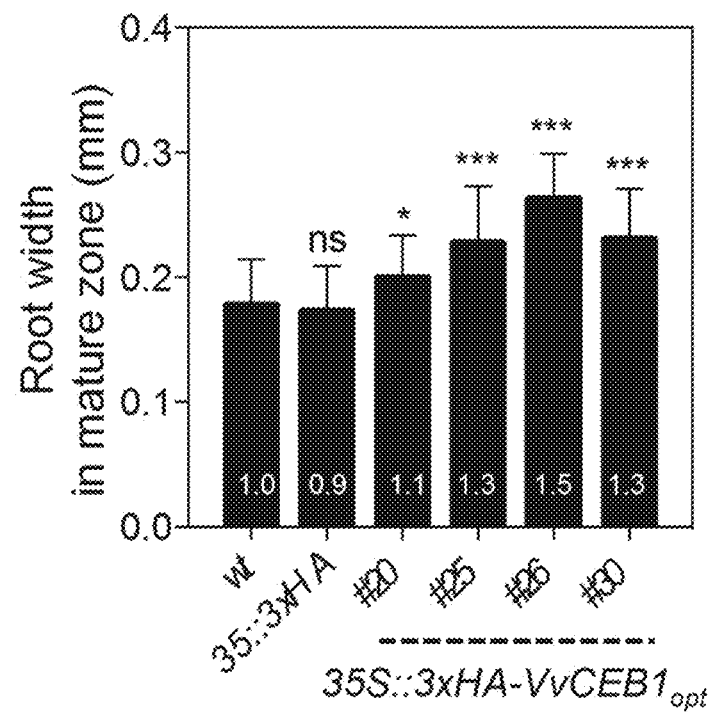
Figure 9C:
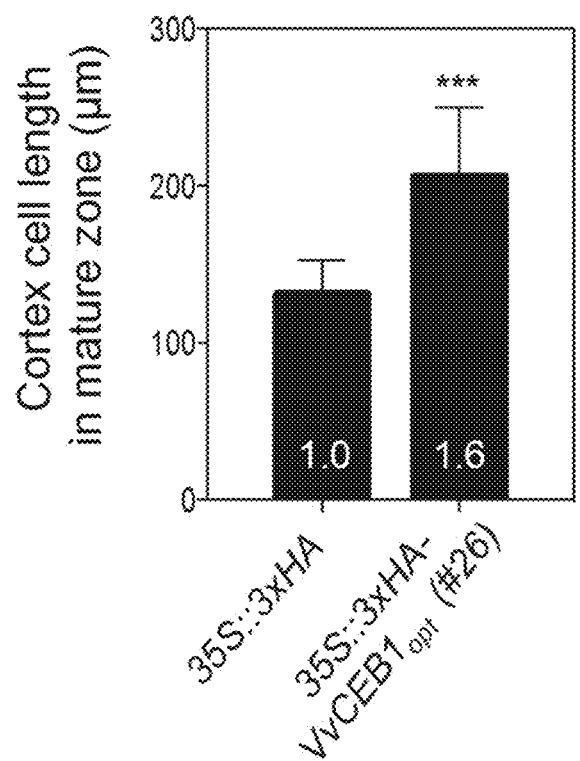
Figure 9D:
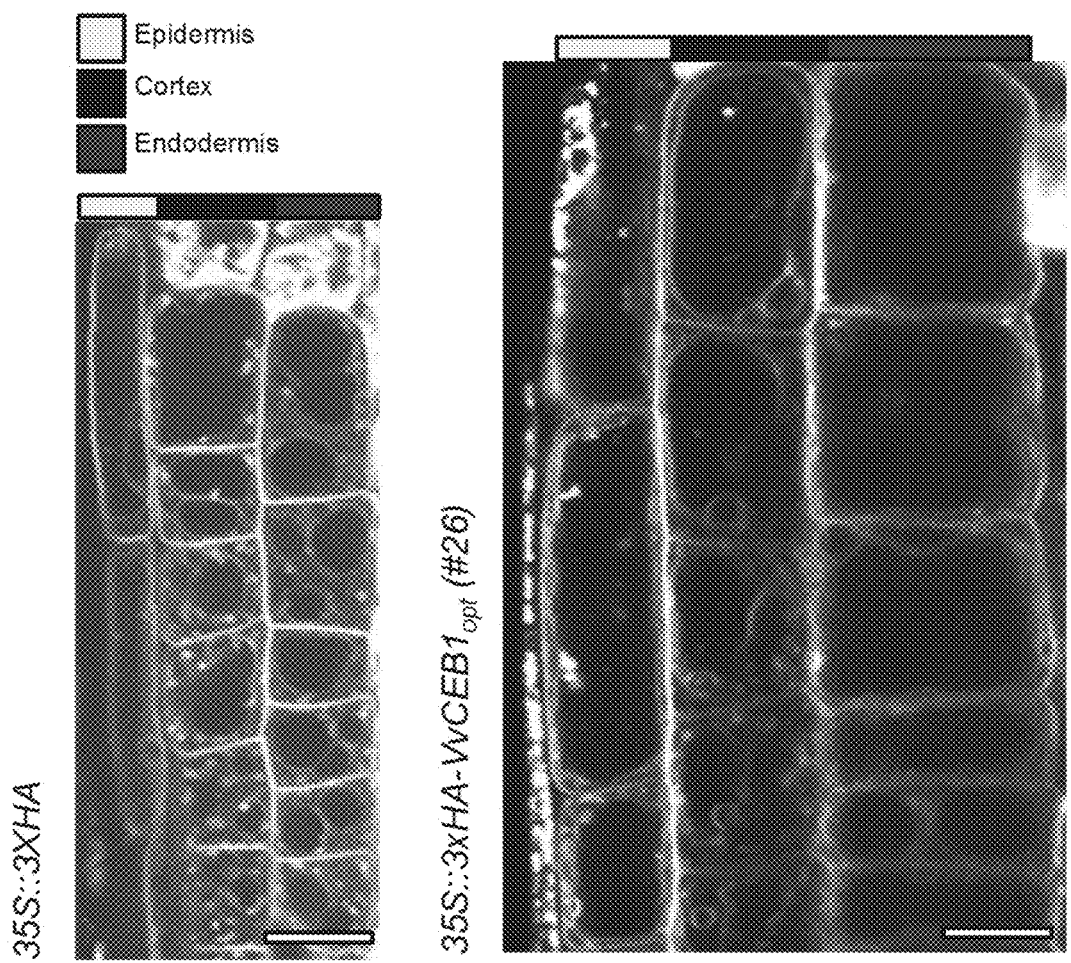

FIGS. 9A-9D illustrate VvCEB1$_{opt}$-overexpression in Arabidopsis plants affects root cell size in root mature zone. Seeds of the VvCEB1$_{opt}$-overexpressing lines, Col-0 wild-type (wt), and the 35S:: 3×HA empty-vector control line were germinated and grown vertically on half-strength MS agar medium for 14 days under a 16-h photoperiod (16 hours of light per day). Confocal laser scanning images of root cells stained with FM4-64 (2 h) and PI in mature zone are provided in FIG. 9A. White broken lines indicate the outlines of representative cortical cells. Scale bar, 60 µm. FIG. 9B illustrates quantification of primary root width in the maturation zone (n=30) and FIG. 9C quantification of cortical root cell length in mature zone (n=60). Images of cells and vacuoles in basal meristem zone stained with FM4-64 (5 h) captured by confocal laser scanning microscopy are provided in 9D. Lines indicate the epidermis, cortex, and endodermis. Scale bar, 10 µm. Values represent means±s.d., ns=non-significant, *p<0.05, and ***p<0.001, One-way ANOVA with Dunnett's multiple comparison test (FIG. 9B) and Student's t-test (FIG. 9C). In summary, the VvCEB1$_{opt}$-overexpression showed significant increases in cell size and vacuole size in root mature zone of transgenic Arabidopsis.

Figure 10A:
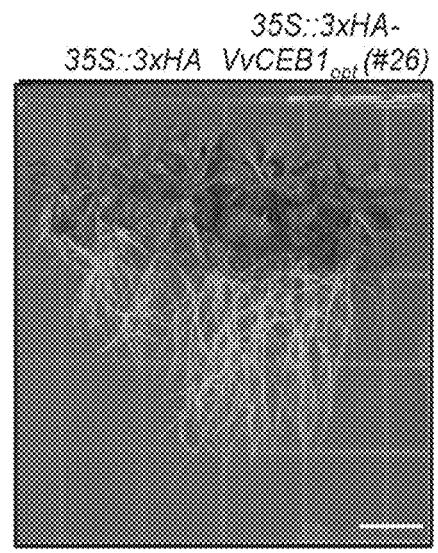
FIGS. 10A-10C illustrate VvCEB1$_{opt}$-overexpressing *Arabidopsis* plants exhibit increased root biomass.
Figure 10B:
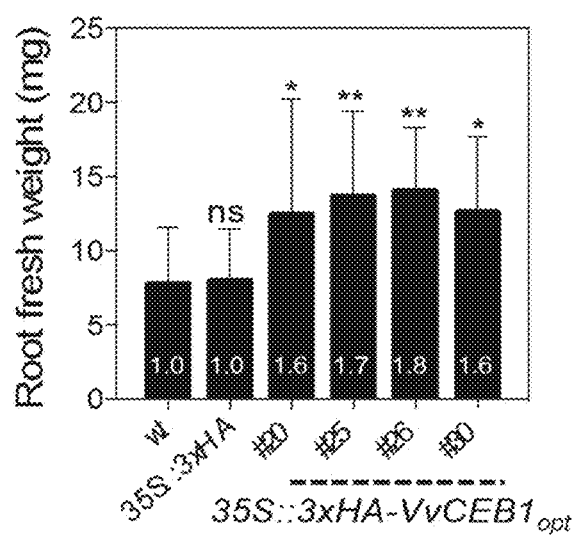
Figure 10C:
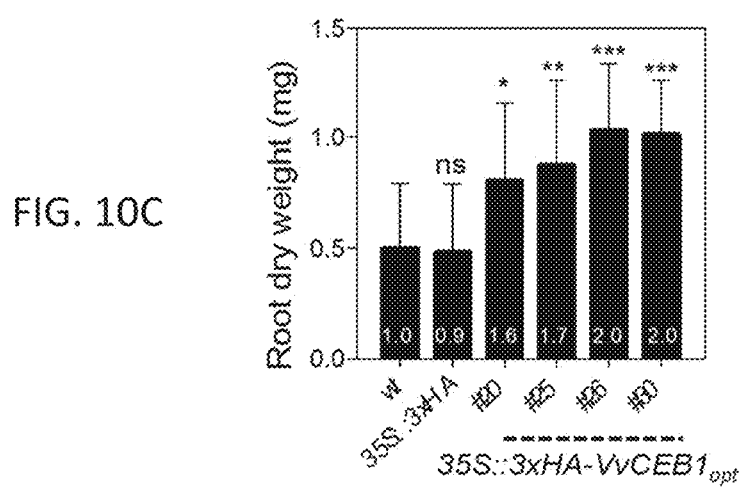

FIGS. 10A-10C illustrate VvCEB1$_{opt}$-overexpressing Arabidopsis plants exhibit increased root biomass. FIG. 10A illustrates seedlings were grown vertically on half-strength MS medium for 3 weeks under a 16-h photoperiod (16 hours of light per day). Representative images of root biomass of 35S:: 3×HA-VvCEB1$_{opt}$ line (#26), and the 35S:: 3×HA empty-vector control line. Scale bar, 1 cm. FIG. 10B shows the quantification of root fresh weight of three-week-old seedlings (n=20). FIG. 10C illustrates root dry weight of three-week-old seedlings (n=20). Values represent means±s.d., ns=non-significant, *p<0.05, * *p<0.01, and ***p<0.001, One-way ANOVA with Dunnett's multiple comparison test. In summary, the VvCEB1$_{opt}$-overexpression results in plant with a significant increase in fresh and dry weight of roots of transgenic Arabidopsis.

Figure 11A:
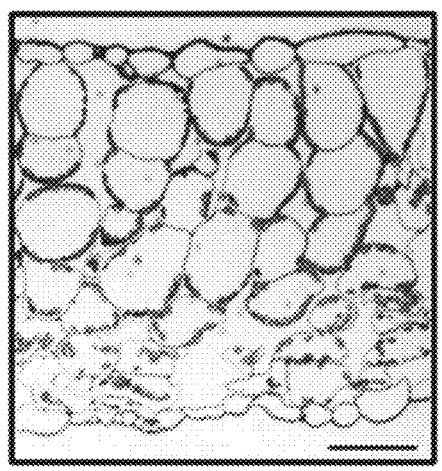
FIGS. 11A-11F illustrate VvCEB1$_{opt}$ overexpression increases leaf succulence in *Arabidopsis*.
Figure 11A:
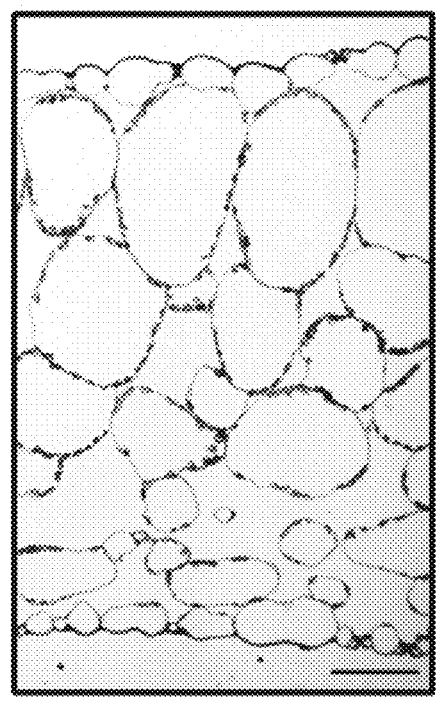
Figure 11B:
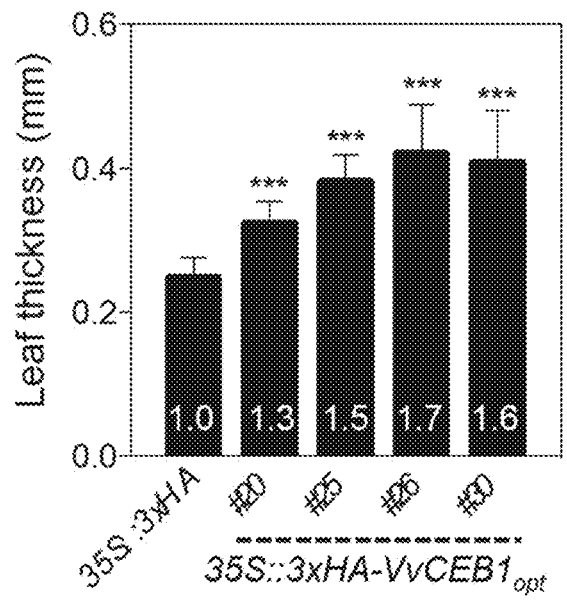
Figure 11C:
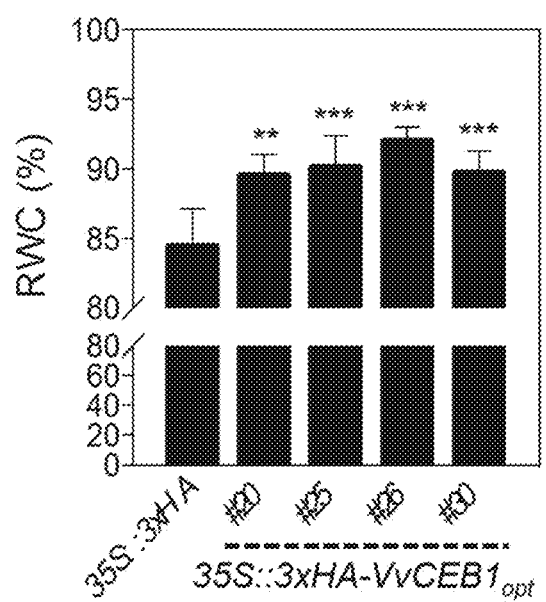
Figure 11D:
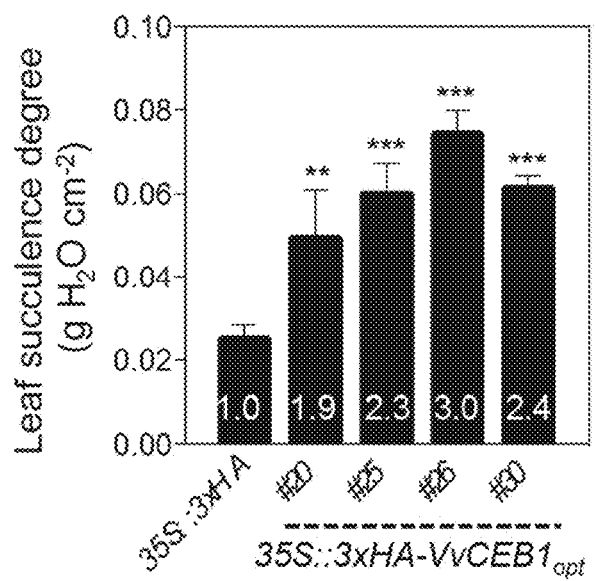
Figure 11E:
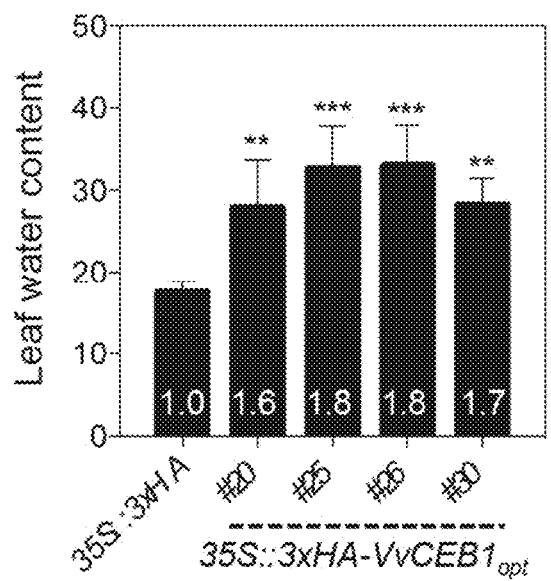
Figure 11F:
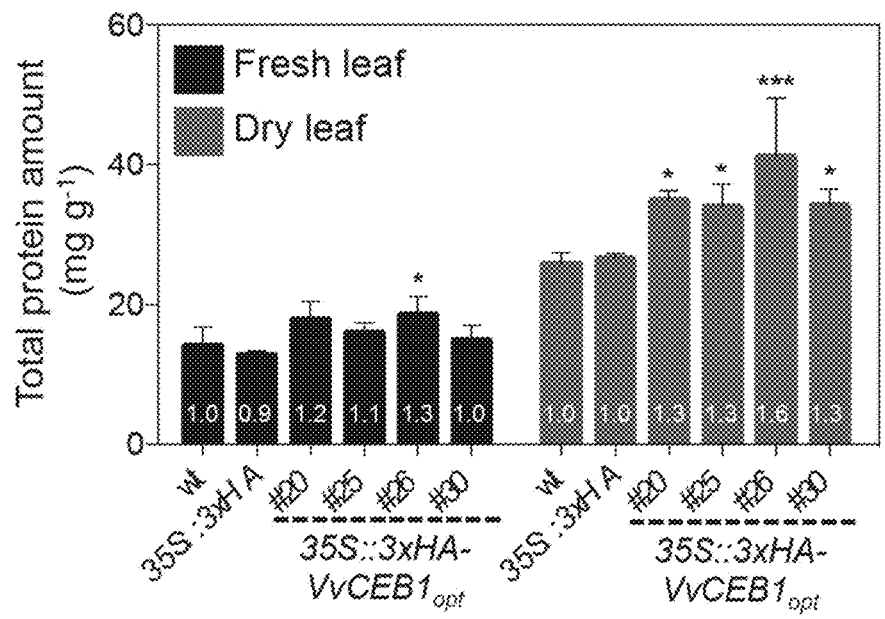

FIGS. 11A-11F illustrate VvCEB1$_{opt}$ overexpression increases leaf succulence in Arabidopsis. Transverse sections of leaves from a VvCEB1$_{opt}$-overexpressing line (#26) and the 35S:: 3×HA empty-vector control are shown in FIG. 11A. Scale bar, 100 µm. FIG. 11B shows mean leaf thickness (n=30), FIG. 11C illustrates a comparison of relative water content (RWC) of four fifth leaves (n=5 replicates), FIG. 11D shows succulence degree measured as saturated water content of four fifth leaves per unit area (n=5 replicates) and FIG. 11E illustrates water content measured as leaf succulence index of four fifth leaves (n=5 replicates). FIG. 11F illustrates the quantification of total protein amount of fifth leaves (n=4 replicates). Seedlings of four independent VvCEB1$_{opt}$-overexpressing lines (#20, #25, #26, and #30), Col-0 wild-type (wt), and the 35S:: 3×HA (empty-vector control) line were grown in soil mix for 4 weeks under a 12-h photoperiod. Values represent means±s.d., ns=non-significant, *p<0.05, * *p<0.01, and ***p<0.001 using a one-way ANOVA with Dunnett's multiple comparison test. In summary, the VvCEB1$_{opt}$-overexpression results in plant leaves with higher water content than control plants, a significant increase in leaf thickness, relative water content, leaf succulence, and leaf total protein amount of transgenic Arabidopsis.

Figure 12A:
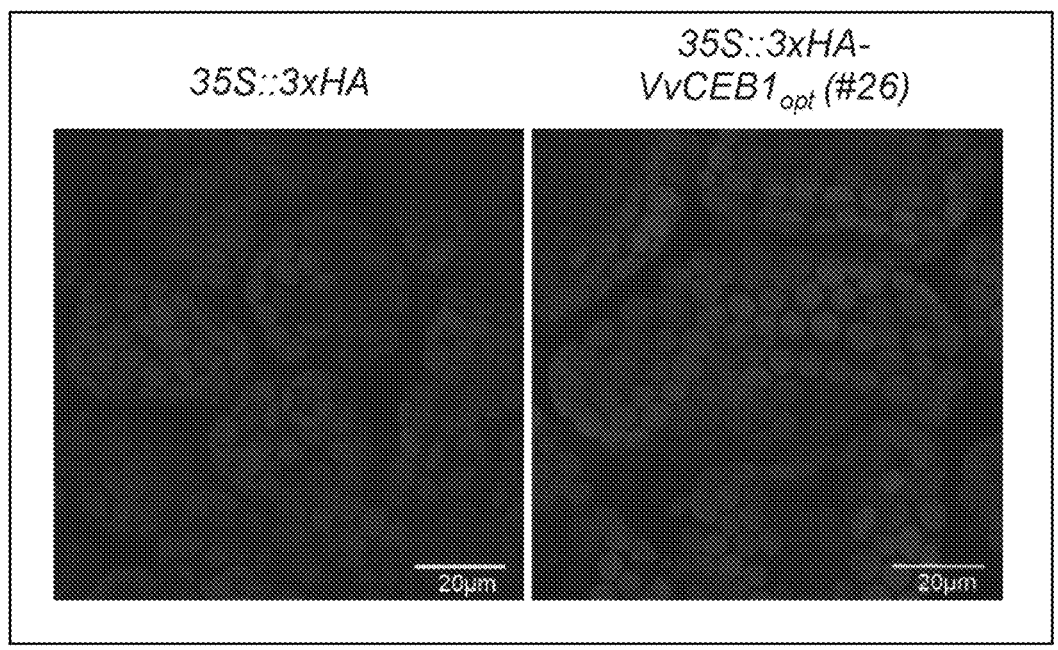
FIGS. 12A-12G illustrate VvCEB1$_{opt}$ overexpression increases cell size and intercellular air space in *Arabidopsis*.
Figure 12B:
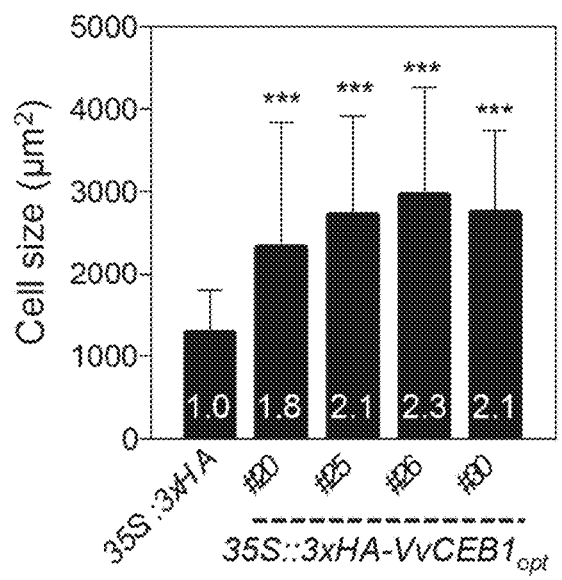
Figure 12C:
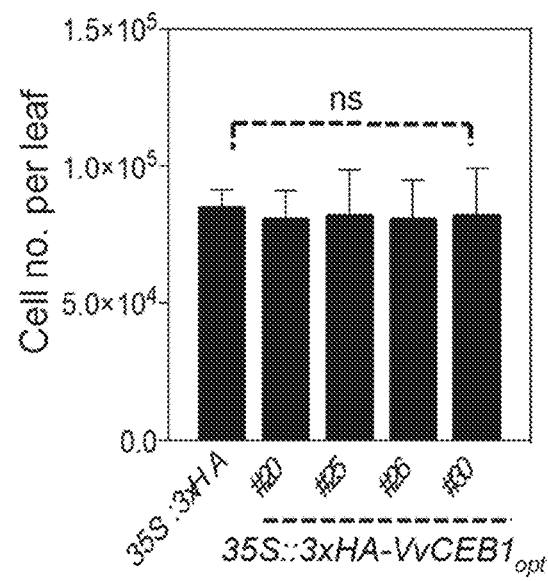
Figure 12D:
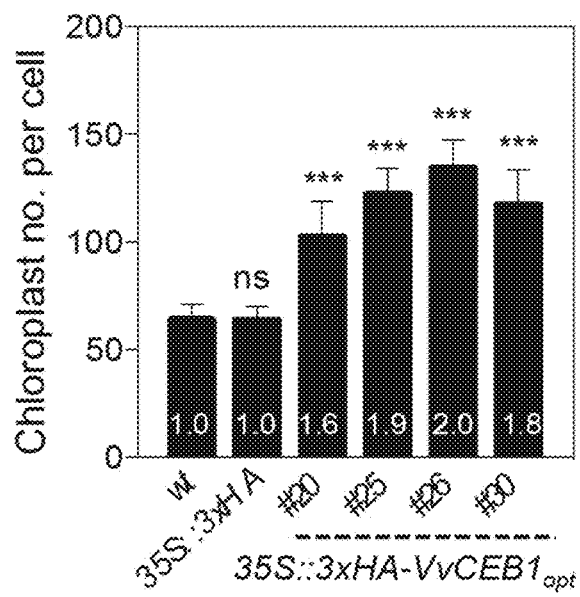
Figure 12F:
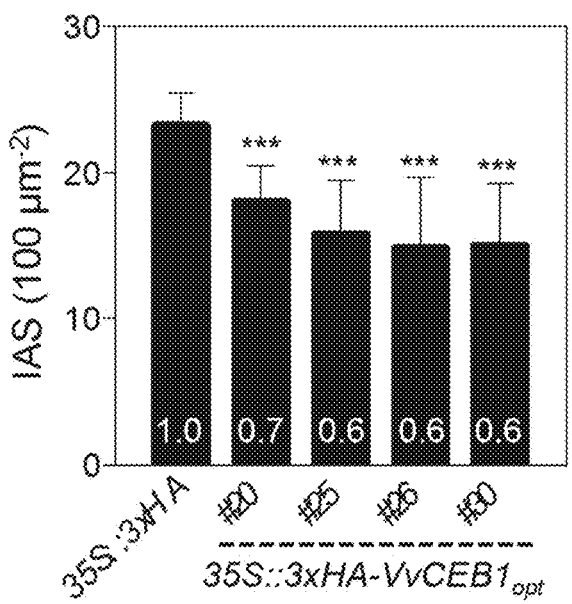
Figure 12G:
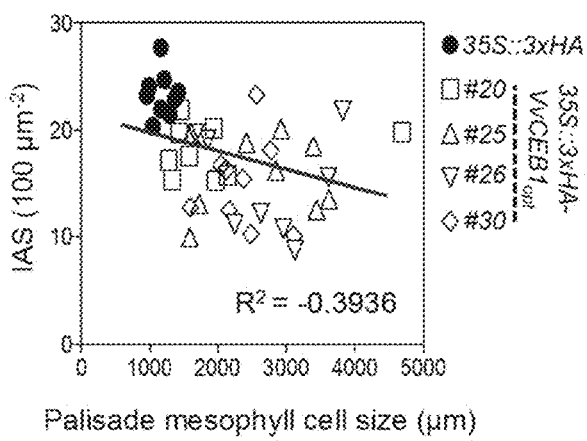
Figure 12E:
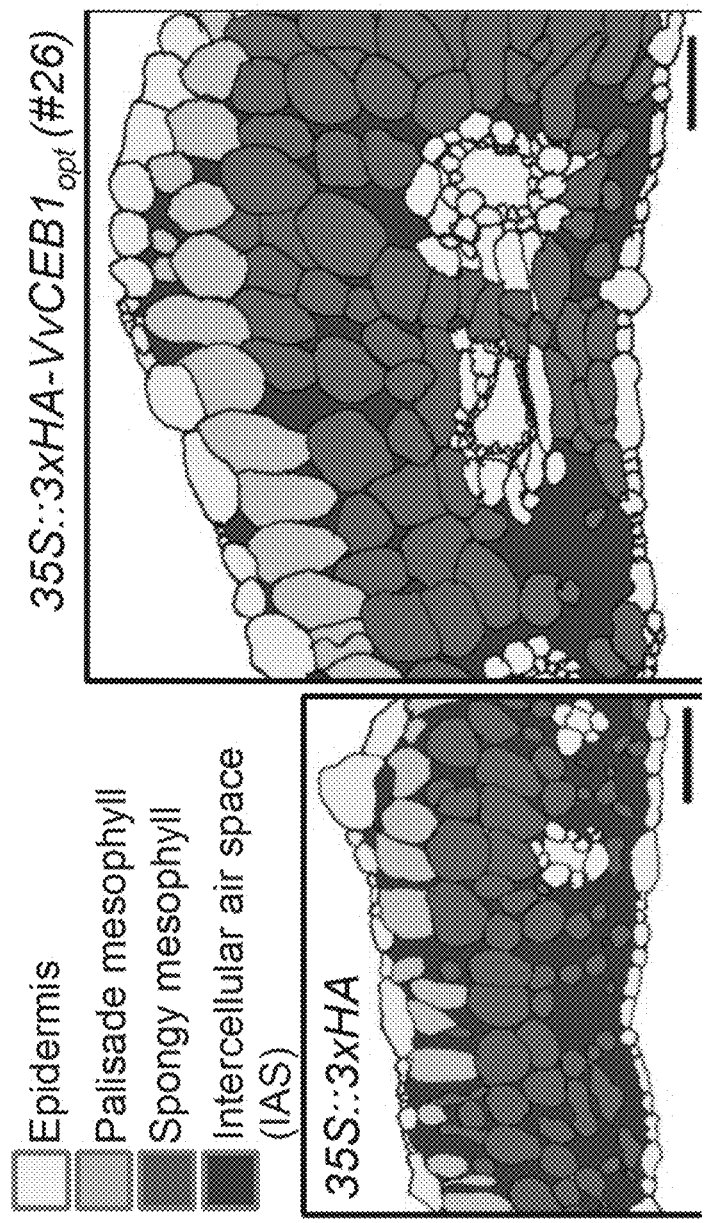

FIGS. 12A-12G illustrate VvCEB1$_{opt}$ overexpression increases cell size and intercellular air space in Arabidopsis. FIG. 12A provides confocal laser scanning images of palisade mesophyll cells and chloroplasts of VvCEB1$_{opt}$-overexpressing line (#26) and the 35S:: 3×HA empty-vector control. Scale bar, 20 µm. FIG. 12B illustrates the quantification of the area of palisade mesophyll cells (n=110). FIG. 12C provides the mesophyll cell number per fifth fully expanded leaf (n=10) and FIG. 12D chloroplast number per palisade mesophyll cell (n=30). FIG. 12E provides representative images of intercellular air space (IAS) of VvCEB1$_{opt}$-overexpressing line (#26) and the 35S:: 3×HA empty-vector control. Scale bar, 100 µm. FIG. 12F provides the quantification of IAS (n=9) and FIG. 12G illustrates the correlation between IAS and average size of the palisade mesophyll cells (n=44). Transverse leaf sections were used to draw cell outlines. Seeds of four independent VvCEB1$_{opt}$-overexpressing lines (#20, #25, #26, and #30), Col-0 wild-type (wt), and the 35S:: 3×HA (empty-vector control) line were germinated and grown in soil mix for 4 weeks under a 12-h photoperiod. Values represents means±s.d., ns=non-significant, and ***p<0.001, One-way ANOVA with Dunnett's multiple comparison test. In summary, the VvCEB1$_{opt}$-overexpressing lines showed reduced intercellular air space and increase chloroplast number per palisade mesophyll cell compared with control lines, which were correlate with an increase in cell size.

Figure 13A:
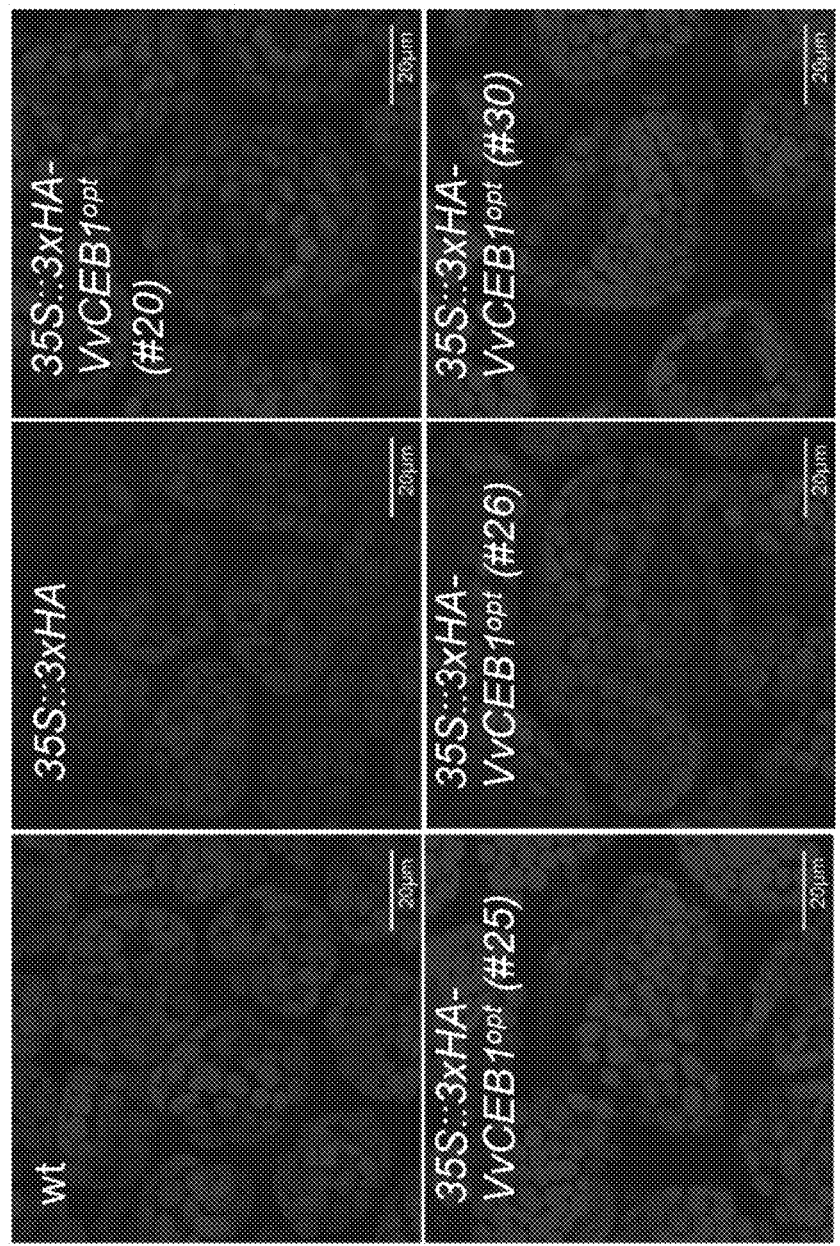
FIGS. 13A-13D illustrate VvCEB1$_{opt}$-overexpressing *Arabidopsis* plants have increased chlorophyll contents.
Figure 13B:
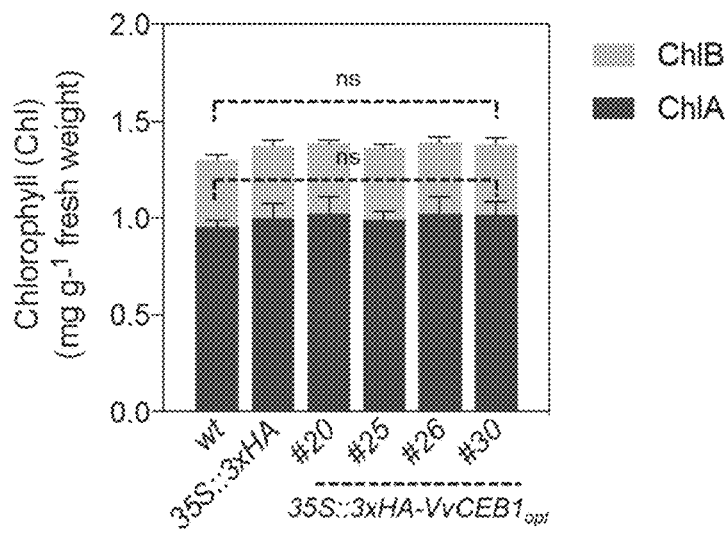
Figure 13C:
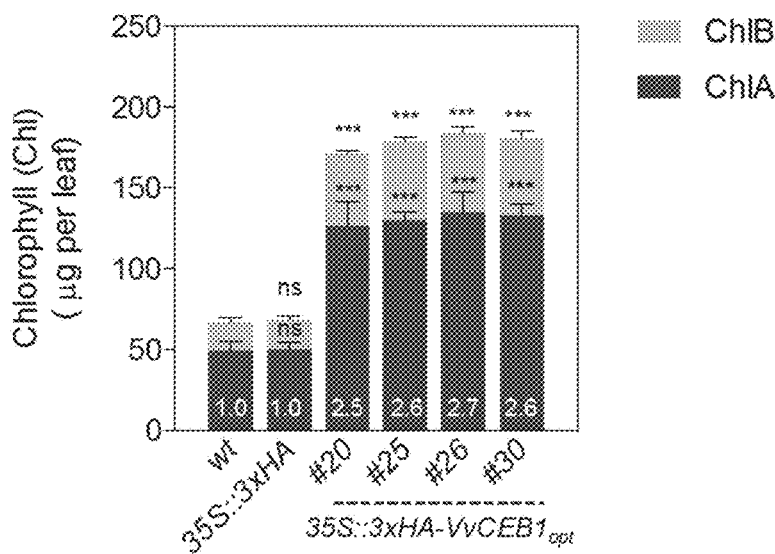
Figure 13D:
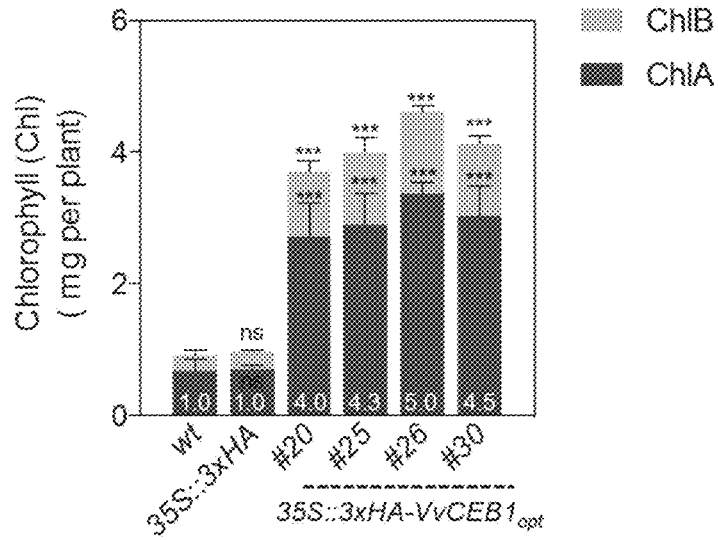

FIGS. 13A-13D illustrate VvCEB1$_{opt}$-overexpressing Arabidopsis plants have increased chlorophyll contents. Seeds of four VvCEB1$_{opt}$-overexpressing lines, wild-type A. thaliana ecotype Col-0, and the 35S:: 3×HA empty-vector control line were germinated and grown in soil mix for 4 weeks under a 12-h photoperiod (12 hours of light per day). FIG. 13A provides confocal laser scanning images of palisade mesophyll cells and chloroplasts of VvCEB1$_{opt}$-overexpressing lines and control lines. Chlorophyll autofluorescence in the leaf palisade mesophyll cells is shown in red. The 3D-projection was generated by combining a Z-stack of images. Scale bar, 20 µm. FIGS. 13B to 13D illustrate results from fifth fully expanded true leaves were sampled and measured for chlorophyll contents (n=4 replicates). FIG. 13B illustrates chlorophyll contents per gram fresh weight, FIG. 13C shows chlorophyll contents per leaf and FIG. 13D illustrates chlorophyll contents per plant. Values represent means±s.d., ns=non-significant, ***p<0.001, One-way ANOVA with Dunnett's multiple comparison test. In summary, the VvCEB1$_{opt}$-overexpressing lines showed increased chlorophyll content.

Figure 14A:
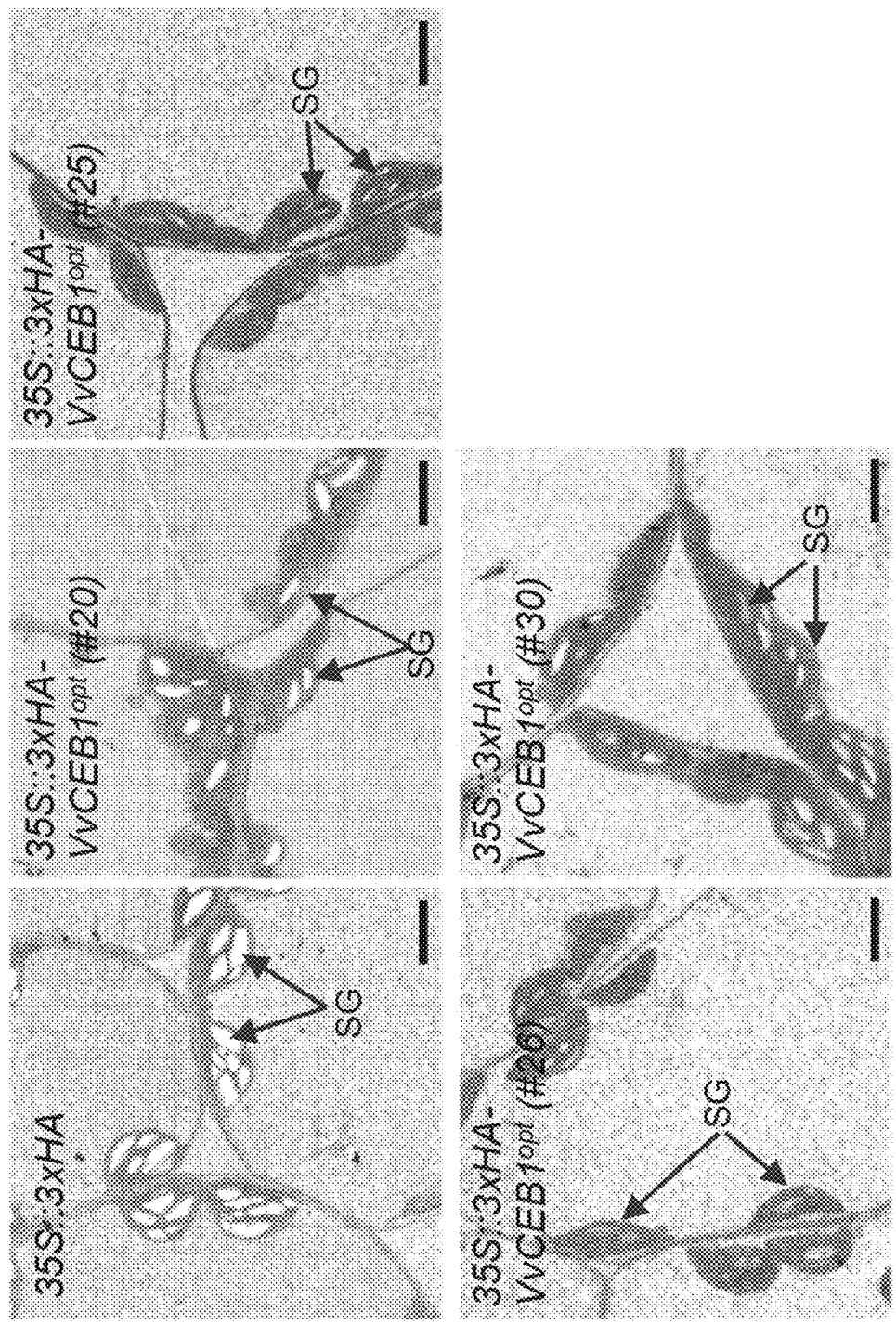
FIGS. 14A-14I illustrate VvCEB1$_{opt}$-overexpressing *Arabidopsis* plants have increased soluble sugar contents.
Figure 14B:
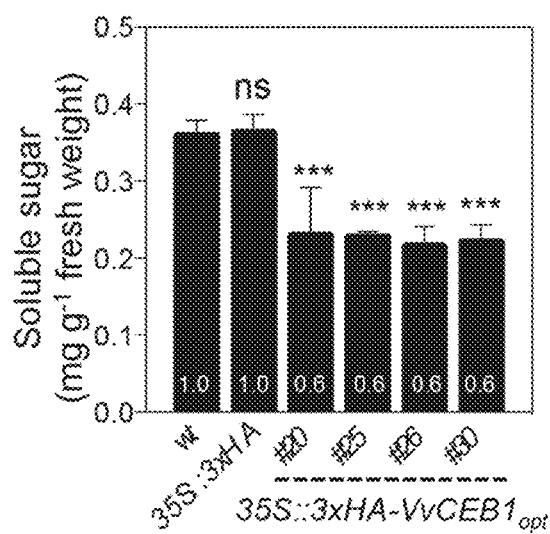
Figure 14C:
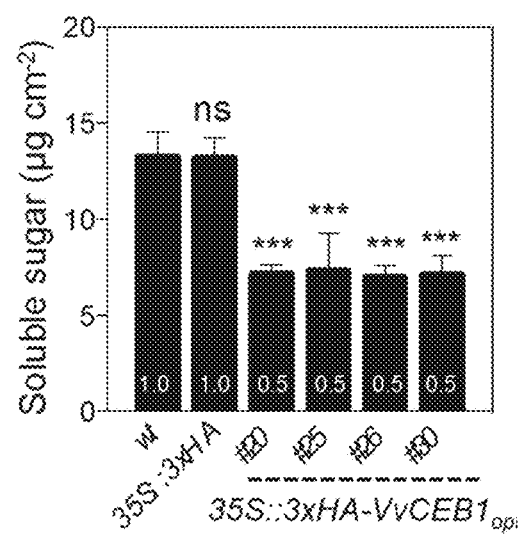
Figure 14D:
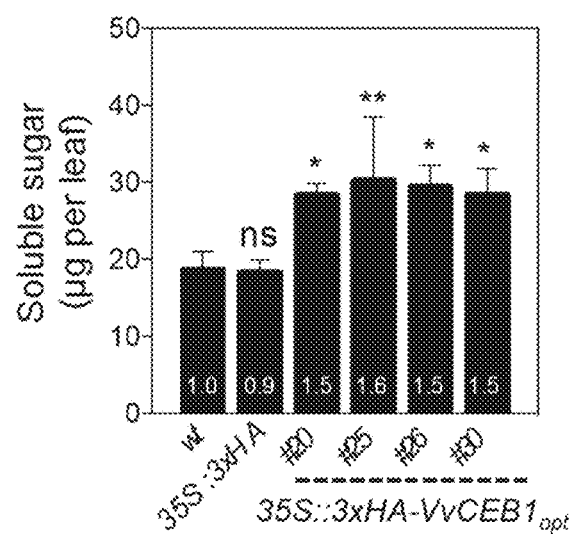
Figure 14E:
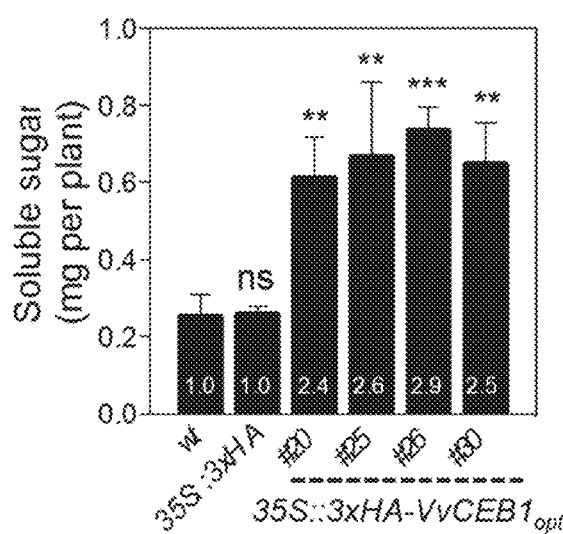
Figure 14F:
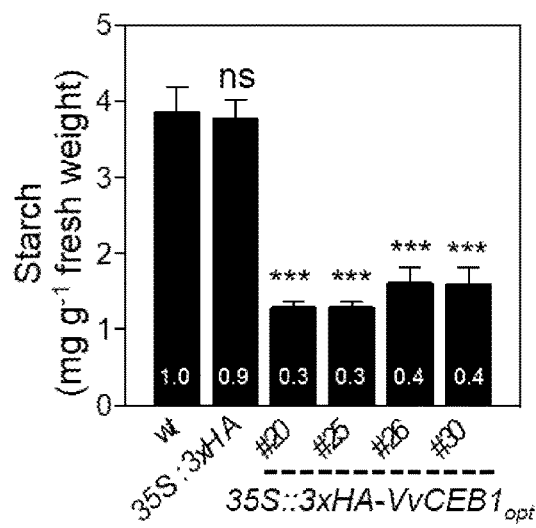
Figure 14G:
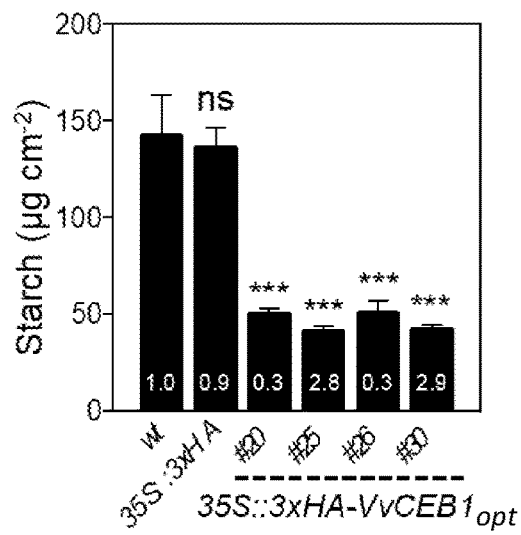
Figure 14H:
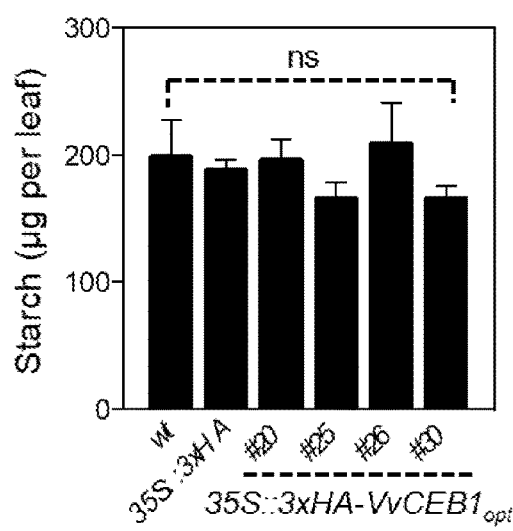
Figure 14I:
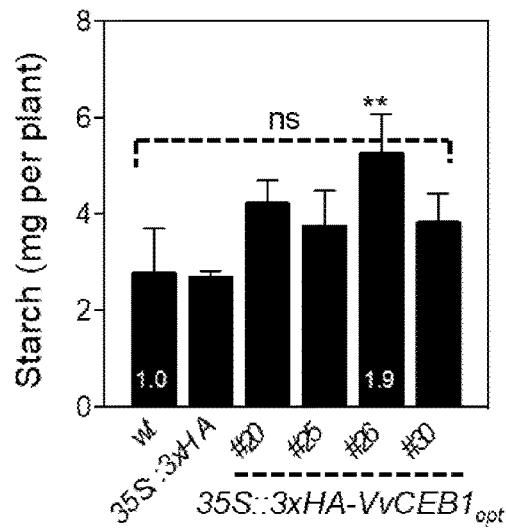

FIGS. 14A-14I illustrate VvCEB1$_{opt}$-overexpressing Arabidopsis plants have increased soluble sugar contents. Seeds of four VvCEB1$_{opt}$-overexpressing lines, wild-type (wt) A. thaliana ecotype Col-0, and the 35S:: 3×HA empty-vector control line were germinated and grown in soilless growth medium for 4 weeks under a 12-h photoperiod. Fifth fully expanded true leaves were sampled at noon for carbohydrate assays. FIG. 14A provides representative images of chloroplasts in VvCEB1opt-overexpressing lines, Col-0 wild type, and 35S:: 3×HA empty-vector control lines. Images were captured by transmission electron microscopy. Arrows indicate starch granules (SG). Scale bar, 5 µm. FIGS. 14B to 14E illustrate soluble sugar contents in leaves (n=4 replicates). FIG. 14B provides the soluble sugar contents per gram fresh weight, FIG. 14C soluble sugar contents per leaf area (cm$^2$), FIG. 14D soluble sugar contents per leaf, and FIG. 14E soluble sugar contents per plant. FIGS. 14F to 14I illustrate starch contents in leaves (n=4 replicates). FIG. 14F provides starch contents per gram fresh weight, FIG. 14G starch contents per unit leaf area (cm$^2$), FIG. 14H starch contents per leaf, and FIG. 14I starch contents per plant. Values represent means±s.d., ns=non-significant, *p<0.05, p<0.01, and *p<0.001, One-way ANOVA with Dunnett's multiple comparison test. In summary, the VvCEB1$_{opt}$-overexpressing lines showed increased soluble sugar content.

Figure 15A:
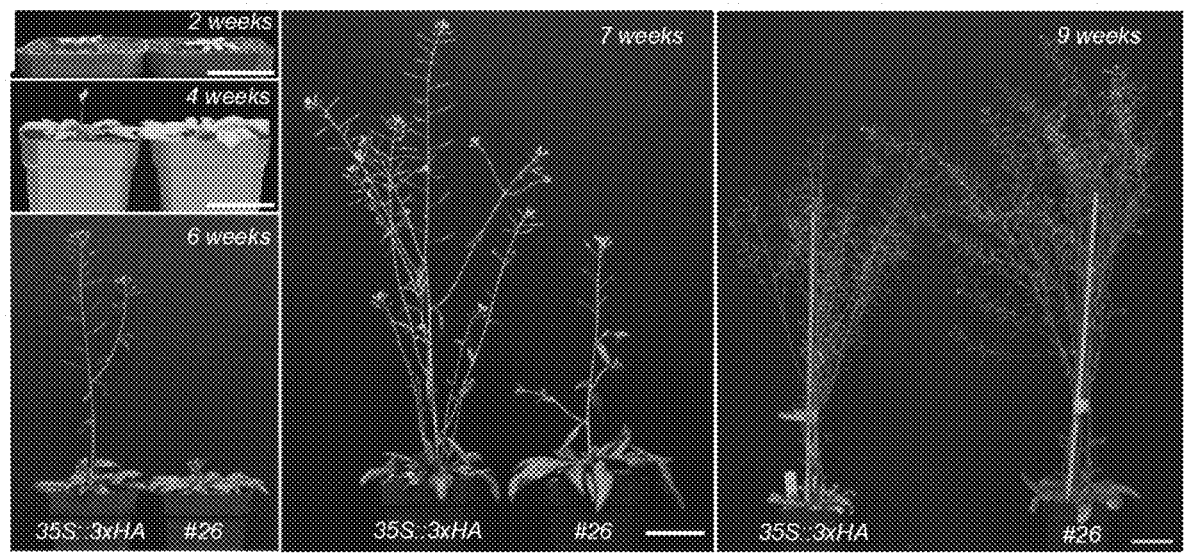
FIGS. 15A-15D illustrate VvCEB1$_{opt}$ overexpression delays flowering and leaf senescence in *Arabidopsis*.
Figure 15B:
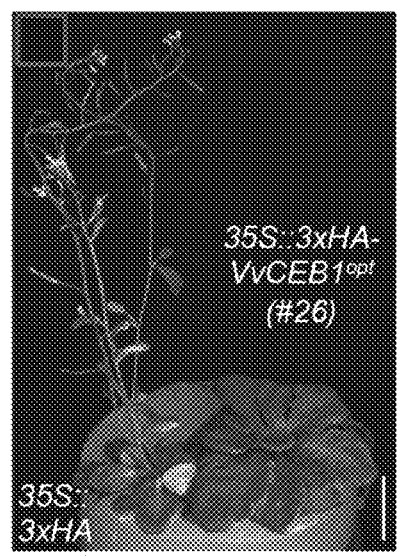
Figure 15C:
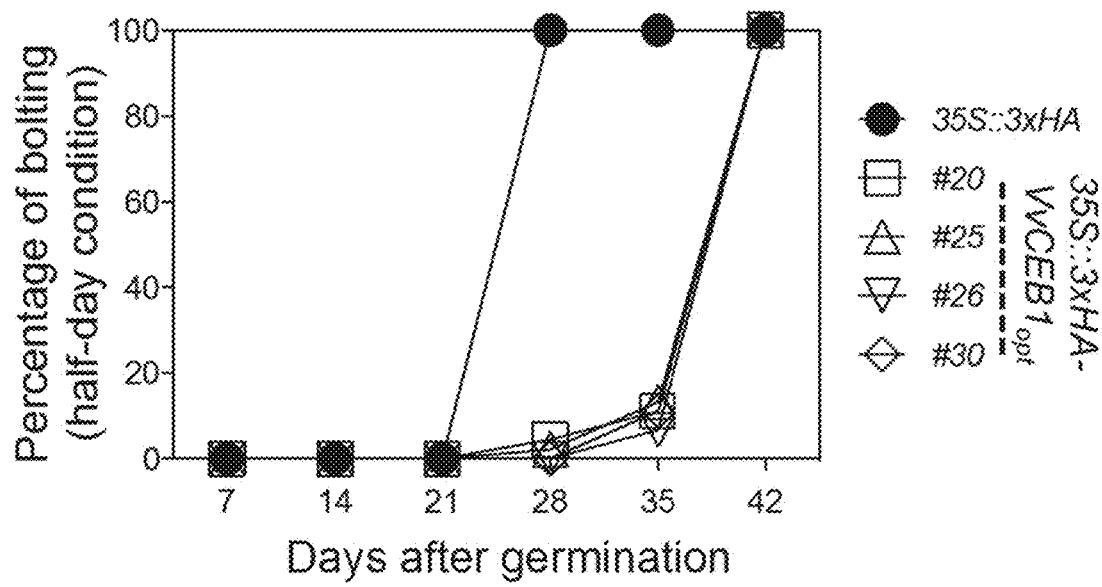
Figure 15D:
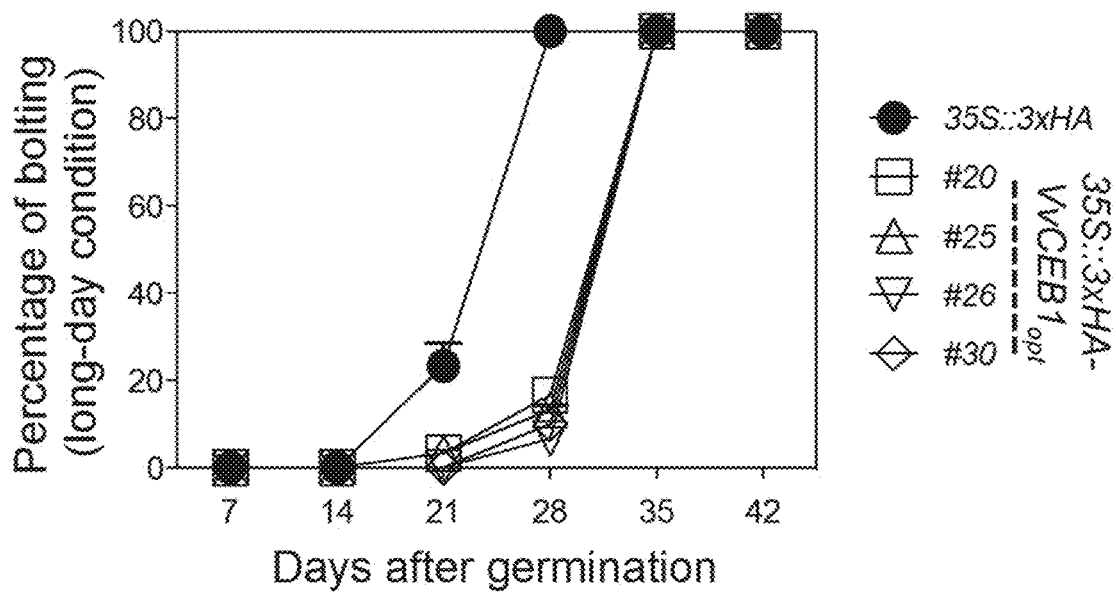

FIGS. 15A-15D illustrate VvCEB1$_{opt}$ overexpression delays flowering and leaf senescence in Arabidopsis. FIG. 15A provides representative images of delayed flowering and leaf senescence of the VvCEB1$_{opt}$-overexpressing line (#26) compared to the 35S:: 3×HA empty-vector control line under half-day condition. Seeds of four independent 35S:: 3×HA-VvCEB1 opt lines (#20, #25, #26, and #30) and 35S:: 3×HA (empty-vector control) line were germinated and grown in soil mix for 10 weeks under a 12-h photoperiod. Scale bar, 5 cm. FIG. 15B provides representative images of delayed flowering of the VvCEB1$_{opt}$-overexpressing line (#26) compared to the 35S:: 3×HA empty-vector control line under long-day condition. Seeds of four independent VvCEB1$_{opt}$-overexpressing lines and the 35S:: 3×HA empty-vector control line were germinated and grown on MS agar medium under a 16-h photoperiod. Scale bar, 5 cm. FIGS. 15C and 15D illustrate the quantification of flowering time under half-day (FIG. 15C) and long-day (FIG. 15D) conditions (n=3 replicates). In summary, the VvCEB1$_{opt}$-overexpressing lines showed delayed flowering time.

Figure 16A:
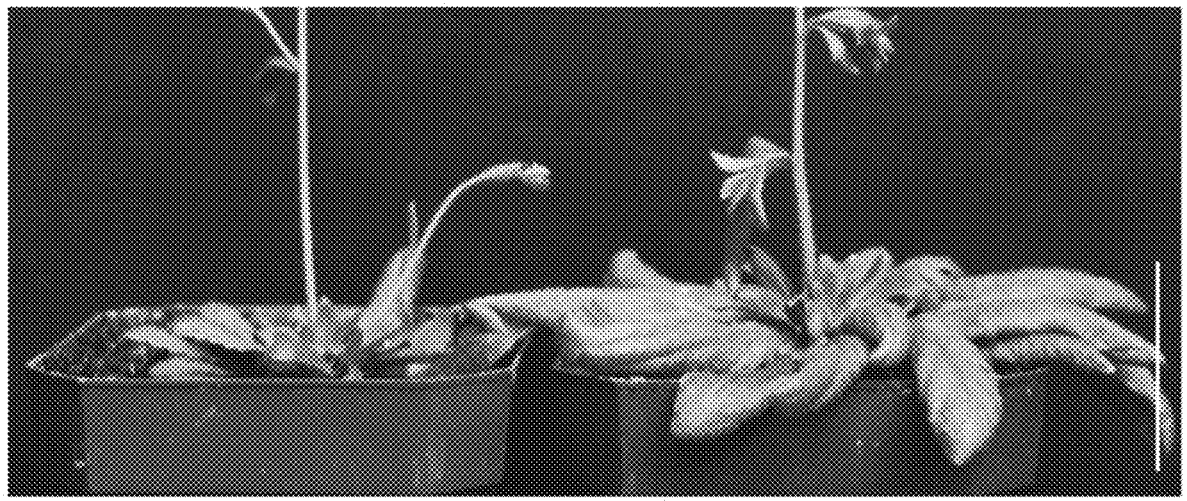
FIGS. 16A-16C illustrate VvCEB1$_{opt}$-overexpressing *Arabidopsis* plants increase inflorescence stem thickness by increasing cell size.
Figure 16B:
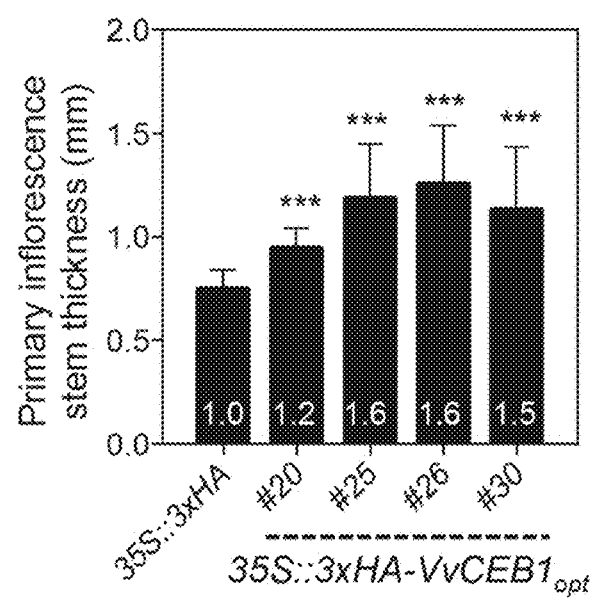
Figure 16C:
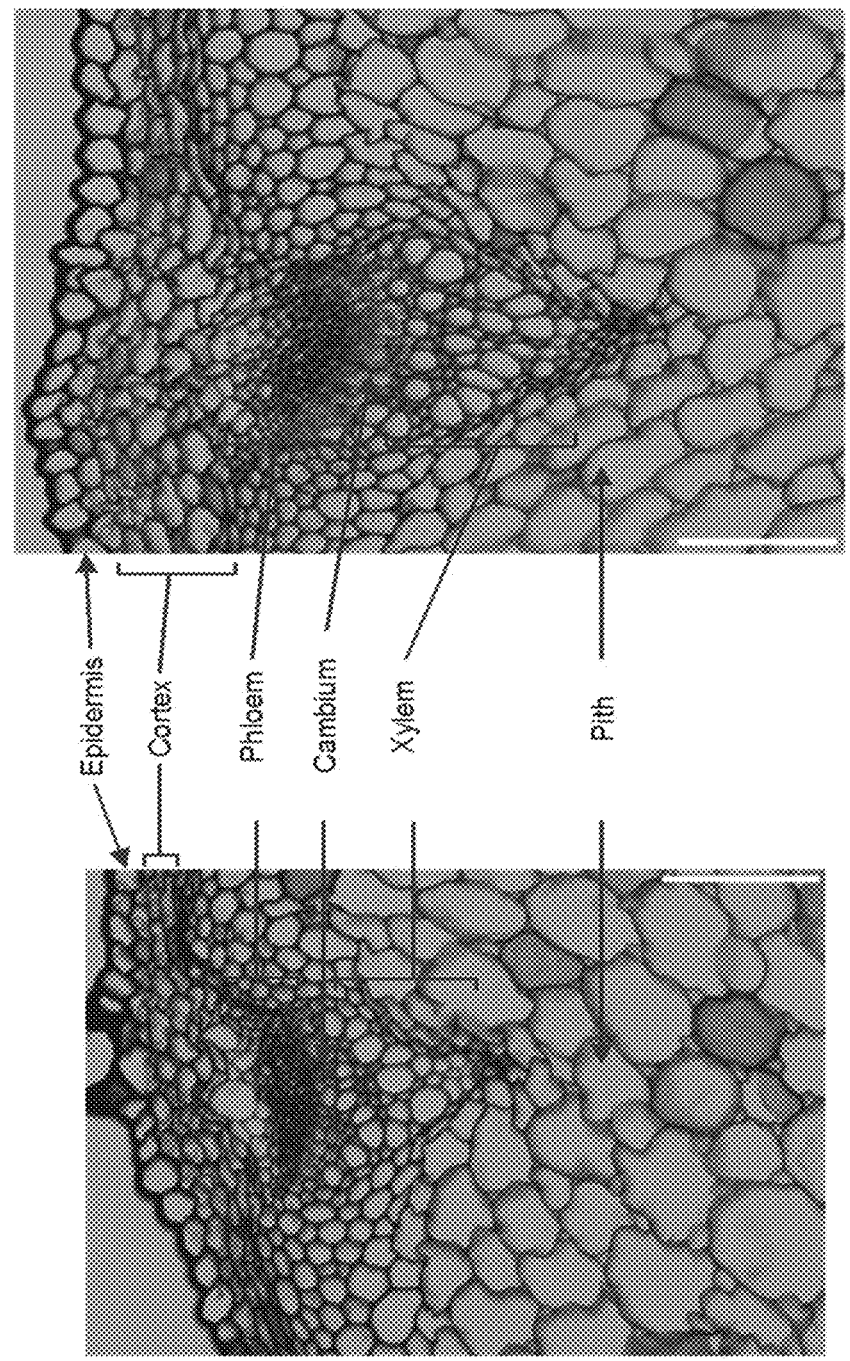

FIGS. 16A-16C illustrate VvCEB1$_{opt}$-overexpressing Arabidopsis plants increase inflorescence stem thickness by increasing cell size. FIGS. 16A to 16C illustrate seeds of four VvCEB1$_{opt}$-overexpressing lines and the 35S:: 3×HA empty-vector control line were germinated and grown in soil mix under a 12-h photoperiod (12 hours of light per day). Representative images of the primary inflorescence stem of the 35S:: 3×HA empty-vector control line and the VvCEB1$_{opt}$-overexpressing line (#26) at 2 weeks after bolting are provided in FIG. 16A. Scale bar, 5 cm. Quantitation of the diameter of the primary inflorescence stem (n=30) is shown in FIG. 16B. Representative images of stem cross sections are provided in FIG. 16C. Primary inflorescence stems were stained with toluidine blue O. Scale bar, 100 µm. Values represent means±s.d., ***p<0.001, One-way ANOVA with Dunnett's multiple comparison test. In summary, the VvCEB1$_{opt}$-overexpressing lines showed increased the thickness of the primary inflorescence stem by increasing cell size.

Figure 17A:
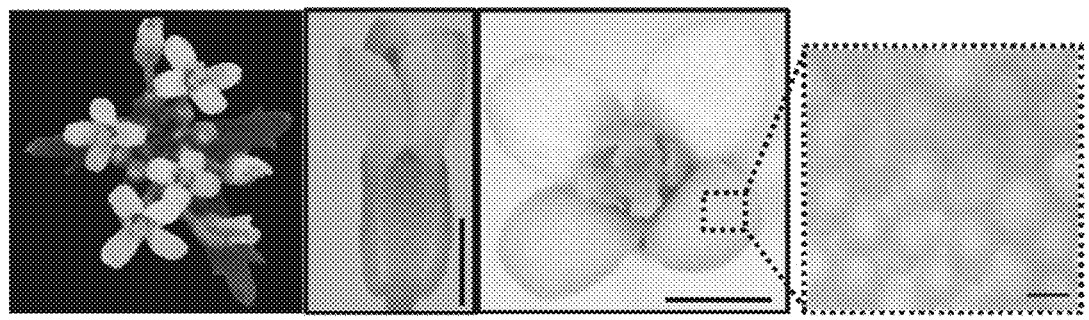
FIGS. 17A-17G illustrate VvCEB1$_{opt}$ overexpression increases flower size and number of petals and sepals in *Arabidopsis*.
Figure 17A:
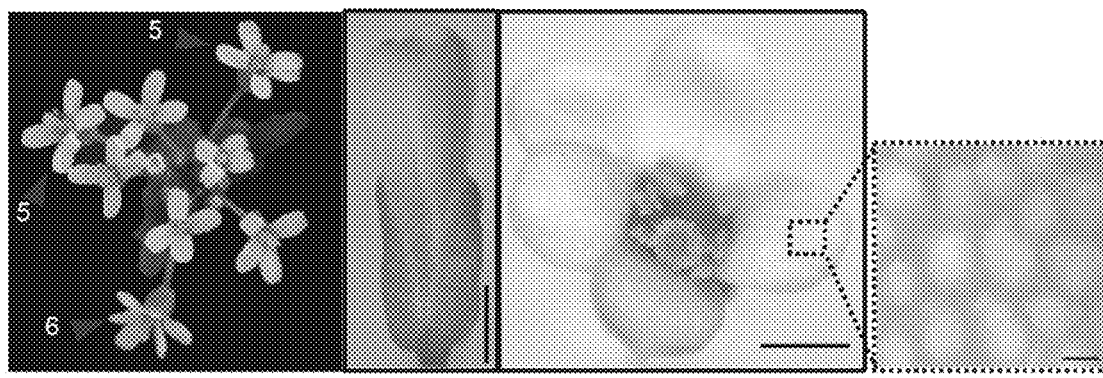
Figure 17B:
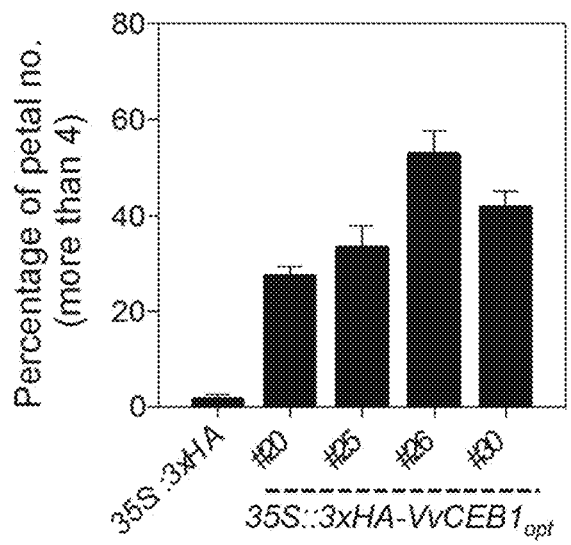
Figure 17C:
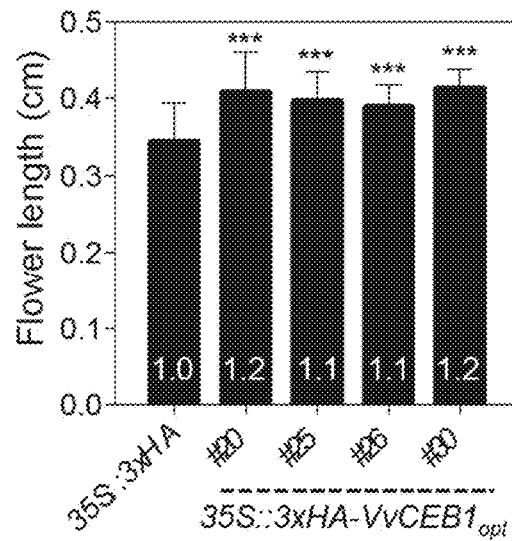
Figure 17D:
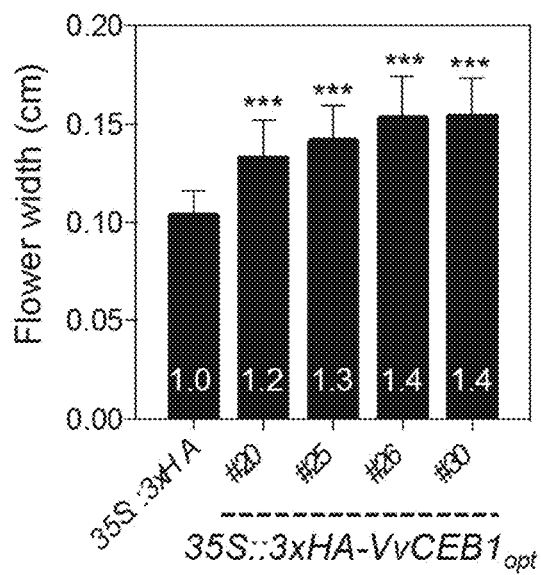
Figure 17E:
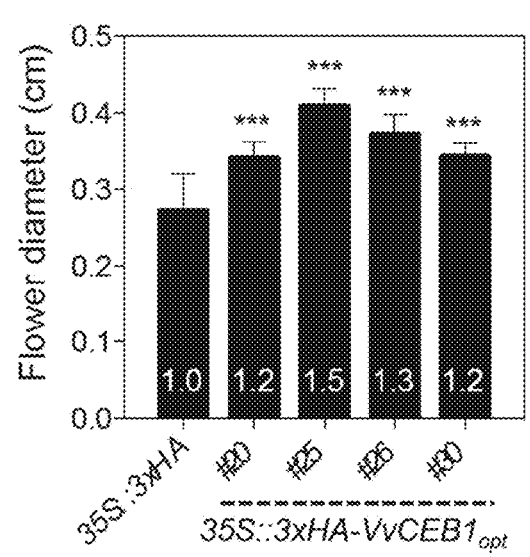
Figure 17F:
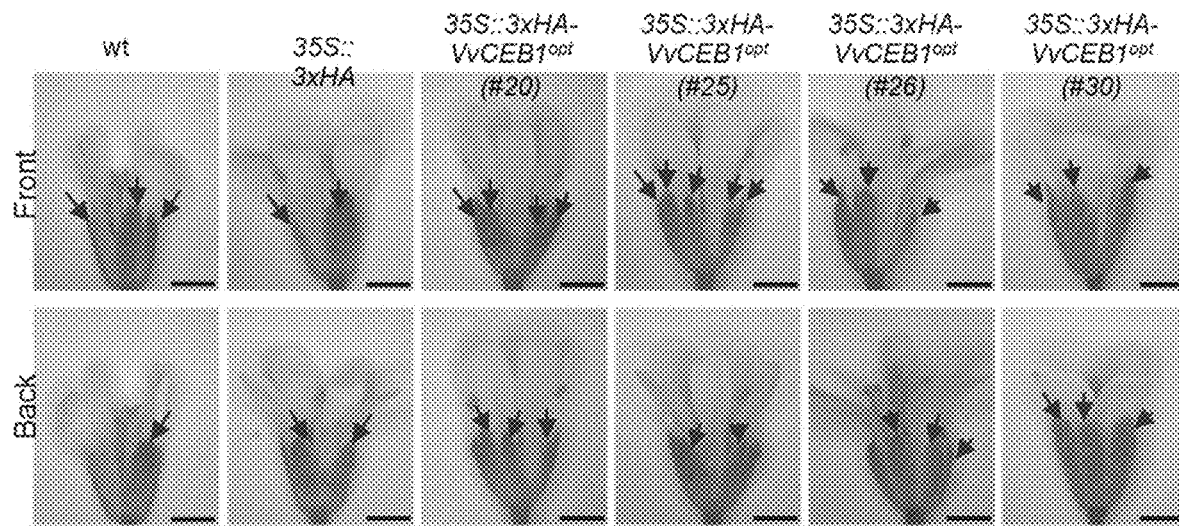
Figure 17G:
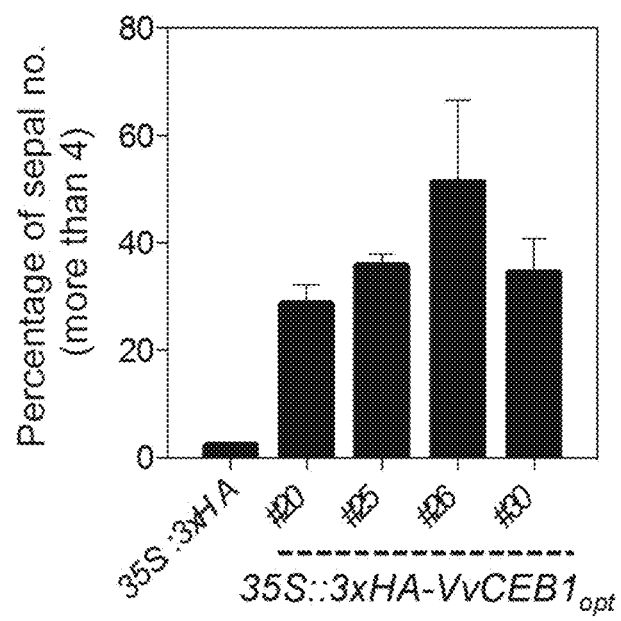

FIGS. 17A-17G illustrate VvCEB1$_{opt}$ overexpression increases flower size and number of petal and sepal in Arabidopsis. Representative images of the inflorescence apex, flower, and petal epidermis cell (left to right) of the VvCEB1$_{opt}$-overexpressing line (#26) and the 35S:: 3×HA empty-vector control line are provided in FIG. 17A. Numbers indicate number of petals in flowers. Magnified images represent petal epidermal cells. Scale bars indicate 0.1 cm, 0.1 cm, and 10 µm (left to right), respectively. Percentage of flowers with petal numbers greater than 4 (n=3 replicates) provided in FIG. 17B and quantification of flower length (n=63) in FIG. 17C. Quantification of flower width measured horizontally (n=63) is shown in FIG. 17D and flower diameter (n=30) FIG. 17E. FIG. 17F provides representative flower images of four VvCEB1$_{opt}$-overexpressing lines, Col-0 wild type (wt), and the 35S:: 3×HA empty-vector control line. Red arrows indicate sepal number. Scale bar, 1 mm. Quantification of percentage of flowers with sepal number greater than 4 (n=3 replicates) is shown in FIG. 17G. Values represent means±s.d., ns=non-significant, ***p<0.001, One-way ANOVA with Dunnett's multiple comparison test. In summary, the VvCEB1$_{opt}$-overexpressing lines showed an increase in flower size and an increase in flower petal and sepal number.

Figure 18A:
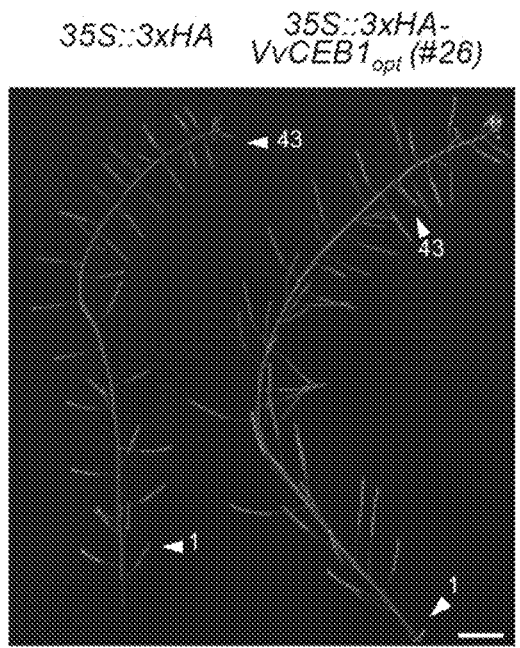
FIGS. 18A-18L illustrate VvCEB1$_{opt}$ overexpression increases size of reproductive structures and seed yield in *Arabidopsis*.
Figure 18B:
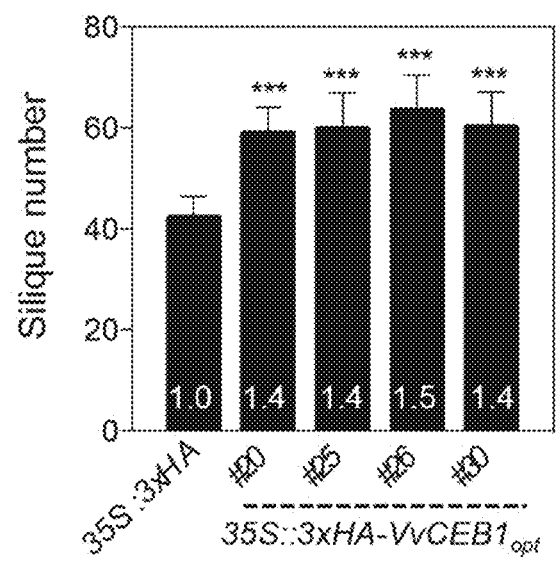
Figure 18C:
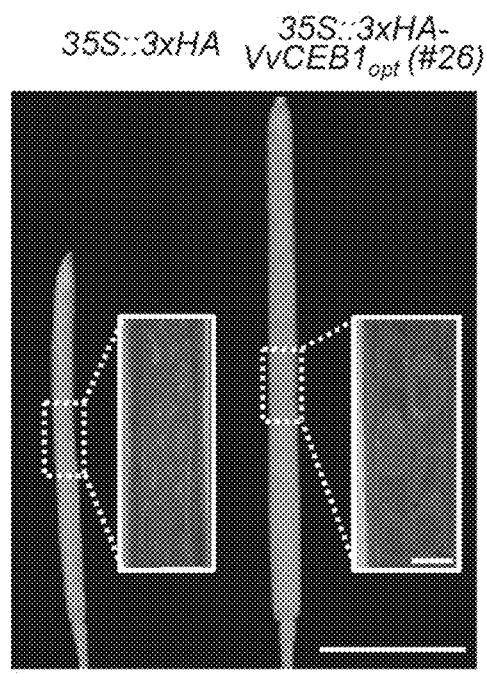
Figure 18D:
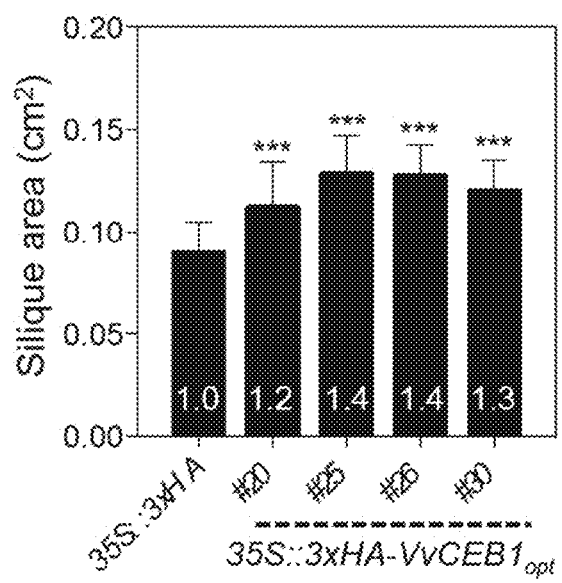
Figure 18E:
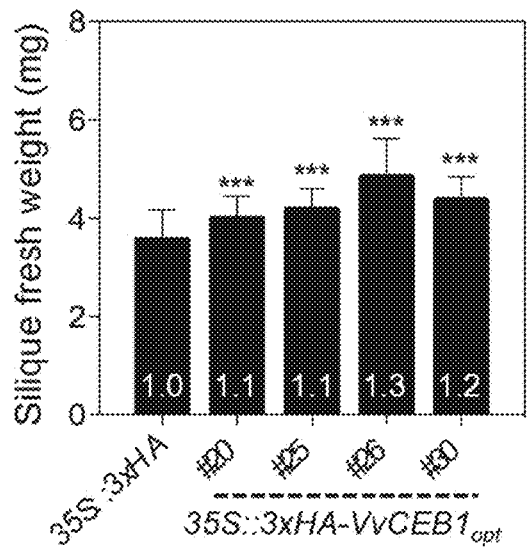
Figure 18F:
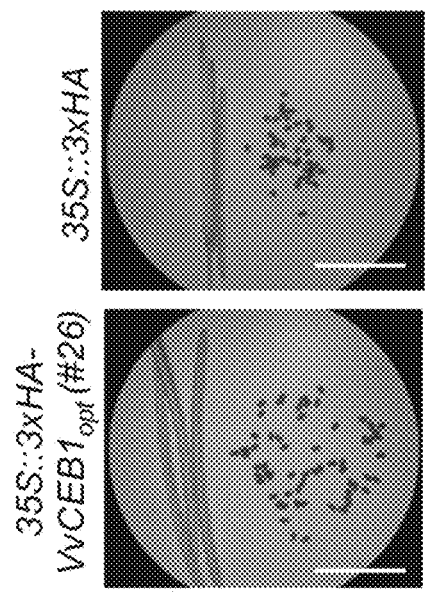
Figure 18G:
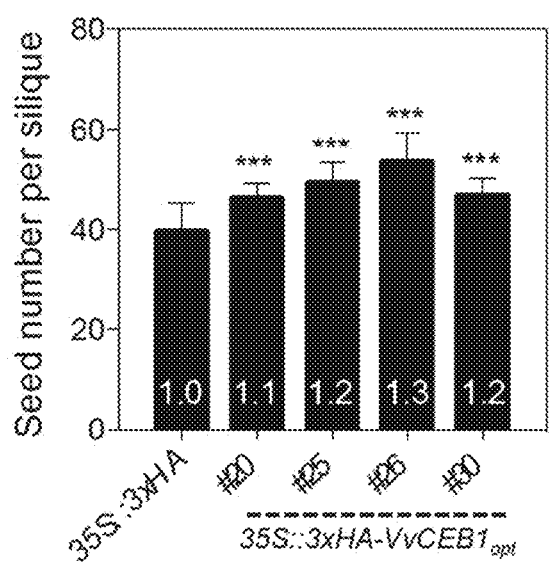
Figure 18H:
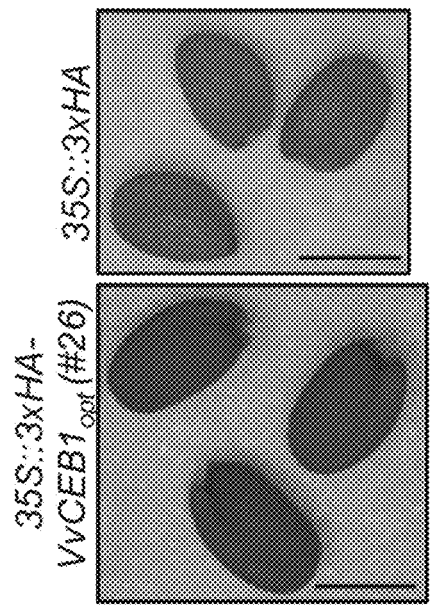
Figure 18I:
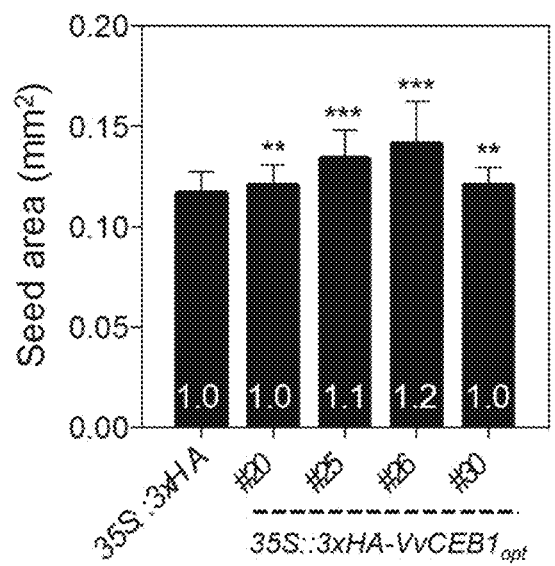
Figure 18J:
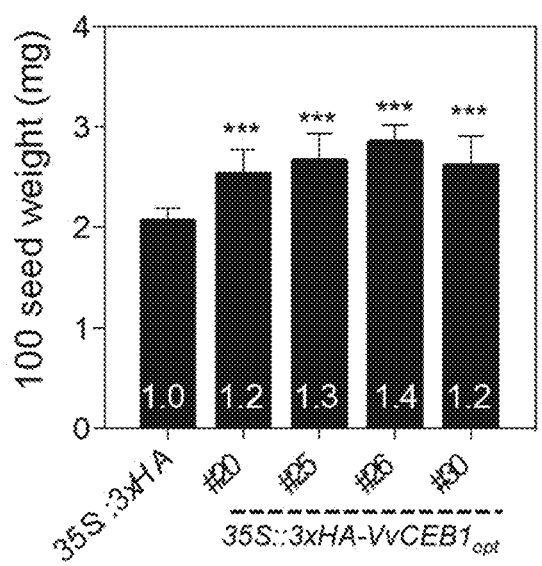
Figure 18K:
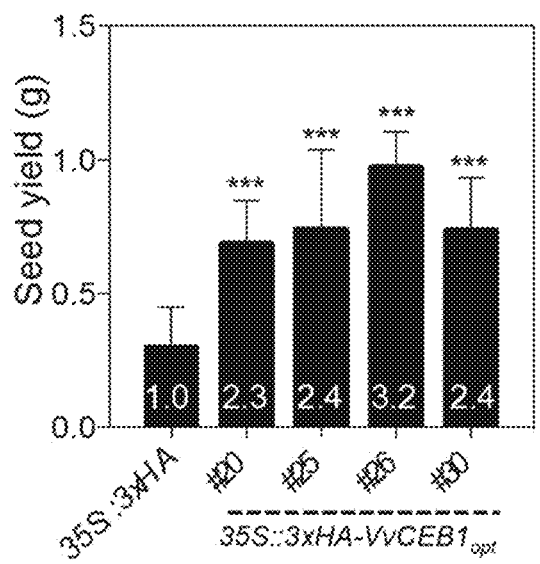
Figure 18L:
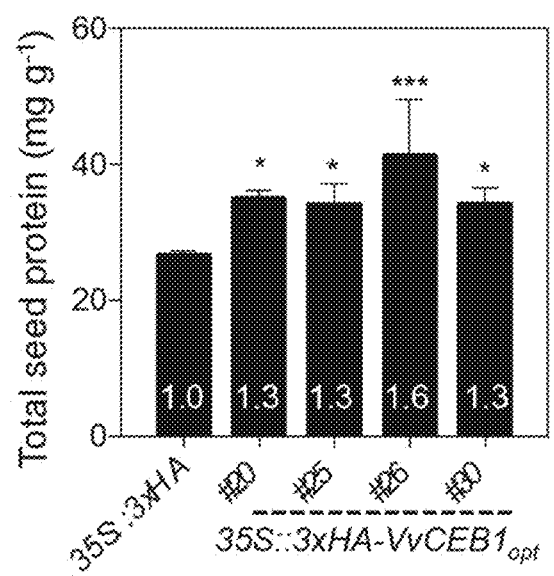

FIGS. 18A-18L illustrate VvCEB1$_{opt}$ overexpression increases size of reproductive structures and seed yield in Arabidopsis. Representative images of primary inflorescence stem of the VvCEB1$_{opt}$-overexpressing line (#26) and the 35S:: 3×HA empty-vector control line. Arrowheads indicate 1$^{st}$ and 43$^{rd}$ silique from rosette leaf are shown in FIG. 18A. Scale bar, 1.5 cm. Quantification of silique number within primary inflorescence (n=20) is illustrated in FIG. 18B. Representative images of fully developed siliques of VvCEB1$_{opt}$-overexpressing line (#26) and the 35S:: 3×HA empty-vector control line are provided in FIG. 18C. Scale bar, 0.5 cm. Scale bar in the magnified images, 0.5 mm. Quantification of silique area (n=50) is shown in FIG. 18D and silique fresh weight (n=40) in FIG. 18E. Representative images of seed number per dried silique of the VvCEB1$_{opt}$-overexpressing line (#26) and the 35S:: 3×HA empty-vector control line are shown in FIG. 18F. Scale bar, 0.5 cm. Quantification of seed number per silique (n=30) is provided in FIG. 18G. Representative seed images of the VvCEB1$_{opt}$-overexpressing line (#26) and the 35S:: 3×HA empty-vector control line are provided in FIG. 18H. Scale bar, 0.5 mm. Quantification of seed size (n=100) is provided in FIG. 18I, 100-seed weight (n=30) in FIG. 18J, and seed yield per plant (n=10) FIG. 18K. Quantification of total seed protein (n=4 replicates) is provided in FIG. 18L. Values represent means±s.d., ns=non-significant, *p<0.05, p<0.01, and *p<0.001, One-way ANOVA with Dunnett's multiple comparison test. In summary, the VvCEB1$_{opt}$-overexpressing lines showed a significant increase in silique number, silique size, seed number per silique, seed size, seed yield, and seed total protein amount.

Figure 19A:
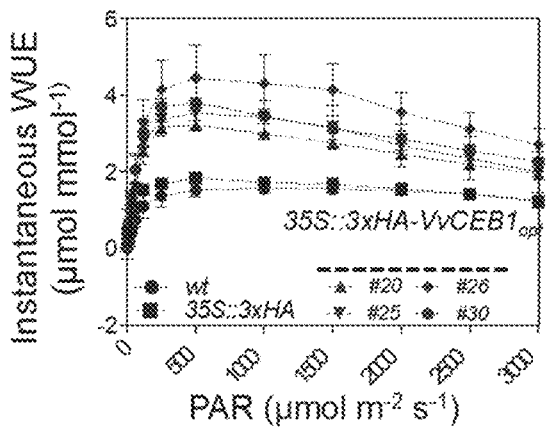
FIGS. 19A-19J illustrate VvCEB1$_{opt}$ overexpression improves water-use efficiency in *Arabidopsis*.
Figure 19B:
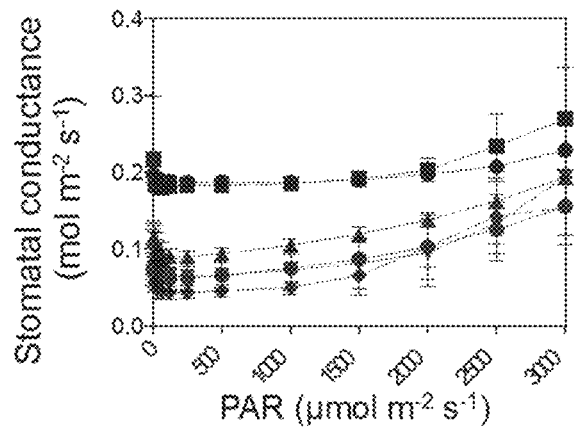
Figure 19C:
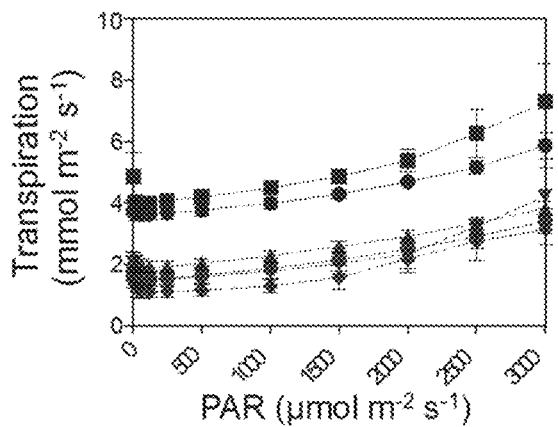
Figure 19D:
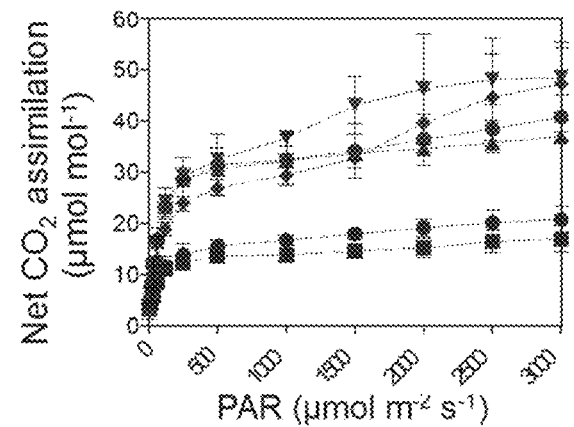
Figure 19E:
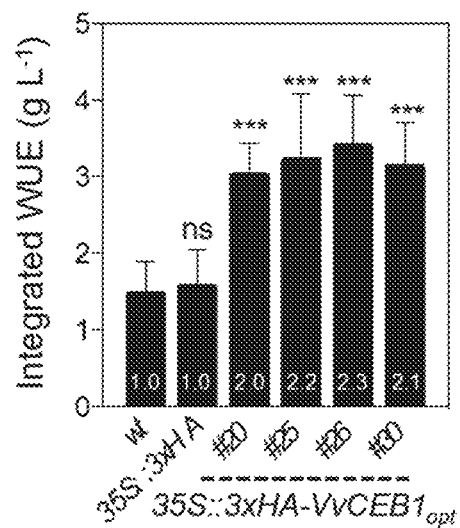
Figure 19F:
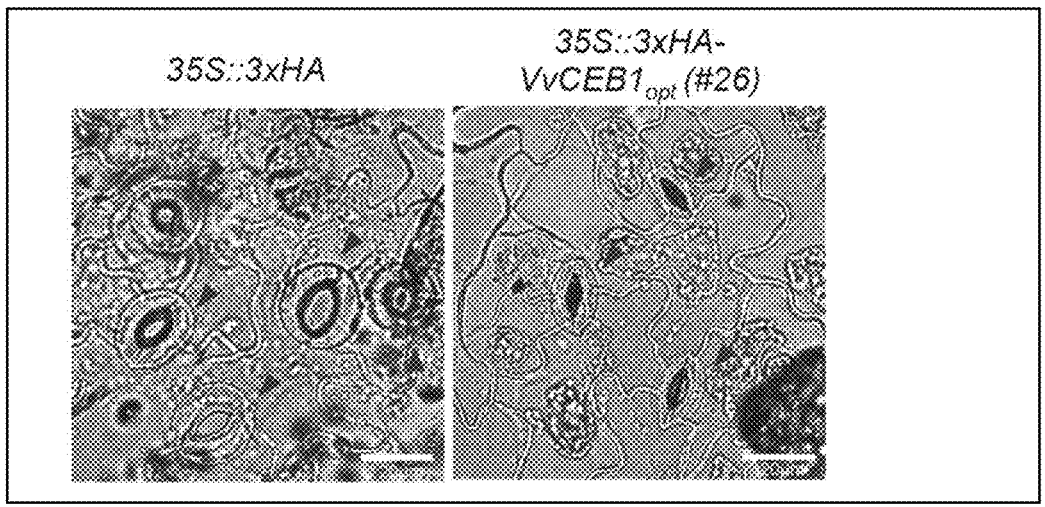
Figure 19G:
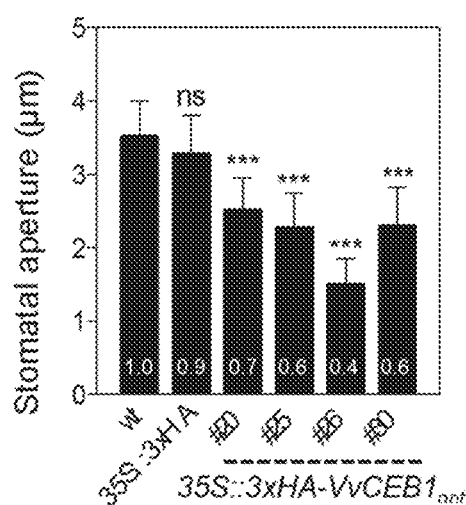
Figure 19H:
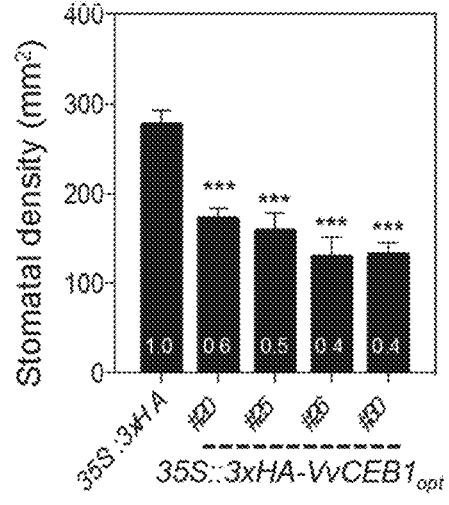
Figure 19I:
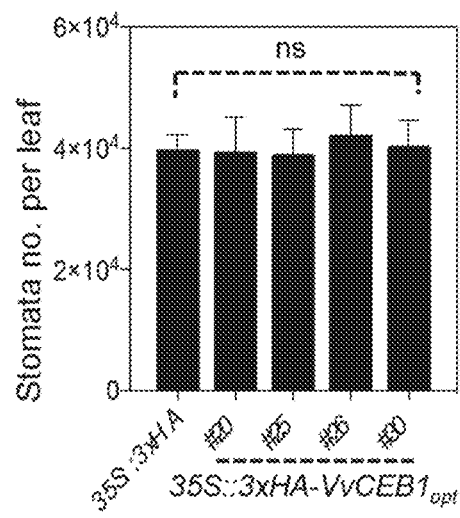
Figure 19J:
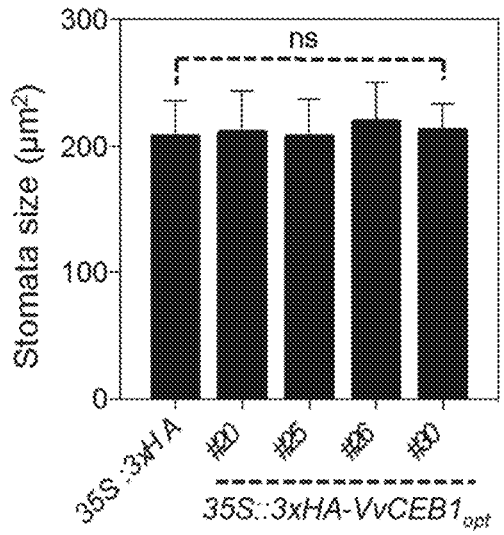

FIGS. 19A-19J illustrate VvCEB1$_{opt}$ overexpression improves water-use efficiency in Arabidopsis. Instantaneous water-use efficiency (WUE) is illustrated in FIG. 19A, stomatal conductance (FIG. 19B), transpiration (FIG. 19C), and Net CO$_2$ assimilation (FIG. 19D). Gas exchange data were collected using whole plants at photosynthetically active radiation (PAR) levels of 0-3000 µmol m$^{-2}$ s$^{-1}$ (n=3 replicates). Seeds of four VvCEB1$_{opt}$ overexpressing lines, Col-0 wild type (wt), and the 35S:: 3×HA empty-vector control line were germinated and grown in soilless growth medium for 3 weeks under a 12-h photoperiod. Quantification of integrated WUE. Integrated WUE of plants under water-sufficient conditions was calculated from measurements of water loss and whole plant dry weight (n=10; FIG. 19D). Seeds of four VvCEB1$_{opt}$-overexpressing lines, Col-0 wild type (wt), and the 35S:: 3×HA empty-vector control line were germinated and grown in coarse sand for 3 weeks under a 12-h photoperiod. Light-inducible stomatal opening assay results are shown in FIG. 19E. Representative images of fully opened stomatal aperture and density of the VvCEB1$_{opt}$-overexpressing line (#26) and the 35S:: 3×HA empty-vector control line. Scale bar, 20 µm. Red arrowheads indicate the positions of stomata in the lower epidermis. Width of fully opened stomatal apertures (n=50) are illustrated in FIG. 19G. Quantification of stomatal density per unit mm$^2$ (n=5) are illustrated in FIG. 19H. Total number of stomata per leaf (n=5) illustrated in FIG. 19I and quantification of stomatal size of four VvCEB1opt-overexpressing lines and the 35S:: 3×HA empty-vector control line (n=50) are provided in 19H. Values represents means±s.d., ns=non-significant, and ***p<0.001, One-way ANOVA with Dunnett's multiple comparison test. Seeds of four VvCEB1$_{opt}$-overexpressing lines, Col-0 wild type (wt), and the 35S:: 3×HA empty-vector control line were germinated and grown in soil mix for 4 weeks under a 12-h photoperiod. In summary, the VvCEB1$_{opt}$-overexpressing lines showed a significant increase in both instantaneous and integrated water-use efficiency by reducing stomatal aperture.

Figures 20A, 20B:
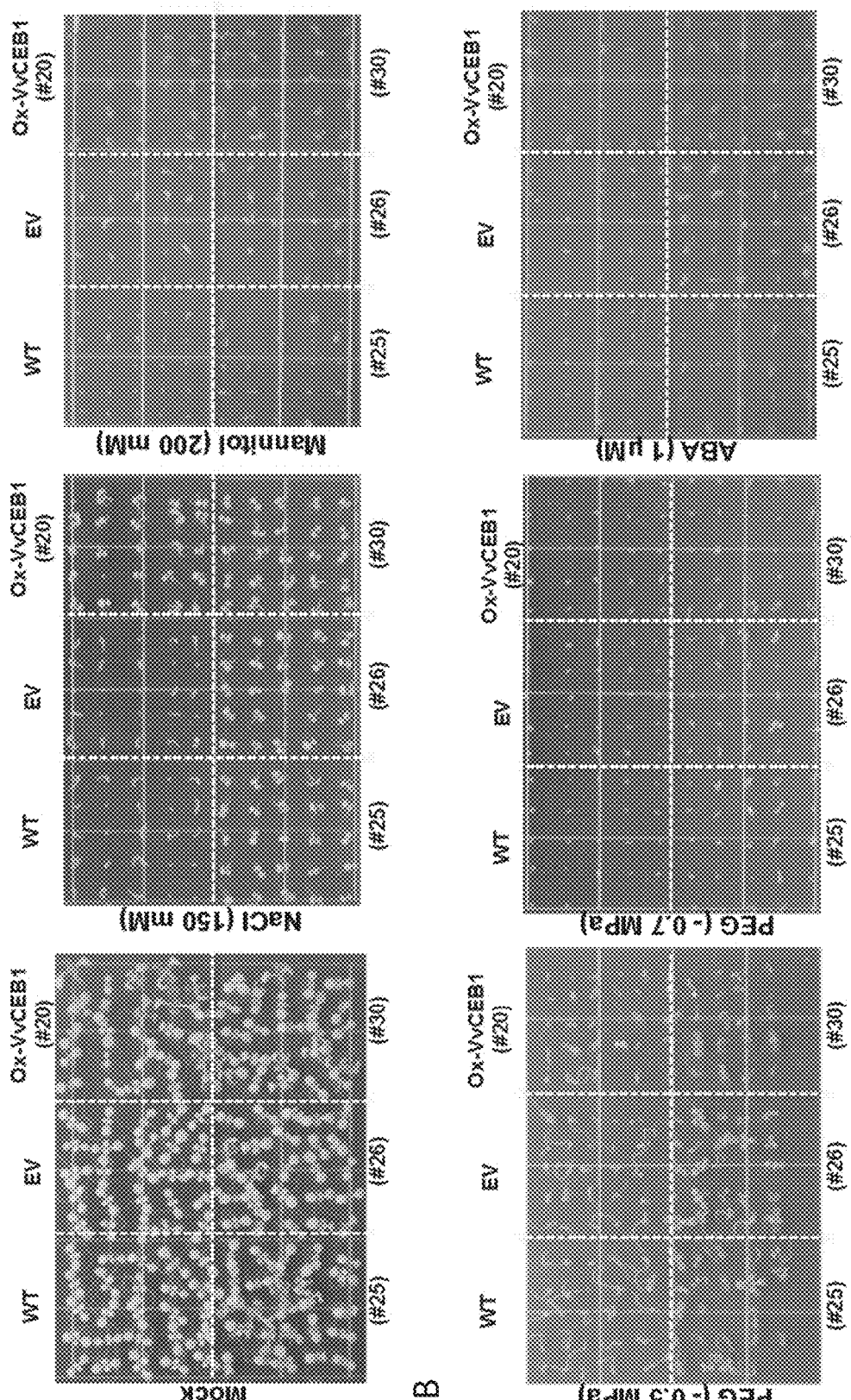
FIGS. 20A-20C illustrate VvCEB1$_{opt}$ overexpression increased seed germination and green cotyledon rates under salinity and osmotic stress conditions.
Figure 20C:
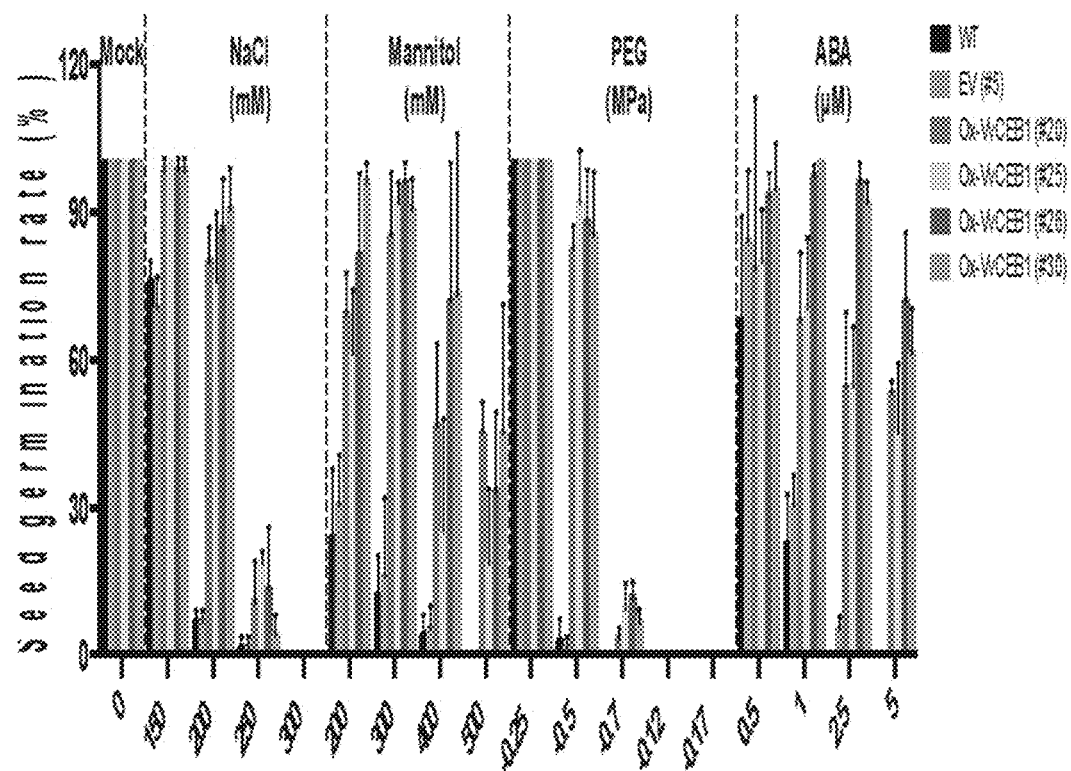
Figure 20C:
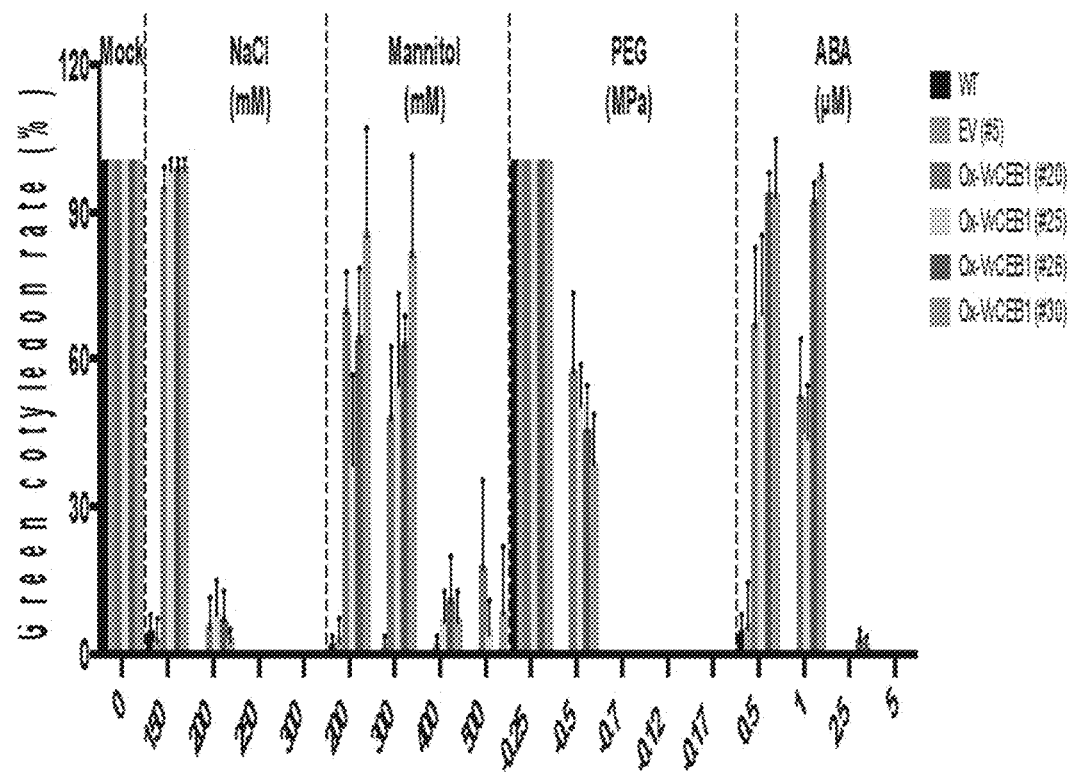

FIGS. 20A-20C illustrate VvCEB1$_{opt}$ overexpression increased seed germination and green cotyledon rates under salinity and osmotic stress conditions. Seeds from four independent VvCEB1$_{opt}$-overexpressing lines, wild-type (wt) A. thaliana ecotype Col-0, and the 35S:: 3×HA empty-vector control line were plated on ½ MS containing NaCl (0, 150, 200, 250, and 300 mM), Mannitol (200, 300, 400, and 500 mM), PEG (−0.25, −0.5, −0.7, −0.12, and −0.17 MPa, and ABA (0.5, 1, 2.5, 5 µM) and measured seed germination and green cotyledon rates. Images were captured at 7 days after stratification (Mock, NaCl, and Mannitol) or 5 days after stratification (PEG and ABA) as shown in FIG. 20A. Seed germination percentages for each experiment were scored and calculated at 7 days after stratification (Mock, NaCl, and Mannitol) or 5 days after stratification (PEG and ABA) (Seed number per each line=75, n=3; FIG. 20B). Green cotyledon percentages for each experiment were scored and calculated at 7 days after stratification (Mock, NaCl, and Mannitol) or 5 days after stratification (PEG and ABA) (Seed number per each line=75, n=3; FIG. 20C). In summary, the VvCEB1$_{opt}$-overexpressing lines showed improved salinity and osmotic stress tolerance during the seed germination stage.

Figure 21A:
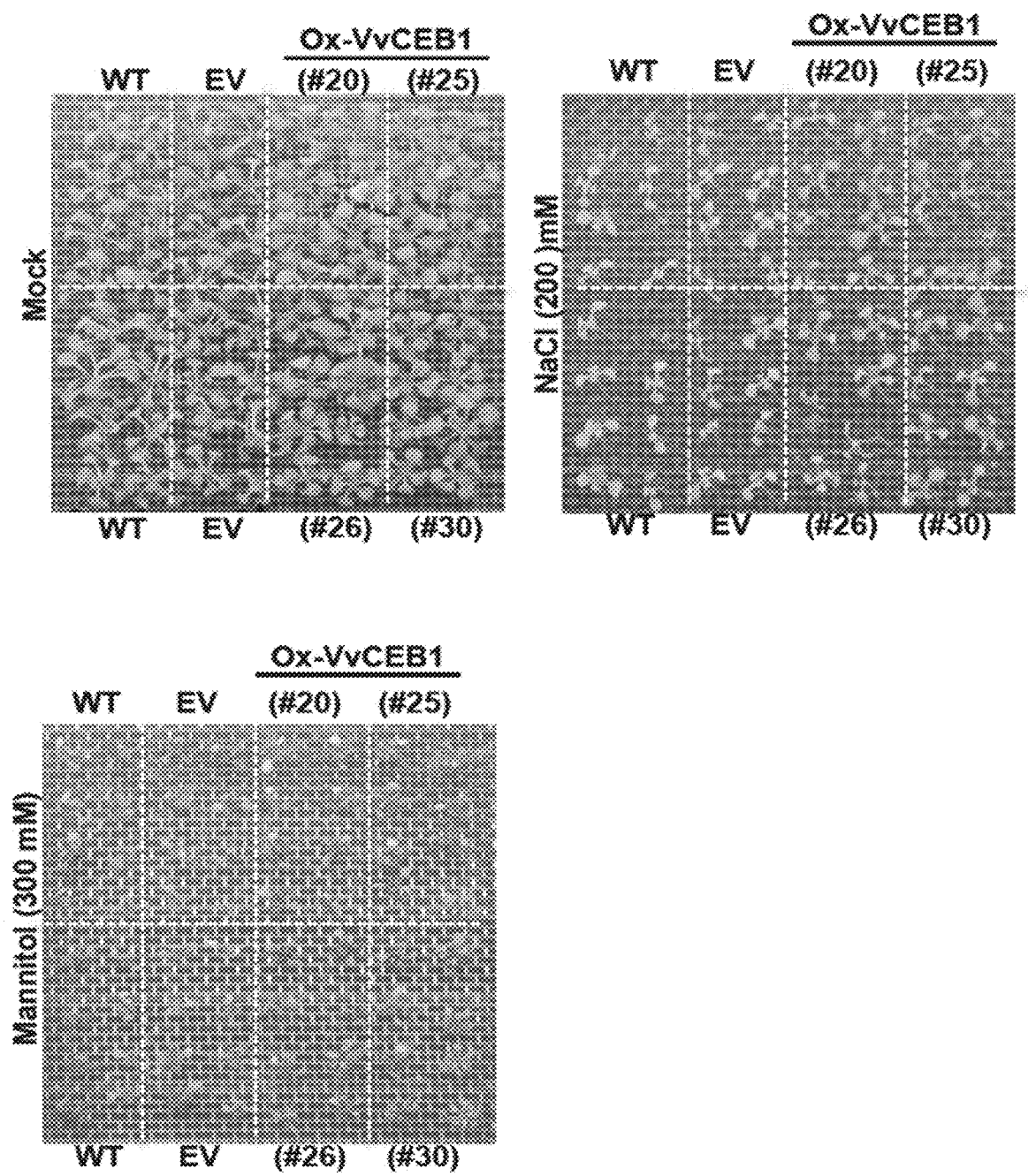
FIGS. 21A-21C illustrate VvCEB1$_{opt}$ overexpression increased fresh and dry weight under salinity and osmotic stress conditions.
Figure 21B:
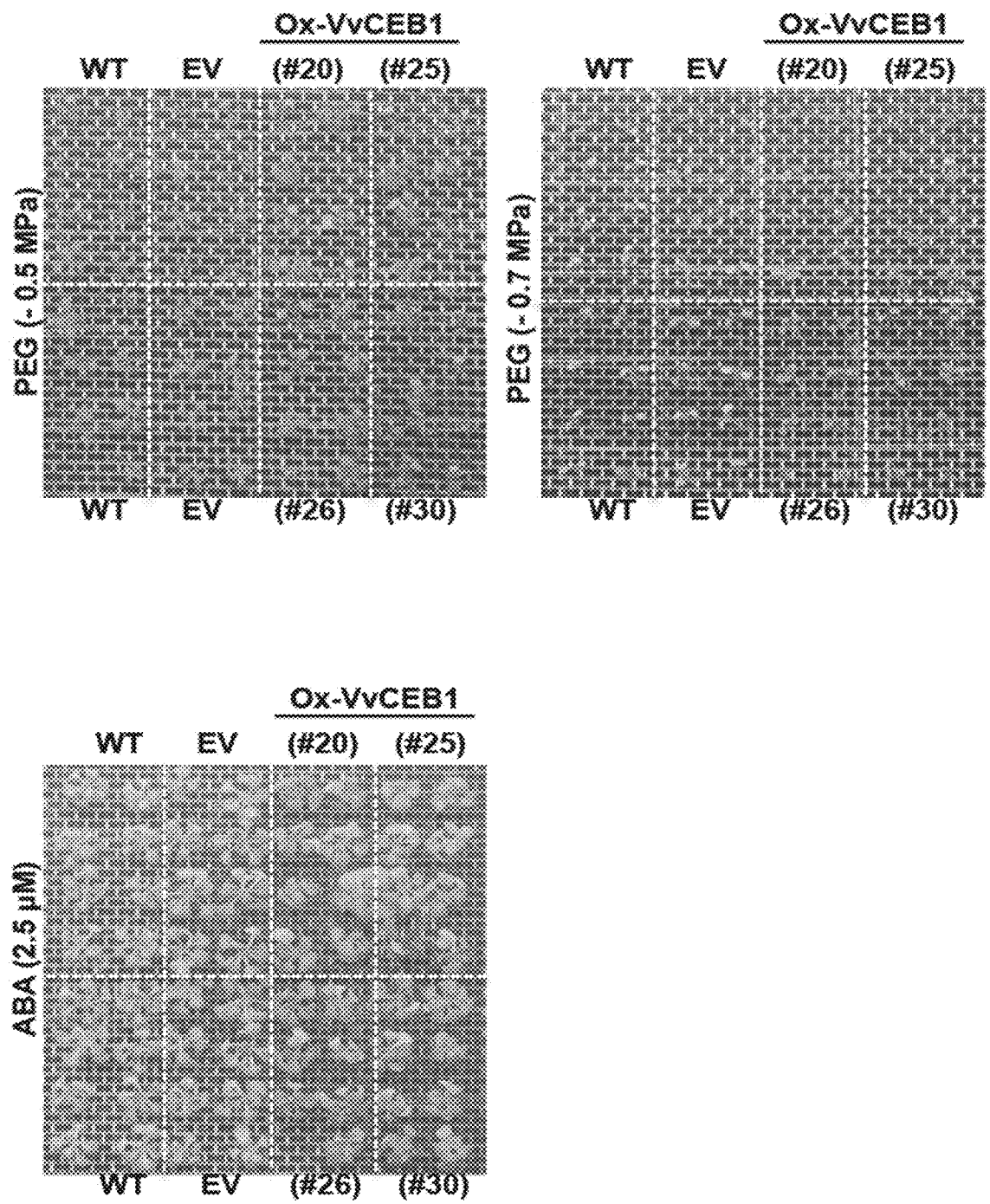
Figure 21C:
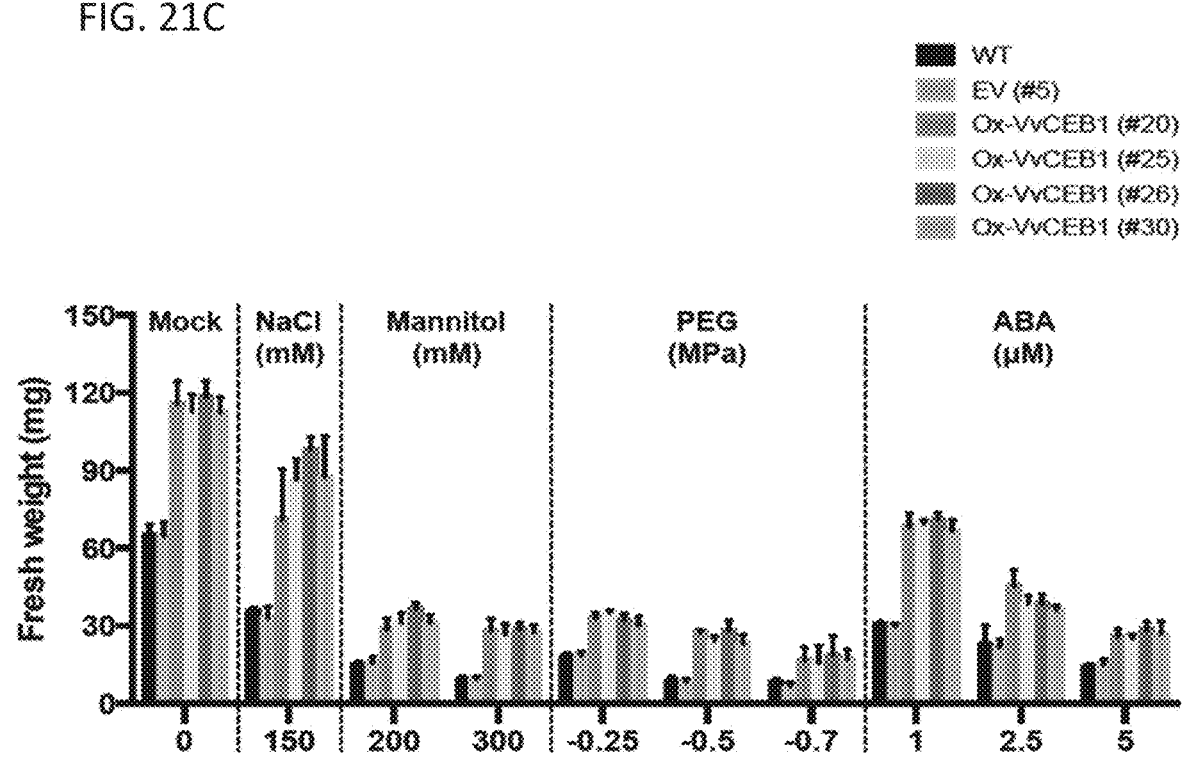
Figure 21C:
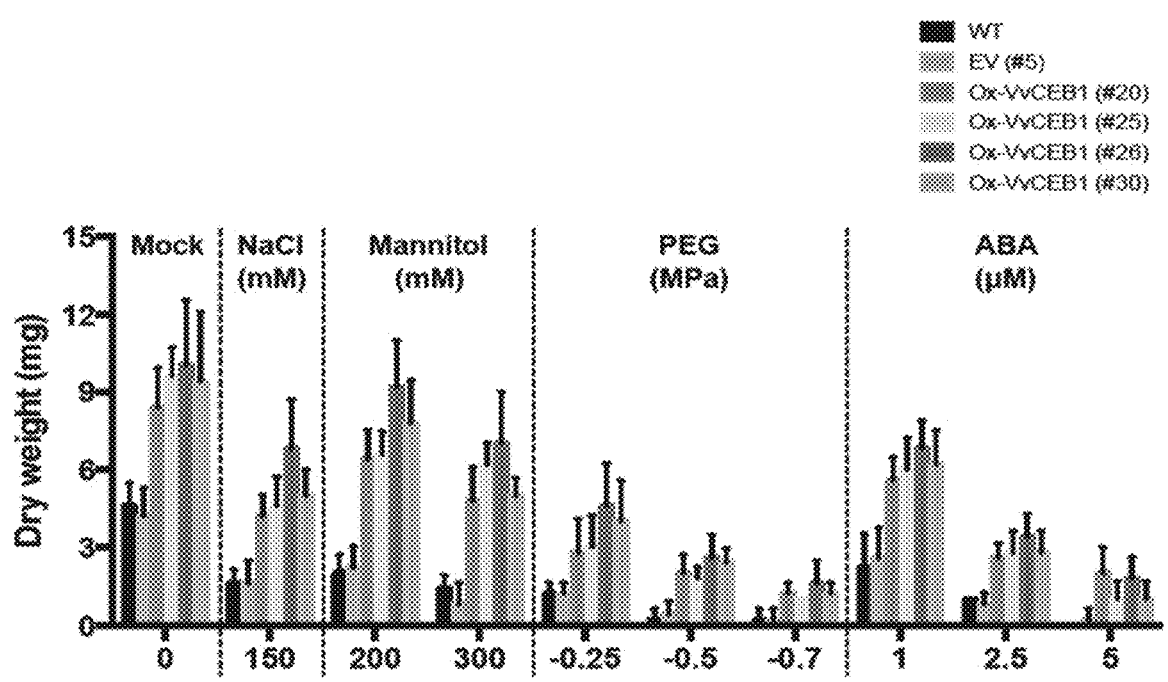

FIGS. 21A-21C illustrate VvCEB1$_{opt}$ overexpression increased fresh and dry weight under salinity and osmotic stress conditions. Seeds from four independent VvCEB1$_{opt}$-overexpressing lines, wild-type (wt)A. thaliana ecotype Col-0, and the 35S:: 3×HA empty-vector control line were placed on nylon mesh on ½ MS medium and grown for 7 days after germination. Seedlings were transferred on ½ MS medium containing NaCl (0, 150, 200, 250, and 300 mM), Mannitol (200, 300, 400, and 500 mM), PEG (−0.25, −0.5, −0.7, −0.12, and −0.17 MPa, and ABA (0.5, 1, 2.5, 5 µM) and were grown for 14 days. Images were captured at 14 days after stress treatment (Mock, NaCl, Mannitol, PEG, and ABA; FIG. 21A. Fresh weights of WT, EV, and Ox-VvCEB1 for each experiment were measured (Seedling number per each line=40, n=5; FIG. 21B). Dry weight of WT, EV, and Ox-VvCEB1 for each experiment were measured (Seedling number per each line=40, n=5; FIG. 21C). In summary, the VvCEB1$_{opt}$-overexpressing lines showed greater salinity and osmotic stress tolerance during vegetative stages of growth.

Figure 22A:
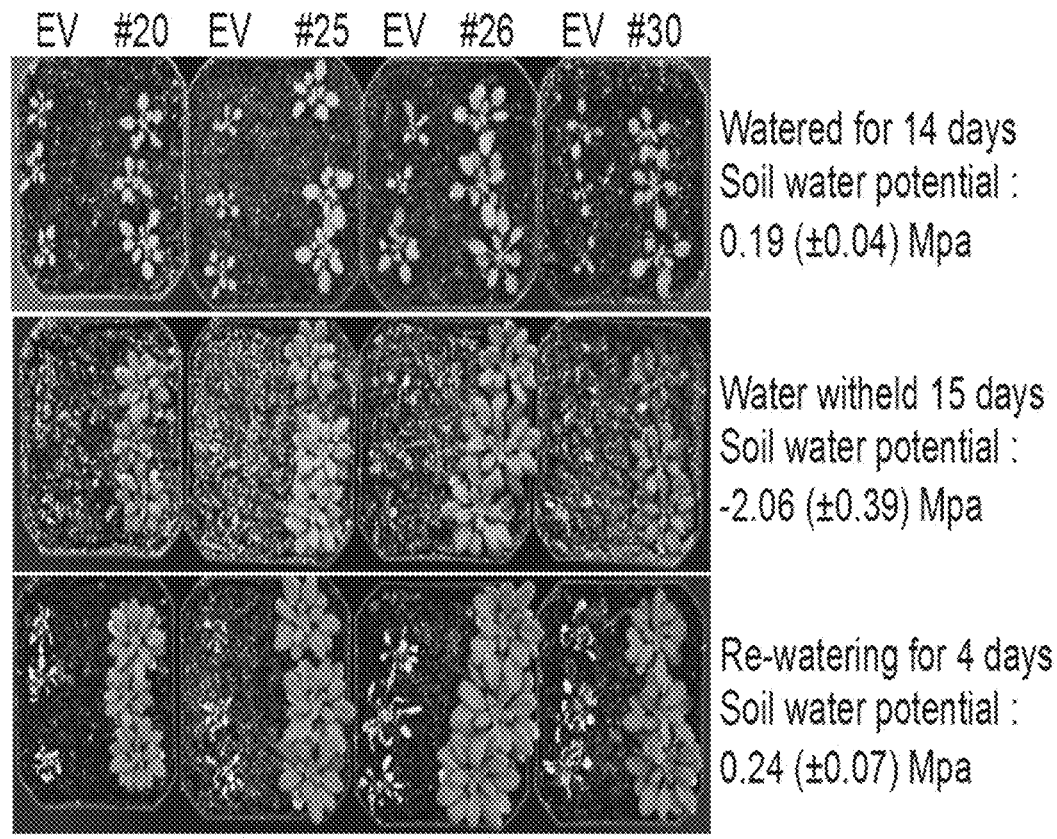
FIGS. 22A-22B illustrate VvCEB1$_{opt}$ overexpression showed increased survival rate under acute water-deficit condition.
Figure 22B:
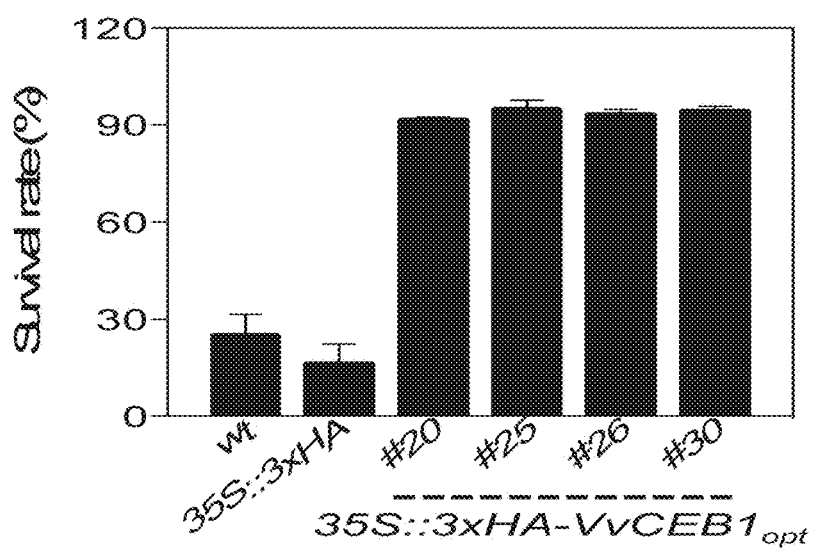

FIGS. 22A-22B illustrate VvCEB1$_{opt}$ overexpression showed increased survival rate under water-deficit condition. Representative images of four VvCEB1$_{opt}$-overexpressing lines (#20, #25, #26, and #30) and the 35S:: 3×HA empty-vector (EV) control line at 14, 29, and 33 days after germination exposed to drought attenuation assay using acute water-deficit stress (FIG. 22A). Survival rates (n=180) are provided in FIG. 22B. Seeds of four VvCEB1$_{opt}$ overexpressing lines, Col-0 wild type (wt), and empty-vector control line were germinated and grown in soilless mix under a 12-h photoperiod. In summary, the VvCEB1$_{opt}$-overexpressing lines showed improved drought stress attenuation and survival rate under acute drought stress condition.

Figure 23A:
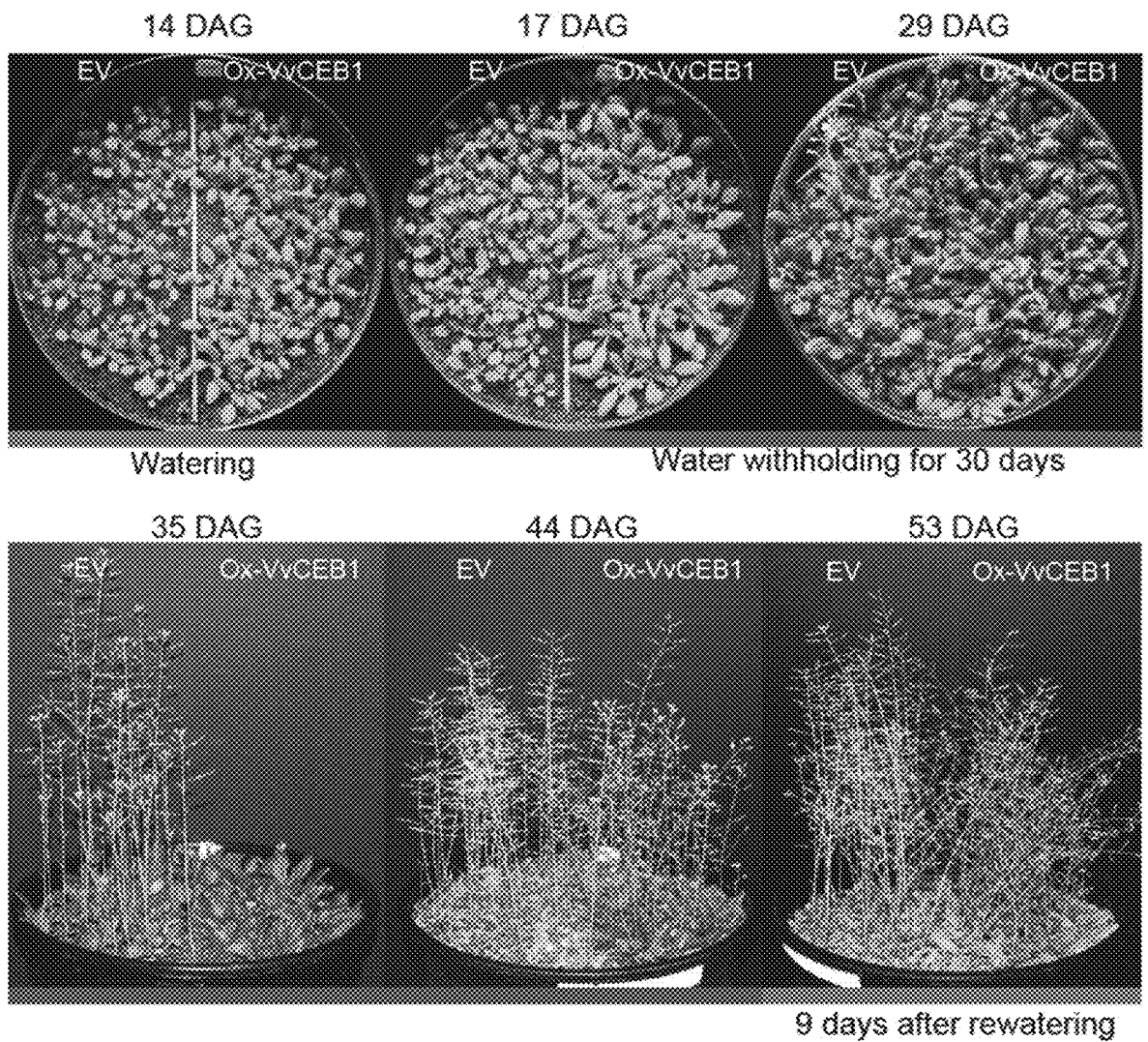
FIGS. 23A-23B illustrate VvCEB1$_{opt}$ overexpressing plants exhibit drought stress tolerance under chronic water-deficit condition.
Figure 23B:
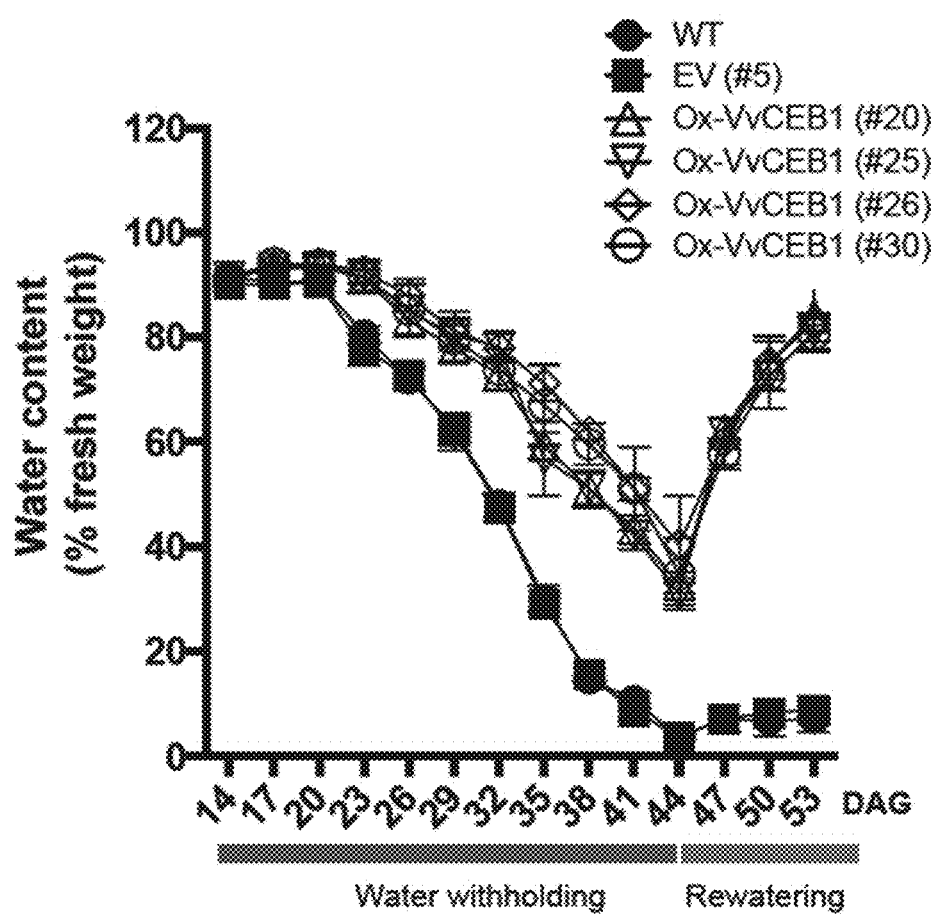

FIGS. 23A-23B illustrate VvCEB1$_{opt}$ overexpressing plants exhibit drought stress tolerance under chronic drought condition. The 14-day-old well-watered four VvCEB1$_{opt}$ overexpressing lines, Col-0 wild type (wt), and empty-vector control plants were grown for 30 days under the same conditions, but water was withheld for 30 days. The drought-stressed plants were then irrigated for 9 days (FIG. 23A). Images were captured at 14, 17, 29, 35, 44, and 53 days after germination. Leaf water content of four VvCEB1$_{opt}$ overexpressing lines, Col-0 wild type (wt), and empty-vector control plants were measured every 3 days during the study (FIG. 23B). Leaf water content was calculated by measuring fresh weight and dry weight (5 leaves for each line, n=3). In summary, the VvCEB1$_{opt}$-overexpressing lines showed improved drought stress tolerance and greater leaf water content than control plants during water-deficit stress conditions.

Figure 24A:
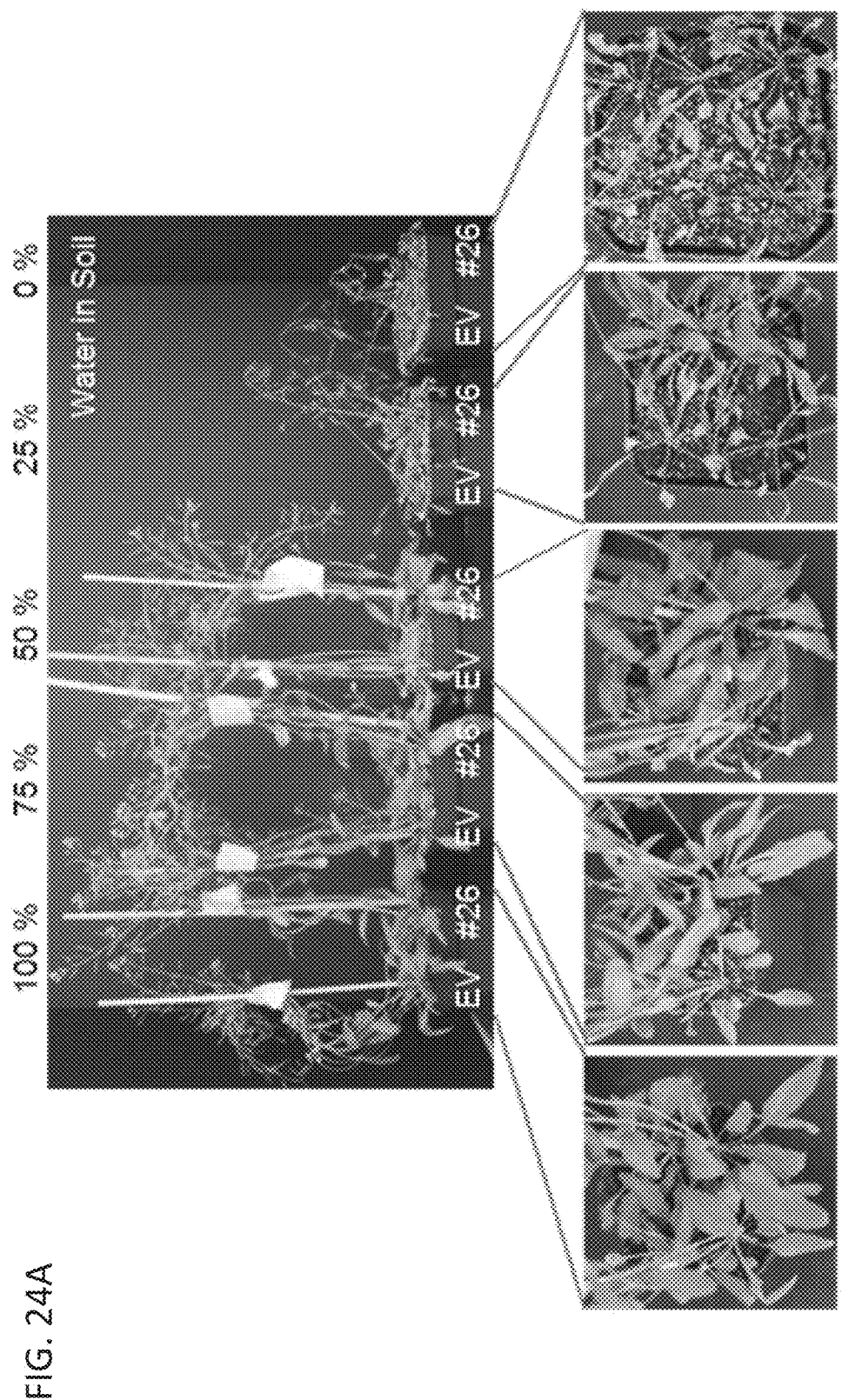
FIGS. 24A-24B illustrate VvCEB1$_{opt}$ overexpressing plants improve drought attenuation under chronic water-controlled conditions.
Figure 24B:
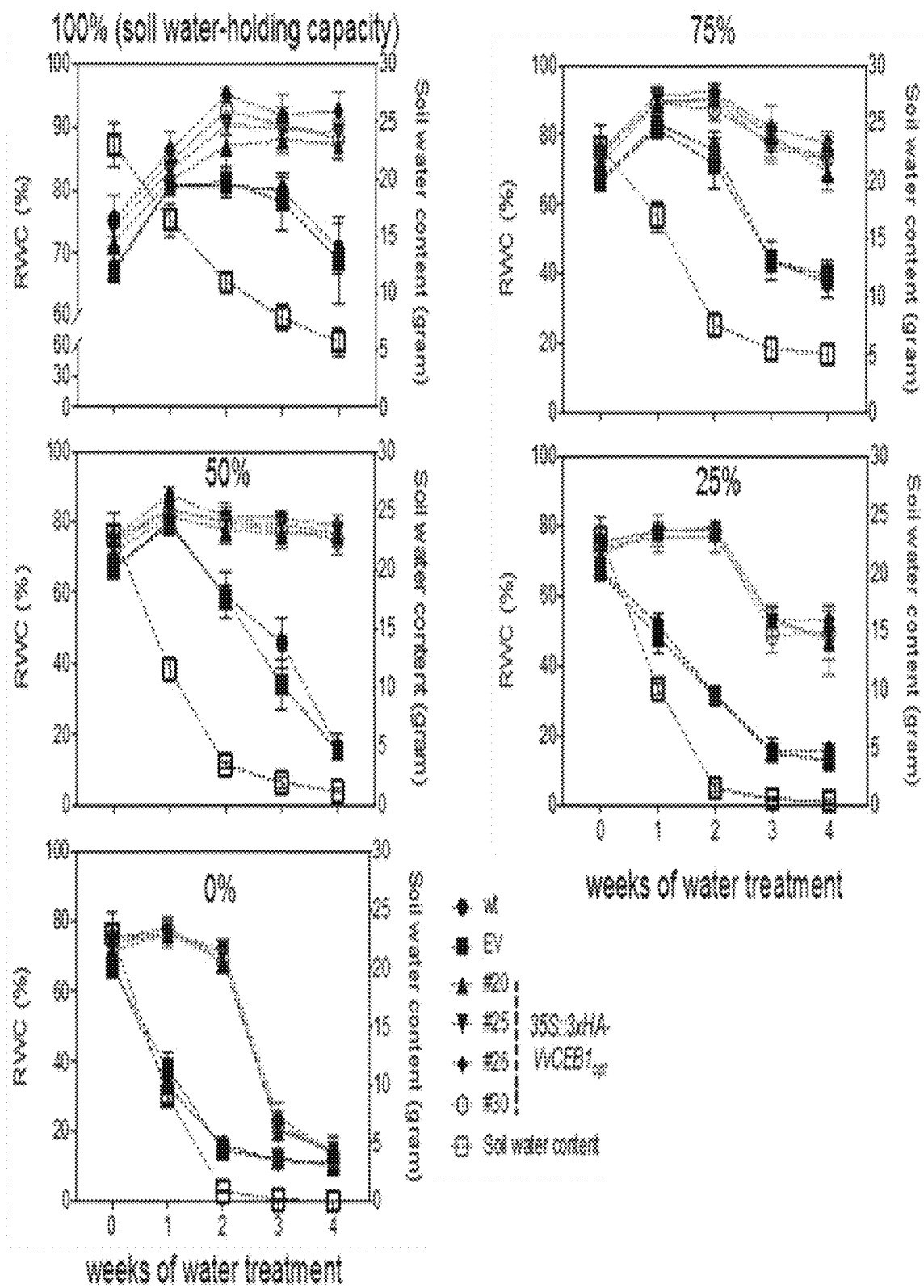
Figure 25A:
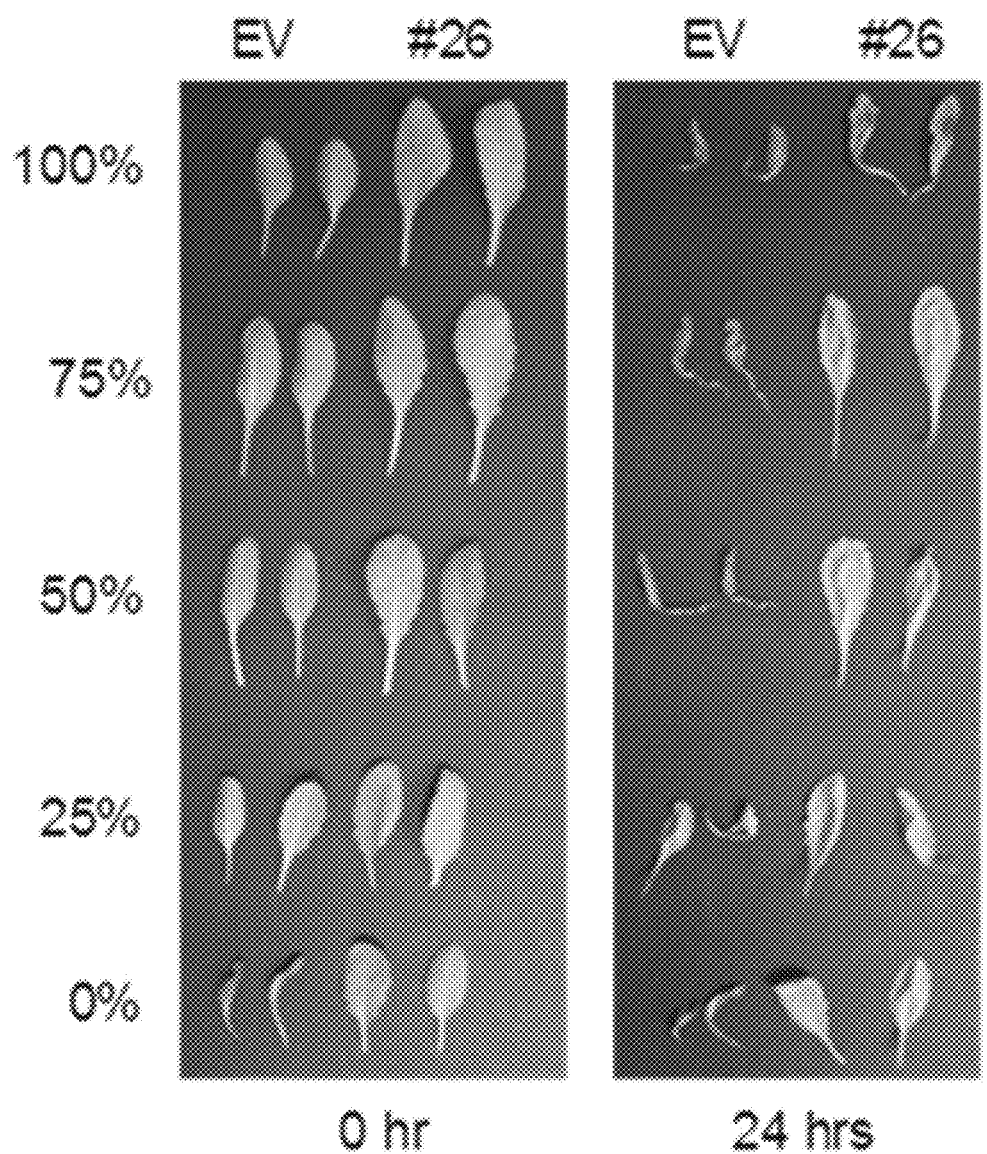
FIGS. 25A-25B illustrate VvCEB1$_{opt}$ overexpressing plants (detached leaves) improve drought stress adaptation under chronic water-controlled conditions.
Figure 25B:
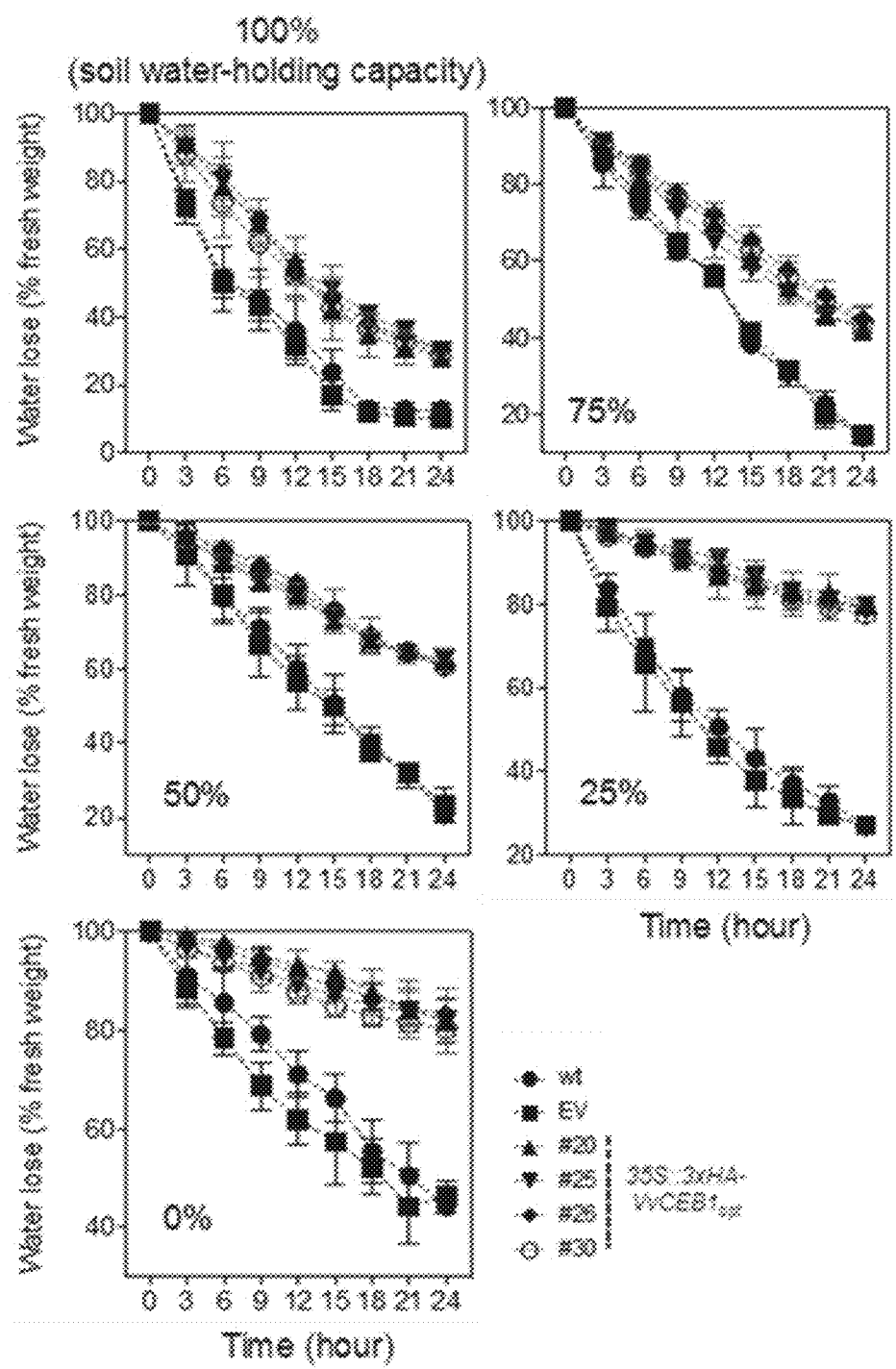

FIGS. 24A-24B illustrate VvCEB1$_{opt}$ overexpressing plants improve drought attenuation under water-controlled conditions. The 14-day-old well-watered four VvCEB1$_{opt}$ overexpressing lines, Col-0 wild type (wt), and empty-vector control plants were grown for 4 weeks under different soil water-holding capacity. Images were captured at 4 weeks after water control (FIG. 24A). Relative water content (RWC) of leaves of four VvCEB1$_{opt}$ overexpressing lines, Col-0 wild type (wt), and empty-vector control plants were measured every week during the study (FIG. 24B). Leaf RWC was calculated by measuring fresh weight, turgid weight, and dry weight (10 leaves for each line, n=4 replicates). In summary, the VvCEB1$_{opt}$-overexpressing lines showed improved drought stress tolerance and greater leaf water content than control plants during water-controlled treatments FIGS. 25A-25B illustrate detached leaves from VvCEB1$_{opt}$ overexpressing plants showed improved drought stress adaptation under water-controlled conditions. The 14-day-old well-watered four VvCEB1$_{opt}$ overexpressing lines, Col-0 wild type (wt), and empty-vector control plants were grown for 2 weeks under different soil water-holding capacity. Detached leaves from four VvCEB1$_{opt}$ overexpressing lines and control lines were air-dried for 24 hours. Water loss from leaves was measured every 3 hours for 24 hours (n=3 replicates). In summary, the VvCEB1$_{opt}$-overexpressing lines showed improved drought stress adaptation by increasing leaf water-holding ability compared to control plants.

Figure 26A:
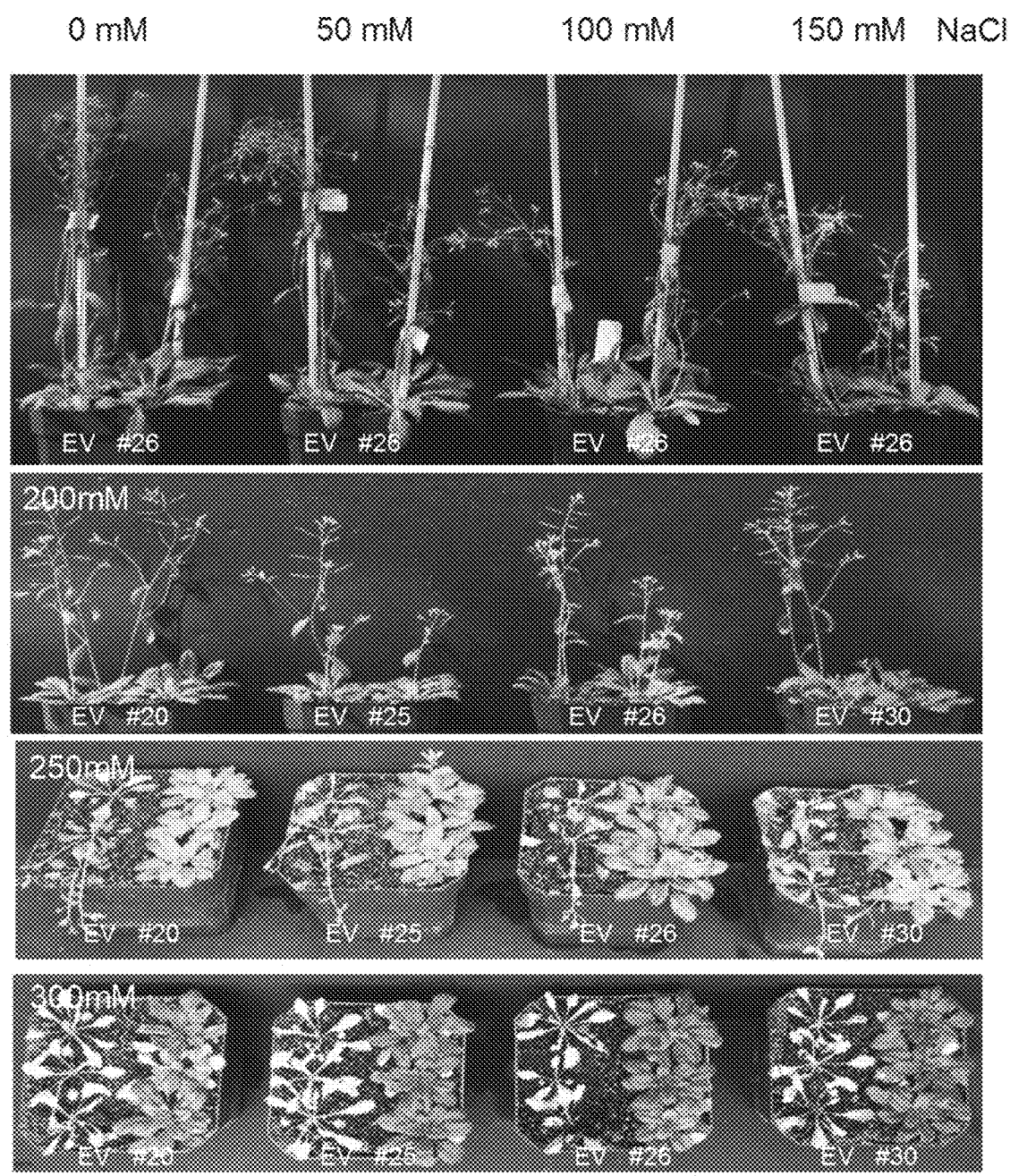
FIGS. 26A and 26B illustrate VvCEB1$_{opt}$ overexpressing plants improve leaf fresh weight under salinity conditions.
Figure 26B:
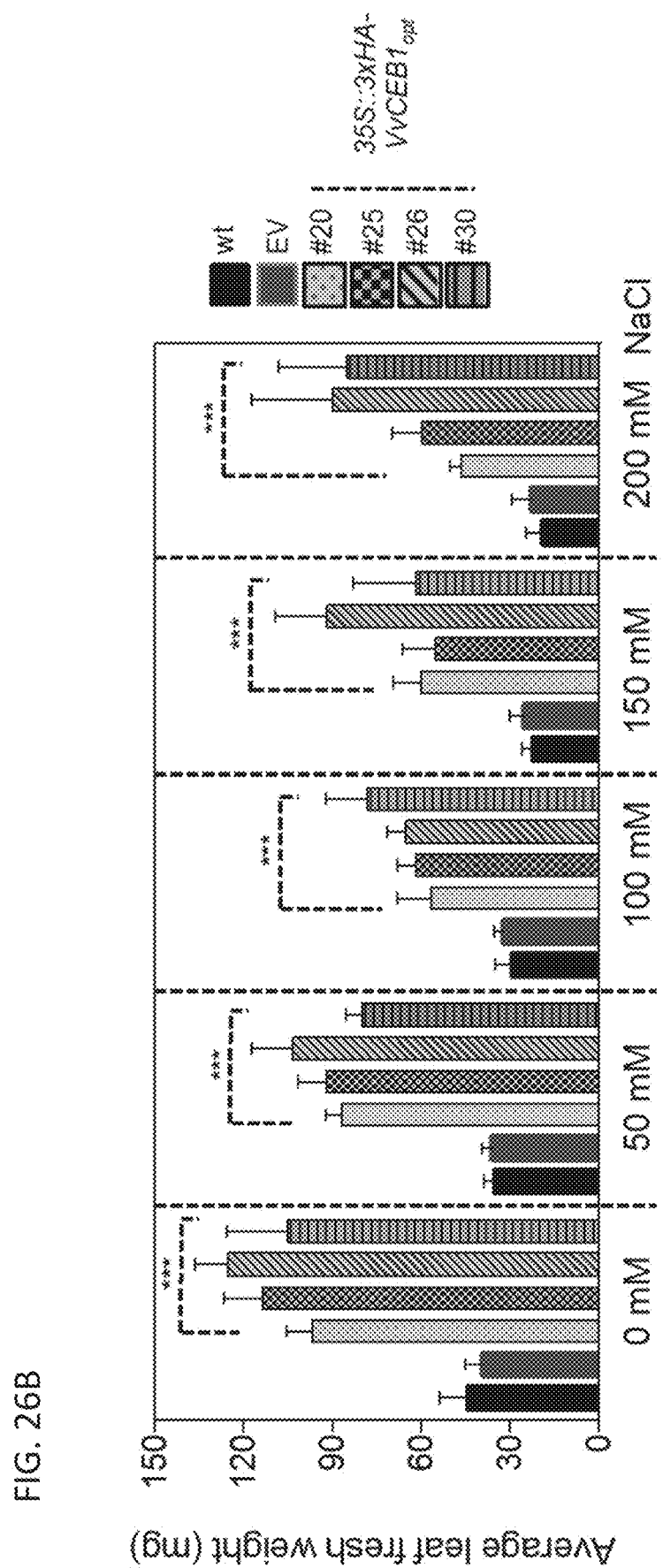

FIGS. 26A and 26B illustrate VvCEB1$_{opt}$ overexpressing plants improve leaf fresh weight under salinity conditions. The 14-day-old well-watered four VvCEB1$_{opt}$ overexpressing lines, Col-0 wild type (wt), and empty-vector control plants were grown for 3 weeks under various salinity concentrations. FIG. 26A provides representative images of VvCEB1$_{opt}$ overexpressing lines and empty-vector control line. FIG. 26B illustrates quantification of average leaf fresh weight (n=4 replicates). Values represent means±s.d., ns=non-significant, ***p<0.001, One-way ANOVA with Dunnett's multiple comparison test. In summary, the VvCEB1$_{opt}$-overexpressing lines showed improved salinity stress tolerance.

Figure 27A:
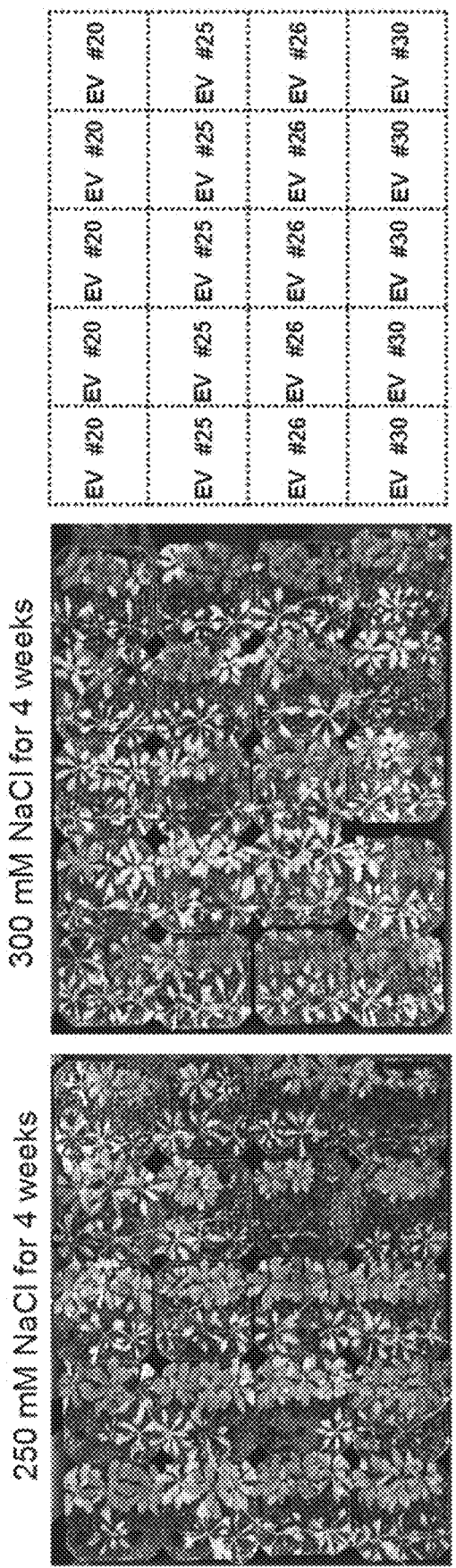
FIGS. 27A-27D illustrate VvCEB1$_{opt}$ overexpressing plants exhibit greater survival rate under high salinity conditions.
Figure 27B:
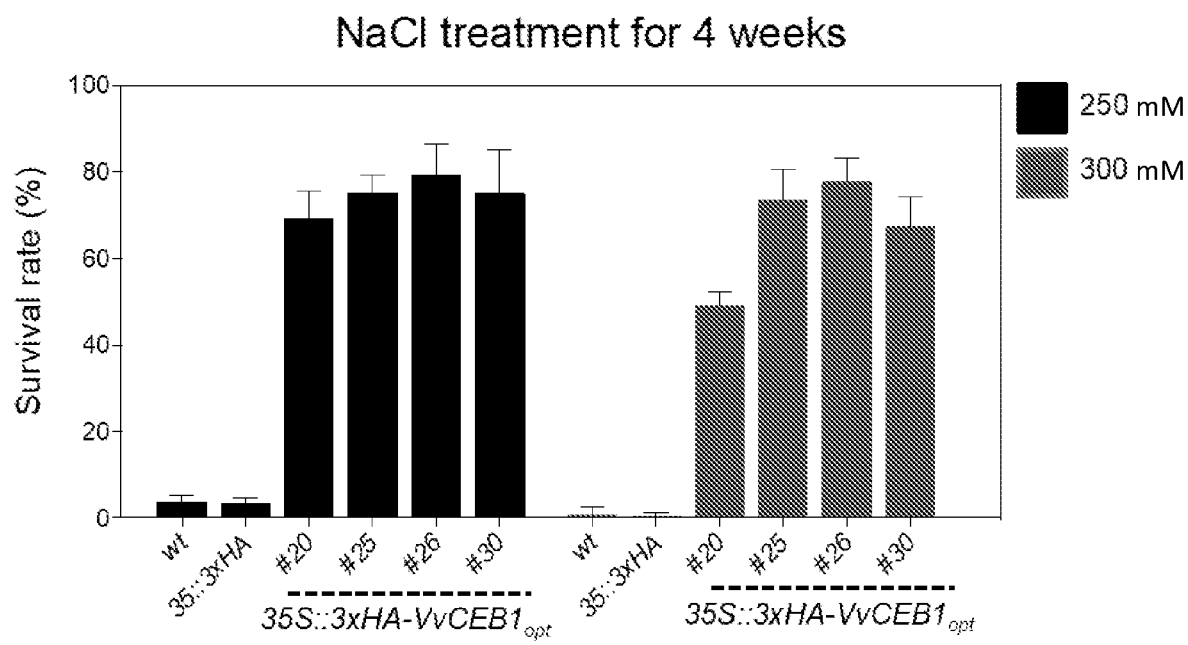
Figure 27D:
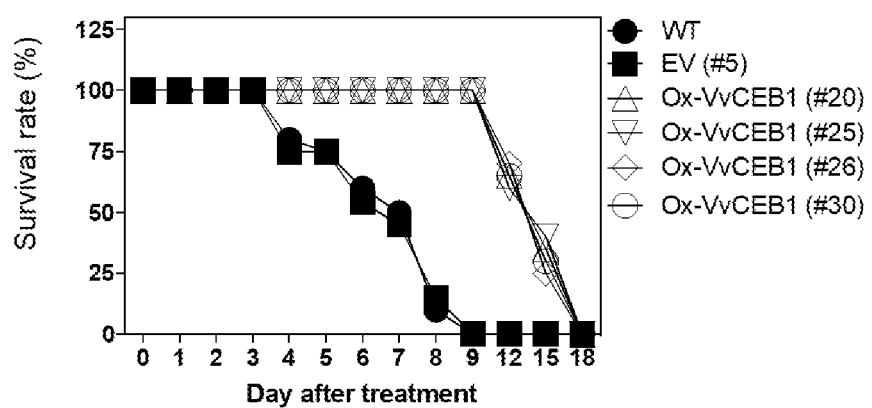
Figure 27C:
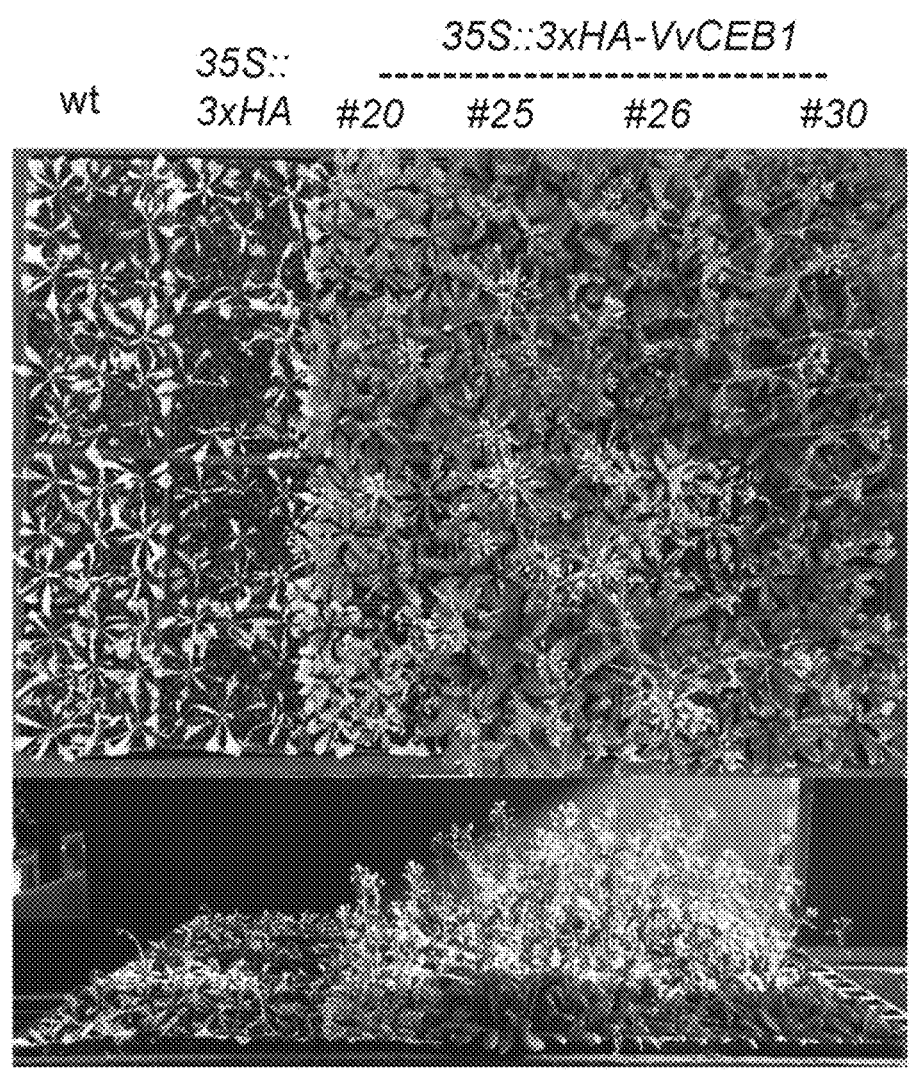

FIGS. 27A-27D illustrate VvCEB1$_{opt}$ overexpressing plants exhibit greater survival rate under high salinity conditions. The 14-day-old well-watered four VvCEB1$_{opt}$ overexpressing lines, Col-0 wild type (wt), and empty-vector control plants were grown for 4 weeks under various salinity concentrations. FIG. 27A provides representative images of four VvCEB1$_{opt}$ overexpressing lines and empty-vector control line photographed at 4 weeks after 250 mM and 300 mM of NaCl treatments. FIG. 27B illustrates quantification of survival rates (n=4 replicates). The 4-week-old well-watered four VvCEB1$_{opt}$ overexpressing lines, Col-0 wild type (wt), and empty-vector control plants were irrigated with 500 mM NaCl solution for 18 days (FIG. 27C). FIG. 27D illustrates quantification of survival rate. Values represent means±s.d. In summary, the VvCEB1$_{opt}$-overexpressing lines showed improved survival rate under high salinity conditions.

Figure 42A:
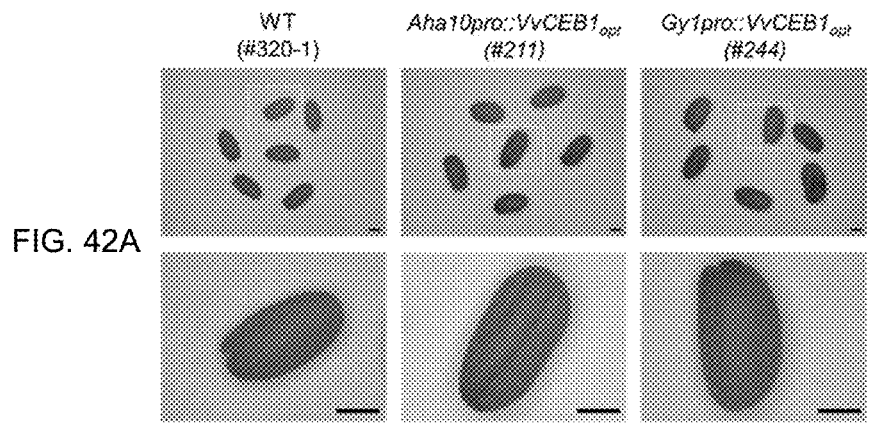
FIGS. 42A-42C illustrate expression of VvCEB1$_{opt}$ by two seed-specific promoters (*Arabidopsis* Aha10 and *Glycine max* Gy1) increased seed size and weight in *Camelina sativa* (cv. Celine).
Figure 42B:
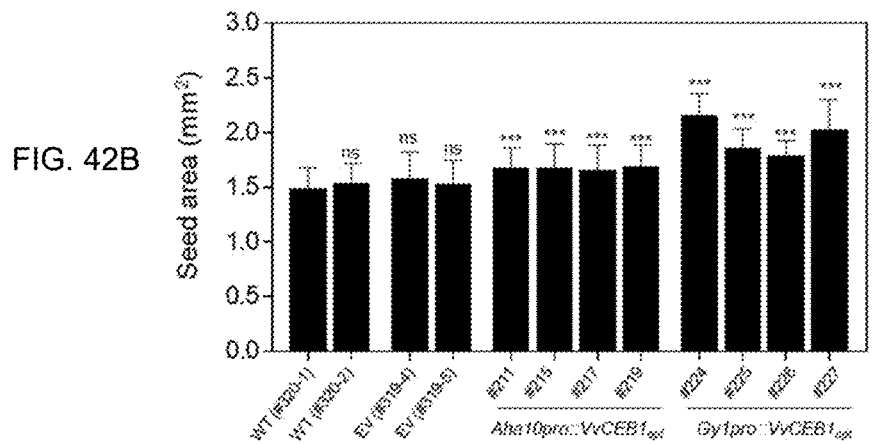
Figure 42C:
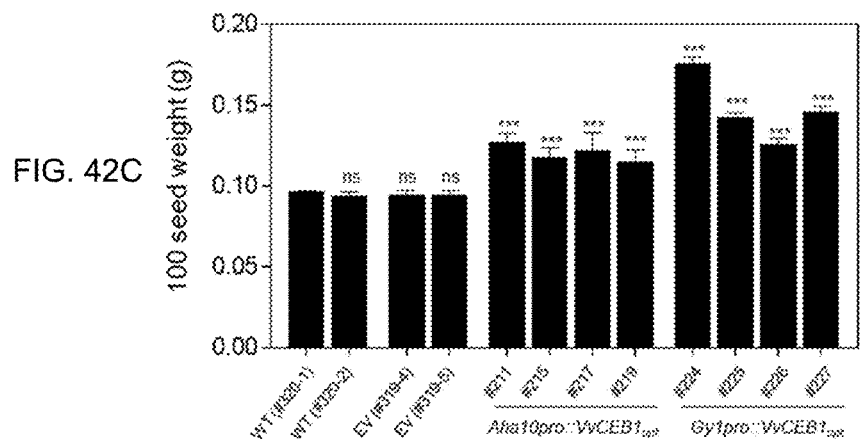

FIGS. 29A-37B illustrate the effect of overexpression of VvCEB1$_{opt}$ on various features/activities and molecules in Arabidopsis. FIGS. 38A-41C illustrate the effect of VvCEB1$_{opt}$ overexpression on various features/activities and molecules in Nicotiana sylvestris (flowering tobacco). FIGS. 42A-42C illustrate expression of VvCEB1$_{opt}$ by two seed-specific promoters (Arabidopsis Aha10 and Glycine max Gy1) increased seed size and weight in Camelina sativa (cv. Celine). Further, FIGS. 43A-43C illustrate VvCEB1$_{opt}$ overexpression increased overall plant size in Oryza sativa (cv. dongjin).

Example 3

Codon Optimized DNA Sequences of VvCEB1 and Orthologous Genes in Plants

This example provides codon optimized DNA sequences of VvCEB1 and orthologous genes in plants.

Figure 28A:
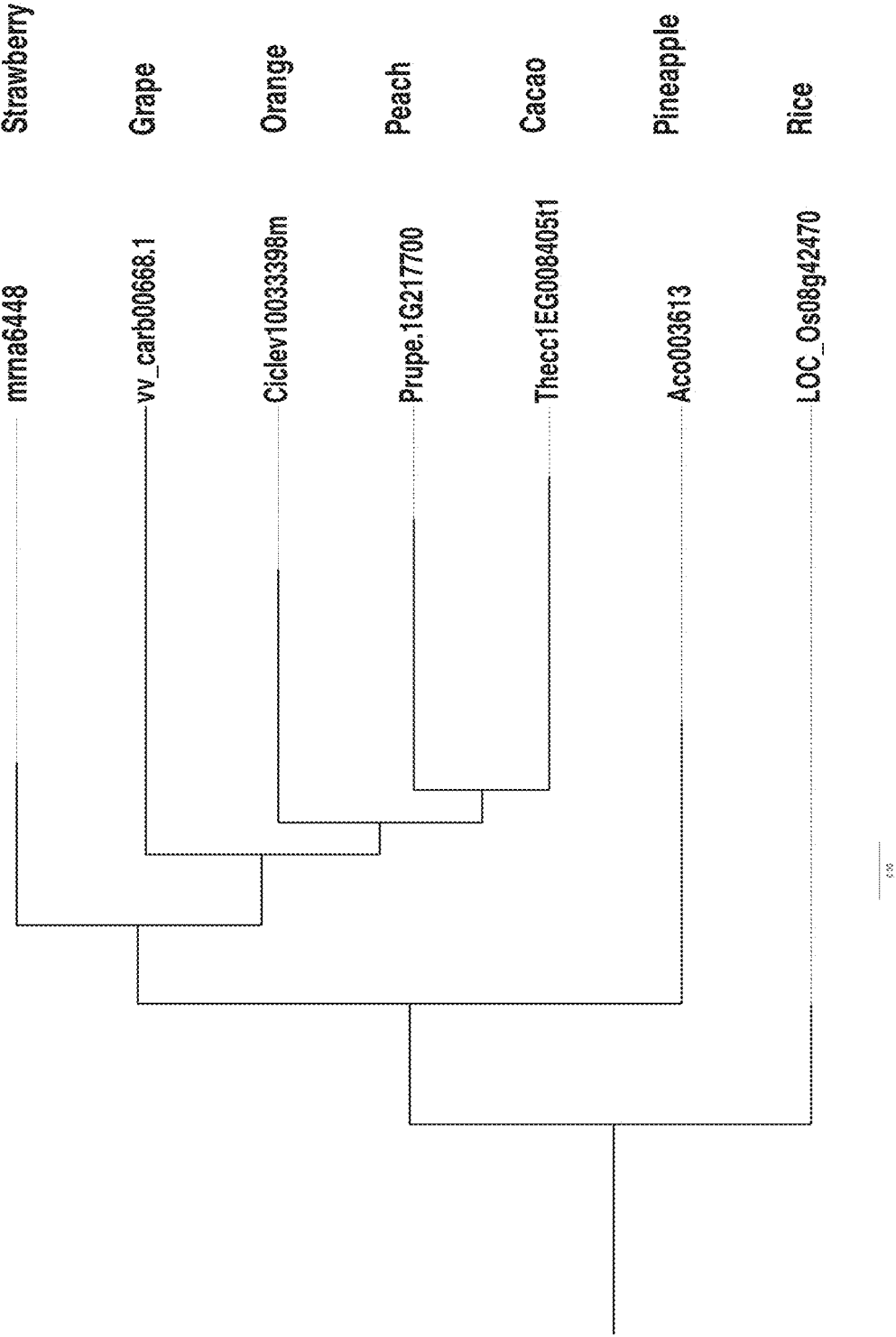
FIGS. 28A and 28B illustrate orthologous genes of VvCEB1 in plant species.

Nucleic-acid-based homology searches were conducted to identify closely related, and therefore putatively functionally related gene orthologues of VvCEB1. FIG. 28A provides a phylogenetic tree of VvCeb1 and its true orthologous genes. The primary goal of the VvCeb1 tree was to identify the most orthologous genes present in other plant species. The coding sequences (CDS) of the primary isoform from each species were used to identify orthologous genes. Then, certain homologous genes that lacked genomic collinearity were removed in order to avoid genes with possibly divergent gene function. The phylogenetic tree was generated using RAxML with the GTR+Γ+I model using over 500 bootstrap replicates.

Figure 28B:
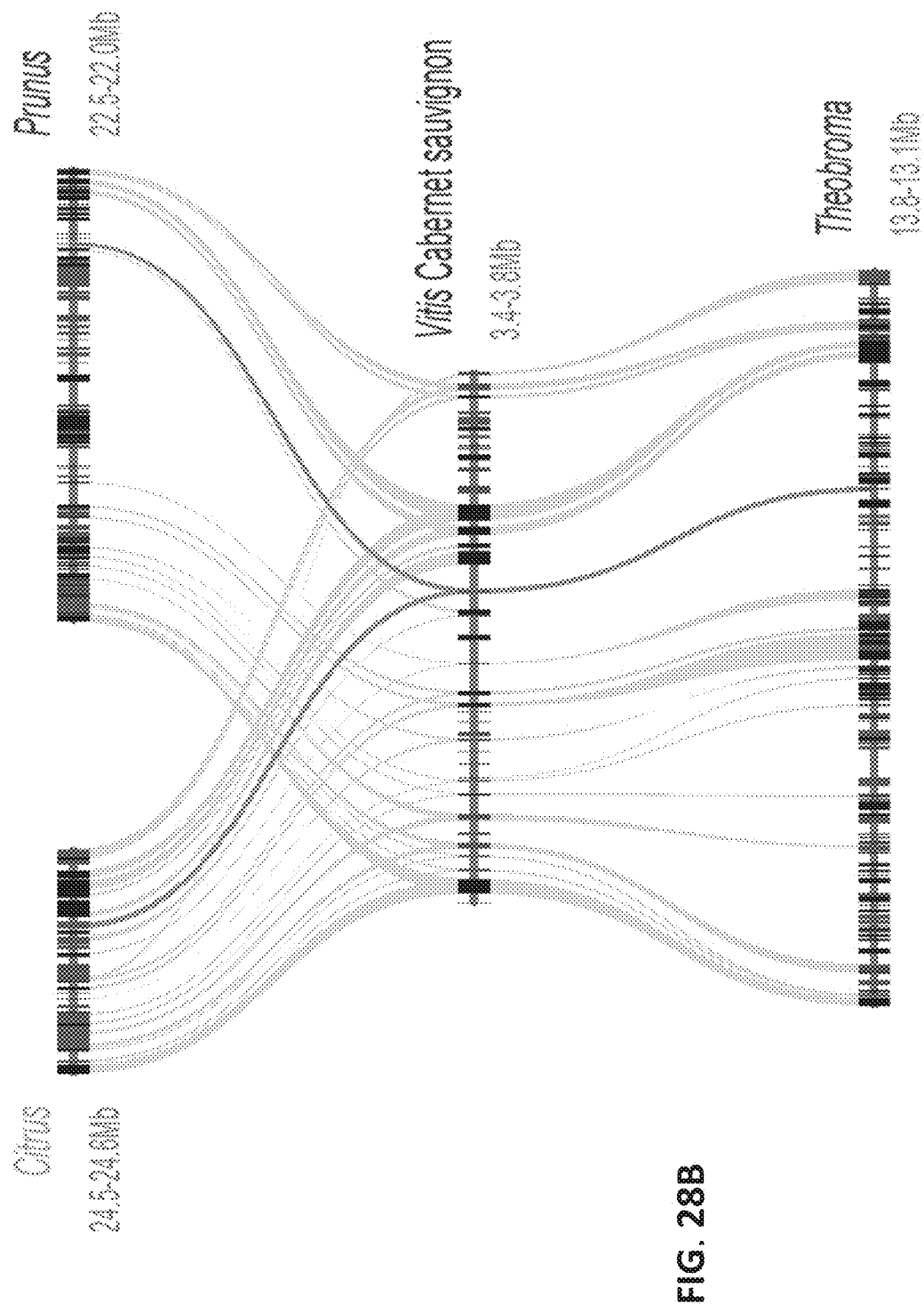
Figure 29A:
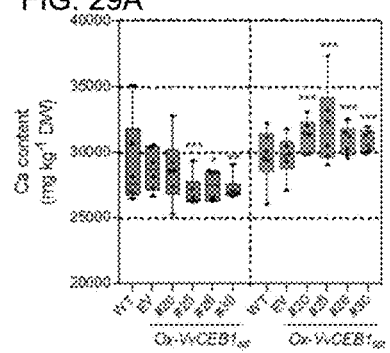
FIGS. 29A-29G illustrate VvCEB1$_{opt}$ overexpression alters the concentration of Ca, K, S, P, and Mo under both normal and salinity treatment conditions in *Arabidopsis* leaves.
Figure 29B:
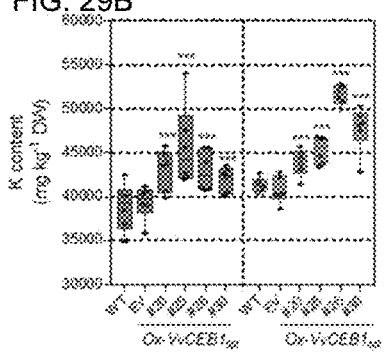
Figure 29C:
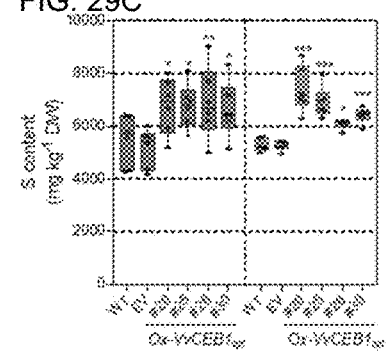
Figure 29D:
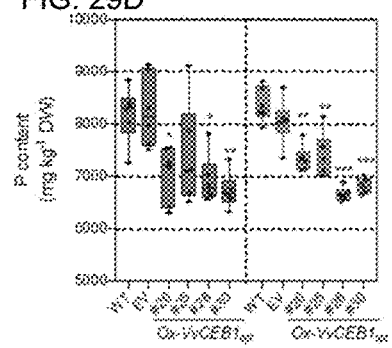
Figure 29E:
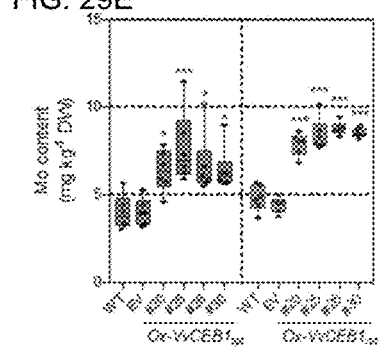
Figure 29F:
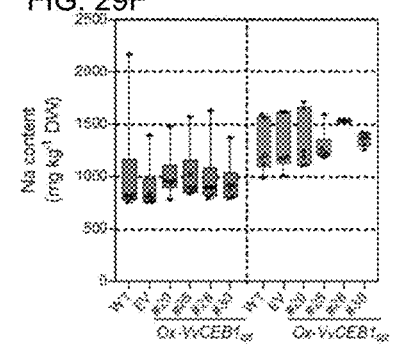
Figure 29G:
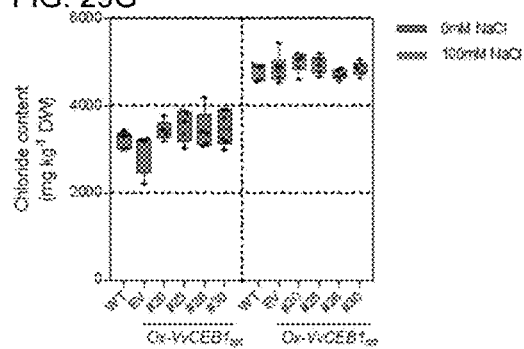
Figure 33A:
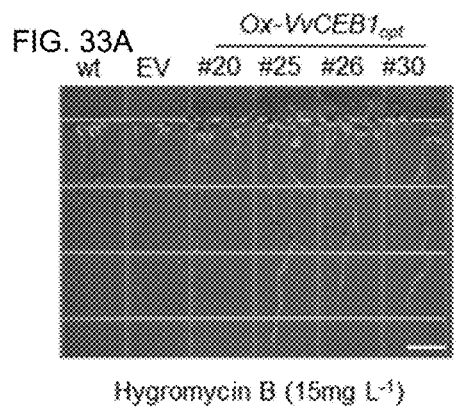
FIGS. 33A-33C illustrate VvCEB1$_{opt}$ overexpression increases hygromycin B tolerance in *Arabidopsis*.
Figure 33B:
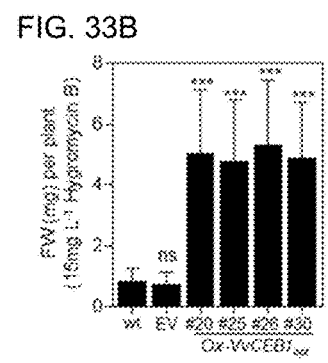
Figure 33C:
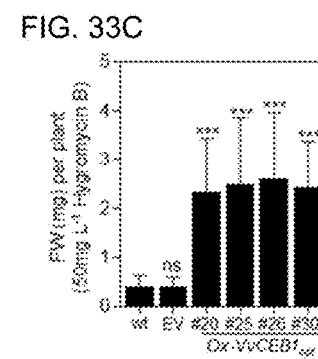
Figure 35A:
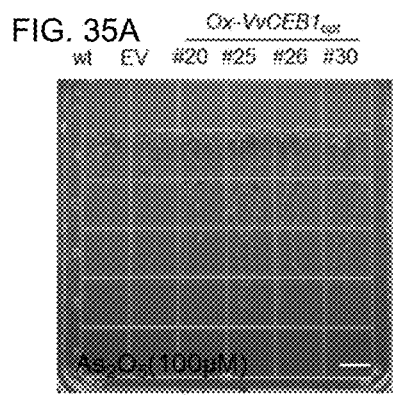
FIGS. 35A-35F illustrate VvCEB1$_{opt}$ overexpression increased arsenic tolerance in *Arabidopsis*.
Figure 35B:
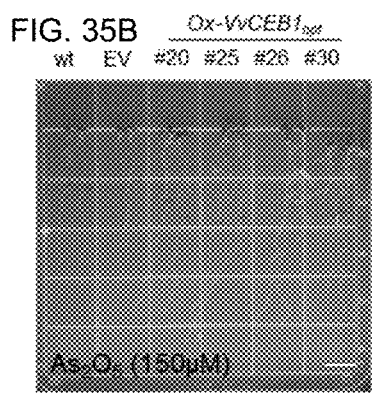
Figure 35C:
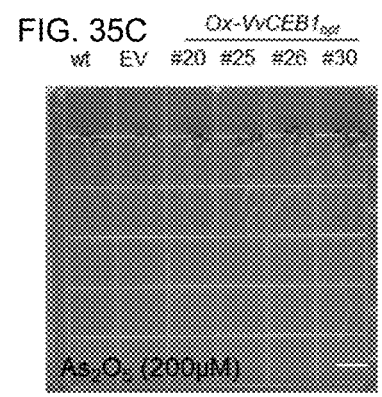
Figure 35D:
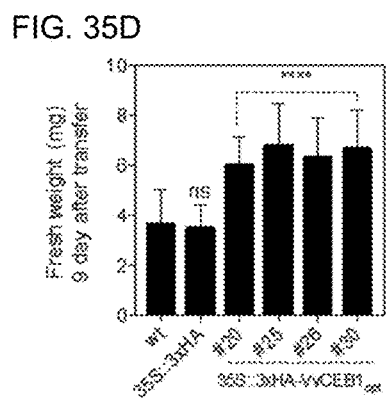
Figure 35E:
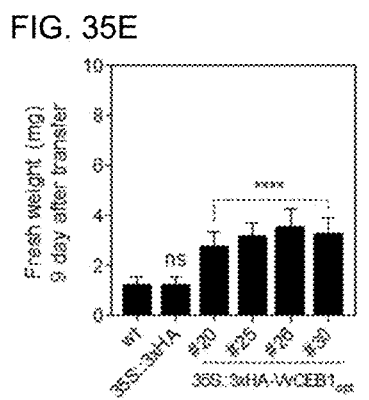
Figure 35F:
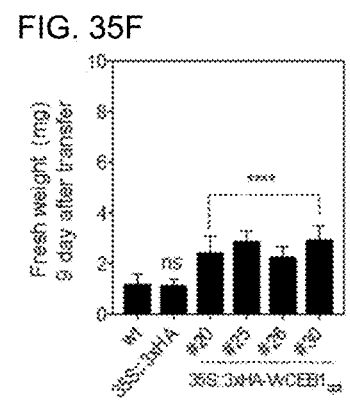
Figure 41A:
FIGS. 41A-41C illustrate VvCEB1$_{opt}$ overexpression increased plant size and seed yield in *Nicotiana sylvestris* (flowering tobacco).
Figure 41B:
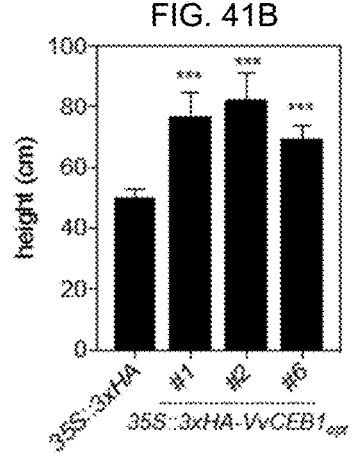
Figure 41C:
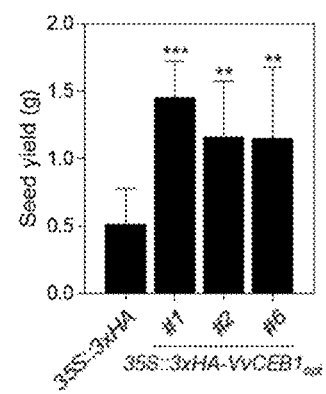

FIG. 28B illustrates the synteny and collinearity of CEB gene orthologs among the genomes of Vitis vinifera (wine grape, Cabernet sauvignon), Prunus persica (peach), Citrus senensis (sweet orange), and Theobroma cacao (Cacao) were evaluated at the genome level by identifying gene sequences anchored to each cognate gene locus (having more than 8 neighboring genes). However, genes within the genomes of these four species were identified in this way could be considered as true orthologs, with the same putative function within each species. In contrast, other species evaluated with complete genome sequences had identifiable orthologs, but the syntenic or collinearity relationships were not conserved evolutionarily.

The following gene orthologues were identified from Vitis vinifera (wine grape, Cabernet sauvignon), Prunus persica (peach), Citrus senensis (sweet orange), and Theobroma cacao (Cacao) and were evaluated at the genome level by identifying gene sequences anchored to each cognate gene locus (having more than 8 neighboring genes). Fragaria vesca (strawberry) and Ananas cosmos us (pineapple) were also included because genes from these species are close orthologues and have fruit that undergo expansion during fruit development like the four species above. The codon-optimized coding sequences derived from these six species were generated in the following manner. Ten different codon-optimized CEB sequences for each species were generated and compared by pair-wise alignments to derive a consensus sequence. This consensus sequence was then converted to IUPAC DNA code (see SEQ ID NOS: 3-9).

In particular, the VvCeb1gene orthologues of sequenced plant and algal genomes in the Phytozome database (see the world wide web at phytozome.jgi.doe.gov/pz/portal) were analyzed. Three species shared the last common ancestor. These orthologues genes (CEBs) were used for further analysis. To optimize codon usage in sequenced genomes of other plant species, codon usage tables were generated from the following species using available gene coding sequences: Aquilegia coerulea, Aquilegia coerulea, Amaranthus hypochondriacus, Amborella trichopoda, Ananas cosmosus, Arabidopsis halleri, Arabidopsis lyrata, Arabidopsis thaliana columbia, Boechera stricta, Brachypodium distachyon, Brachypodium stacei, Brassica rapa, Capsella grandiflora, Capsella rubella, Carica papaya, Chlamydomonas reinhardtii, Citrus clementina, Citrus sinensis, Coccomyxa subellipsoidea, Cucumis sativus, Daucus carota, Dunaliella salina, Eucalyptus grandis, Eutrema salsugineum, Fragaria vesca, Glycine max, Gossypium raimondii, Kalanchoe laxiflora, Kalanchoe marnieriana, Linum usitatissimum, Malus domestica, Manihot esculenta, Medicago truncatula, Micromonas pusilla, Micromonas sp, Mimulus guttatus, Musa acuminata, Oryza sativa, Ostreococcus lucimarinus, Oropetium thomaeum, Panicum hallii, Panicum virgatum, Panicum virgatum, Phaseolus vulgaris, Physcomitrella patens, Populus trichocarpa, Prunus persica, Ricinus communis, Salix purpurea, Selaginella moellendorffii, Setaria italica, Setaria viridis, Solanum lycopersicum, Solanum tuberosum, Sorghum bicolor, Spirodela polyrhiza, Sphagnum fallax, Theobroma cacao, Trifolium pratense, Triticum aestivum, Vitis vinifera, Volvox carteri, and Zea mays. These codon use tables were then used to design the target codon-optimized gene encoding CEBs. The diversity of codon usage in these plant species represented by the IUPAC ambiguity codes for consensus CEBs is indicated in the sequences that follow. The codon-optimized coding sequences were performed by generating codon-optimized coding sequences that had at least a 0.15 frequency, which lack RNA hairpin structures, and lack NGG codons in 5' region of the sequence. Based upon these steps, 10 different codon-optimized CEB sequences were generated for each genome, generated consensus sequence by pair-wise alignment, and converted to sequences to IUPAC DNA code, as shown in the Table below.

| | |
|---|---|
| R | A or G |
| Y | C or T |

| | |
|---|---|
| S | G or C |
| W | A or T |
| K | G or T |
| M | A or C |
| B | C or G or T |
| D | A or G or T |
| H | A or C or T |
| V | A or C or G |
| N | any base |
| . or - | gap |

Thus, the Table above indicates the bases as shown in SEQ ID NOs: 4-9 as below.

CEB1_Vitis vinifera (winegrape)
(SEQ ID NO: 4)
ATGGCVGCCTTYTCTCARCARTCTCAYCAYCTCCAYCCWCAYAARAAYC

TGCGYCTGGAYAGCACSATYGTBCCGAGCATGAGCGCVGTBTTYGAYGA

YGARAARAARCCGACSACSAGCATYAGCTGYTTYAGCGAYGAYCCGGTB

AARAARATYACSCAYTGYAGCAGCATGGGYGCVGARCTGGGYGCVCCGG

GYATGGCVCGYAARCGYAARAAGCGVGAYTTYGARGARGARCGYGAYGT

BGARGARAARAARGGYAARGCVGARAARAARCGYAARAARAARGTBGTB

AARGARGTBCCGAGCGGYTTYGTBCAYGTBCGYGCVCGYCGYGGYGARG

CVACSGAYAGCCAYAGCCTGGCVGARCGYGCVCGYCGYGARAARATYAG

CGARCGYATGAARCTGCTGCARAGCCTGGTBCCGGGYTGYGAYAARCTG

ATYGGYAARACSCTGGTBCTGGAYGARATYATYAAYTAYGTBAARAGCC

TGCARAAYCARGTBGARTTYCTGGTBGGYAARCTGGCVAGCATYAGCCC

GATGCTGATYGGYCAYGARGCVAAYCTGGAYAGCAGCACSCTGCARAGC

GARAAYCTGTGYAGCTTYGGYCCGCCGCTGCCGAGCCTGCTGGCVTGYA

AYAGCACSCARCTGAAYAGCTAYGCVGARACSAGCCTGACSAGCAGCTT

YAGCCTGCARCARGAYCAYCTGAGCAGCGTBGTBAGCCARAAYGAYGGY

ATYATYCTGTGGGAYATGGAYGAYCARGARCARAGCCTGCTGGAYCART

AYGGYTTYAGCAAYCGYTAYAGCTTY

CEB1_Citrus sinensis (sweet orange)
(SEQ ID NO: 5)
ATGGTBWSNGARGARGARGGYGARMGHAARGGYAARAARCARMGHAARC

ARAAYGGYAGCGARGCVAARAARCARAGCAARGTBGCVGCVGCVTTYGC

VGARCGYGTBCARCGYAAYGGYGTBCGYGTBAARGCVCGYCGYGGYGAR

GCVACSGAYAGCCAYAGCCTGGCVGARCGYGCVCGYCGYGARAARATYA

AYGTBCGYATGAARCTGCTGCARAGCCTGGTBCCGGGYTGYGAYCARAT

YAAYGGYAARGCVCAYGCVCTGGAYGARATYATYAARTAYGTBCARCTG

CTGCARAAYCARGTBGARTGYCTGGCVGCVGARCTGGCVTTYGTBGAYG

CVATGCTGTAYGAYGAYTGYGARCTGAAYCCGAGCACSAAYCCGTGYGC

VAGCGAYCARCGYCTGTGYTGYCTGGARCCGCCGAGCAGCGTBCCGTTY

CGYAGCCTGGCVGAYGCVGCVCCGACSCCGTGYACSTTYGCVAGCCTGC

TGCTGACSGARGAYCARAARGCVAGCCTGATYCCGCARGTBCARGAYGG

YGGYAGCTTYGARGAYGTBGGYAARCAYCCGGCVCGYCTGGAYCAYAGC

TGYACSTTYTRA

CEB1_Prunus persica (Peach)
(SEQ ID NO: 6)
ATGGTBAGCGARGARGARGGYGARCGCAARGGYAARAARCARCGCAARC

ARAAYGGYAGCGARGCVAARAARCARAGCAARGTBGCVGCVGCVTTYGC

VGARCGYGTBCARCGYAAYGGYGTBCGYGTBAARGCVCGYCGYGGYGAR

GCVACSGAYAGCCAYAGCCTGGCVGARCGYGCVCGYCGYGARAARATYA

AYGTBCGYATGAARCTGCTGCARAGCCTGGTBCCGGGYTGYGAYCARAT

YAAYGGYAARGCVCAYGCVCTGGAYGARATYATYAARTAYGTBCARCTG

CTGCARAAYCARGTBGARTGYCTGGCVGCVGARCTGGCVTTYGTBGAYG

CVATGCTGTAYGAYGAYTGYGARCTGAAYCCGAGCACSAAYCCGTGYGC

VAGCGAYCARCGYCTGTGYTGYCTGGARCCGCCGAGCAGCGTBCCGTTY

CGYAGCCTGGCVGAYGCVGCVCCGACSCCGTGYACSTTYGCVAGCCTGC

TGCTGACSGARGAYCARAARGCVAGCCTGATYCCGCARGTBCARGAYGG

YGGYAGCTTYGARGAYGTBGGYAARCAYCCGGCVCGYCTGGAYCAYAGC

TGYACSTTYTRA

CEB1_Theobroma cacao (Cacao)
(SEQ ID NO: 7)
ATGAGCGCRTTYCCAAAYCARCAYTTGCCWAGCGTSATYAAYAGCTTYG

TBGARCCGAAYACSCTGGAYTGYATGAGCGGYTTYCTGCGYGARGARAG

CAGCGCVACSAARACSTGYTTYAGCAGCAAYTTYCCGGAYGCRTGYTTY

CARGARATYATYAGCGGYCARTAYGCVCARAAYCAYGTBGCVACSACSC

TGAAYGARGTBAAYCTGGAYGTBCCGTTYACSTTYCCGGTBATYCCGTT

YGCVATYGCVAAYCARGARATYGAYAGCACSACSATYCCGATGCTGCTG

GARCTGGARCACGYGGYGAYGAYCAYCARATYACSGGYGARGTBAGCG

CVAGCGARAAYAARCGYAARAARGTBGARACSAARGTBGARCGYGARAA

RAARCGYGARAARAARCAYAARAAYATYCGYGGYCTGCARCARGCVAAR

GARAGCCGYCTGAARCCGGAYATYAARAAYAARAARAARGTBCCGGARA

ARGTBGARACSGAYAAYTAYGCVCAYGTBCGYGCVCGYCGYGGYGARGC

VACSGAYAARCAYAGCCTGGCVGARCGYGTBCGYCGYGARAARATYAGC

GTBCGYATGAARCTGCTGCARAGCCTGGTBCCGGGYTGYGAYAARCTGA

CSGGYAARACSCARATGCTGGAYGARATYATYCGYTAYGTBCARTGYCT

GCARCAYCARGTBGARTTYATYAGCACSGARGCVGARGARTTYAGCAGC

CTGGARAARGCVTGGCCGCTGAGCTTYGTBGARAGCAGCAGCACSGGYC

ARTTYAARGCVTTYACSGCVGCVACSCCGGCVCCGACSAGCAGCCTGCT

GCAYCARACSGAYGCVCARCARCGYCTGAAYATYACSACSCGYGAYAAR

GCVATYTGYTAYGGYAARCGYCAYATYCGYACSAGCAGCAGCCTGGCVT

RA

CEB1_Ananas comosus (Pineapple)
(SEQ ID NO: 8)
ATGGARTTRTTYAGCAATCARCACCACCARGCGAGCCTGCTAAGTCCGA

GCAAYCTGCCGAAYAGCTTYATGGARAARAAYTTYCCGCCGCARCARCT

GGGYGARATGAGCAAYGARACSAGCTAYTGYTTYCCGTAYTGYTAYCTG

AGCGARGCVATYCCGGARTTYAGCAAYAAYAGCGAYAGCACSGCVCGYG

-continued

```
CVTAYGARAGCAGCAGCAGCCTGGAYACSGTBCGYAAYGCVAGCAGCGC

VGGYACSCARATGAGCCAYAGCGCVGTBATYACSGAYCCGGGYAGCCCG

AGCGGYAARCGYCGYAARAAYCGYGAYAGCACSAGCCTGTGYCTGGCVC

CGCTGAGCAAYGAYGCVATGGARAGCAARACSAARAACARAARCGYCC

GAAYGGYGGYCTGAARAAGGTBGARGARAARAARCCGAARGGYGAYGAR

ATYAARCAYAARGARGTBTGYGGYGARCCGCAYGARGGYTAYATYCAYG

TBCGYGCVCGYCGYGGYCARGCVACSGAYAGCCAYAGCCTGGCVGARCG

YGTBCGYCGYGARAARATYAAYAARCGYATGAARATGCTGCARAGCCTG

GTBCCGGGYTGYGAYGGYGTBAGCGGYAARGCVCTGATGCTGGAYGARA

TYATYAAYTAYGTBCARAGCCTGCARAAYCARGTBGARTTYCTGAGCAT

GAARCTGGCVAGCATGAAYCCGATGTTYGAYGARTTYGGYGTBGAYTTY

GARTGYCTGATGAAYCAYCCGGARGTBGCVCGYACSAARGCVAARTGYC

ARCAYACSCTGCTGCTGATYTGGCCGATYAGCCTGGGYTTYGAYATYGA

YCTGACSCTGTAYAGCATGCCGCAYGARCARGTBCCGACSGTBGAYCAR

ACSAAYCAYAGCCARGCVACSCCGAGCGARGCVACSACSGTBAAYTAYC

ARATGGTBGAYAAYAGCACSCCGATYCTGCARCAYGGYCARGGYCCGAC

STAYTTYCCGCARGARGCVAAYAGCACSCGYCAYAARGAYGGYACSTRA
```

CEB1_Fragaria vesca (Strawberry)

(SEQ ID NO: 9)

```
ATGGGYGARGCDGTWTAYGGYATYGGCAGAGTWAAAGCAACBCTGAARC

TGAGCAGCCCGCTGCTGAGCACSCCGCTGATYAGCAGCCGYATGATGGT

BCGYCGYAARGCVGCVAGCACSATGCGYATYATGCTGCCGCTGGCVGCV

GGYACSCCGAAYAGCACSAAYACSAAYAAYCTGCAYTTYAGCCARAGCC

AYTAYCCGAGCGARCCGCTGGTBGARCARATGAAYATYCCGGGYGAYCA

RAGCGCVCGYGTBGCVGARAGCAGCAGCTGYATYGAYCARAGCAGCGCV

AARATYGCVACSTTYAGCGAYAAYGARCCGAGCGTBACSAARAARCARA

GCCCGGARAGCAGCAGCGTBGTBGAYAARCTGGARACSGGYGARCARGT

BACSCARAARGTBACSACSCCGATYGARCGYAARCGYCGYACSCGYAAY

TGYAGCAGCCCGAGCAGCGCVCARAGCAARGTBAARAARCARAARAARG

CVGARGARGARAARAARAGCAARGCVGARAARAARGARCARAARAARGC

VGTBCARGARGTBGARCCGCCGACSGGYTAYATYCAYGTBCGYGCVCGY

CGYGGYCARGCVACSGAYAGCCAYAGCCTGGCVGARCGYGTBCGYCGYG

ARAARATYAGCGARCGYATGAARATGCTGCARCGYCTGGTBCCGGGYTG

YGAYAARGTBACSGGYCGYGCVGTBATGCTGGAYGARATYATYAAYTAY

GTBCARAGCCTGCARAAYCARGTBGARTTYCTGAGCATGAARCTGGCVA

GCGTBAAYCCGATGTTYTAYGARTTYGGYCCGGAYCTGGGYGAYCTGAT

GGTBAARCARGARGCVAGCCCGTTYAGCACSGGYCCGCARTGYAGCCCG

ACSCARCCGACSAAYTTYGCVGAYACSAGCACSACSGCVGCVACSACSA

CSTTYACSGCVGCVACSAAYAAYTAYCCGTTYCTGGAYAGCCTGCTGCA

YCARAGCCCGCYCCGACSGCVTTYCAYCARGAYAAYGARAGCCTGCTG

TGGGAYGGYGARGAYCARCGYCARAGCTTYCTGAAYCCGAGCGGYTTYA

AYAAYCTGTGYAGCTTYAAYTRA.
```

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

We claim:

1. A method of enhancing plant succulence, comprising:

inserting into a vector construct a nucleic acid sequence with at least 95% sequence identity to any one of SEQ ID NOS: 3-9 encoding a basic helix-loop-helix transcription factor cell elongation bHLH protein (CEB1);

transforming a plant cell with the vector construct;

expressing the CEB1 which is encoded by the nucleic acid sequence with at least 95% sequence identity to any one of SEQ ID NOS: 3-9 in the plant cell; and producing a plant from the transformed plant cell, wherein the plant has enhanced plant succulence as compared to a control plant lacking the vector construct, wherein the plant having enhanced plant succulence has one or more of reduced hypocotyl length as compared to the control plant, reduced plant leaf water loss as compared to the control plant, reduced leaf stomatal aperture as compared to the control plant and reduced leaf stomatal density as compared to the control plant.

2. The method of claim 1, wherein the nucleic acid sequence is set forth in SEQ ID NO: 3.

3. The method of claim 1, wherein the plant with enhanced plant succulence has reduced hypocotyl length as compared to the control plant, reduced plant leaf water loss as compared to the control plant, reduced leaf stomatal aperture as compared to the control plant, and reduced leaf stomatal density as compared to the control plant.

4. The method of claim 1, wherein the method is used to produce the plant having enhanced plant succulence further comprising (a) decreased molybdenum (Mo), sulfur (S), and/or chloride (Cl) content within vegetative tissues as compared to the control plant;

(b) decreased phosphorous (P) content within vegetative tissues as compared to the control plant;

(c) reduced sodium uptake as compared to the control plant;
(d) an acidified apoplast as compared to the control plant;
(e) tolerance to acidic conditions in its rooting media as compared to the control plant;
(f) Hygromycin B tolerance as compared to the control plant;
(g) cadmium tolerance as compared to the control plant;
(h) arsenic tolerance as compared to the control plant;
(i) aluminum tolerance as compared to the control plant;
(j) drought tolerance as compared to the control plant;
(k) salinity tolerance as compared to the control plant;
(l) ionic stress tolerance as compared to the control plant; and/or
(m) cesium tolerance as compared to the control plant.

5. The method of claim 1, wherein the method is used to produce the plant having enhanced plant succulence and one or more of:
increased plant tolerance to salinity and related salts that impose an ionic stress as compared to the control plant;
increased plant tolerance to mannitol, PEG, and related osmotic agents that impose an osmotic stress as compared to the control plant;
increased plant tolerance to acute and/or chronic water-deficit (drought) stress imposed by a lack of water availability as compared to the control plant; and/or
increased plant instantaneous or integrated water-use efficiency by reducing stomatal aperture and density as compared to the control plant.

6. A method of producing a transgenic plant with enhanced plant succulence, comprising:
transforming a plant cell or tissue with a plant transformation vector comprising an isolated polynucleotide sequence having a plant promoter and a polynucleotide sequence with at least 95% sequence identity to any one of SEQ ID NOS: 3-9 encoding a basic helix-loop-helix transcription factor cell elongation bHLH protein (CEB1);
expressing the CEB1 which is encoded by the polynucleotide sequence with at least 95% sequence identity to any one of SEQ ID NOS: 3-9 in the plant cell; and
producing the transgenic plant from the transformed plant cell, wherein the transgenic plant has enhanced plant succulence as compared to a control plant lacking the vector construct, wherein the transgenic plant having enhanced plant succulence has one or more of reduced hypocotyl length as compared to the control plant, reduced plant leaf water loss as compared to the control plant, reduced leaf stomatal aperture as compared to the control plant and reduced leaf stomatal density as compared to the control plant.

7. The method of claim 6, wherein the polynucleotide sequence is set forth in SEQ ID NO: 3.

8. The method of claim 1, wherein the nucleic acid sequence is set forth in SEQ ID NO: 3, SEQ ID NO: 4, SEQ ID NO: 5, SEQ ID NO: 6, SEQ ID NO: 7, SEQ ID NO: 8, or SEQ ID NO: 9.

9. The method of claim 6, wherein the polynucleotide sequence is set forth in SEQ ID NO: 3, SEQ ID NO: 4, SEQ ID NO: 5, SEQ ID NO: 6, SEQ ID NO: 7, SEQ ID NO: 8, or SEQ ID NO: 9.

10. The method of claim 1, wherein the plant with enhanced plant succulence has reduced leaf stomatal aperture as compared to the control plant and/or reduced leaf stomatal density as compared to the control plant.

11. The method of claim 1, wherein the method is used to produce the plant having enhanced plant succulence and increased plant tolerance to acute and/or chronic salinity stress imposed by irrigation with salt solutions as compared to the control plant.

12. The method of claim 6, wherein the transgenic plant with enhanced plant succulence has reduced hypocotyl length as compared to the control plant, reduced plant leaf water loss as compared to the control plant, reduced leaf stomatal aperture as compared to the control plant, and reduced leaf stomatal density as compared to the control plant.

13. The method of claim 6, wherein the transgenic plant with enhanced plant succulence has reduced leaf stomatal aperture as compared to the control plant and/or reduced leaf stomatal density as compared to the control plant.

14. The method of claim 6, wherein the method is used to produce the transgenic plant having enhanced plant succulence further comprising
(a) decreased molybdenum (Mo), sulfur (S), and/or chloride (Cl) content within vegetative tissues as compared to the control plant;
(b) decreased phosphorous (P) content within vegetative tissues as compared to the control plant;
(c) reduced sodium uptake as compared to the control plant;
(d) an acidified apoplast as compared to the control plant;
(e) tolerance to acidic conditions in its rooting media as compared to the control plant;
(f) Hygromycin B tolerance as compared to the control plant;
(g) cadmium tolerance as compared to the control plant;
(h) arsenic tolerance as compared to the control plant;
(i) aluminum tolerance as compared to the control plant;
(j) drought tolerance as compared to the control plant;
(k) salinity tolerance as compared to the control plant;
(l) ionic stress tolerance as compared to the control plant; and/or
(m) cesium tolerance as compared to the control plant.

15. The method of claim 6, wherein the method is used to produce the transgenic plant having enhanced plant succulence and one or more of:
increased plant tolerance to salinity and related salts that impose an ionic stress as compared to the control plant;
increased plant tolerance to mannitol, PEG, and related osmotic agents that impose an osmotic stress as compared to the control plant;
increased plant tolerance to acute and/or chronic water-deficit (drought) stress imposed by a lack of water availability as compared to the control plant; and/or
increased plant instantaneous or integrated water-use efficiency by reducing stomatal aperture and density as compared to the control plant.

* * * * *

SEQUENCE LISTING

```
<160> NUMBER OF SEQ ID NOS: 9

<210> SEQ ID NO 1
<211> LENGTH: 810
<212> TYPE: DNA
<213> ORGANISM: Vitis vinifera
<220> FEATURE:
<221> NAME/KEY: CDS
<222> LOCATION: (1)..(810)

<400> SEQUENCE: 1 atg gca gcc ttt tct cag cag tct cac cac ctc cac ccc cac aaa aat    48
Met Ala Ala Phe Ser Gln Gln Ser His His Leu His Pro His Lys Asn
1               5                   10                  15 tta agg ctg gac tcg acc att gtg cca agc atg tct gca gta ttt gat    96
Leu Arg Leu Asp Ser Thr Ile Val Pro Ser Met Ser Ala Val Phe Asp
            20                  25                  30 gat gag aag aaa ccc acc acc tcc atc tcc tgt ttt tct gat gat cct   144
Asp Glu Lys Lys Pro Thr Thr Ser Ile Ser Cys Phe Ser Asp Asp Pro
        35                  40                  45 gtg aag aag atc acg cat tgt tca tcc atg ggg gct gag ctt ggg gct   192
Val Lys Lys Ile Thr His Cys Ser Ser Met Gly Ala Glu Leu Gly Ala
    50                  55                  60 cca ggg atg gcg agg aag aga aag aag gct gat ttt gag gaa gag agg   240
```

```
Pro Gly Met Ala Arg Lys Arg Lys Lys Ala Asp Phe Glu Glu Glu Arg
 65                 70                  75                  80 gac gtg gag gag aag aag ggt aaa gct gag aag aag agg aag aag aaa      288
Asp Val Glu Glu Lys Lys Gly Lys Ala Glu Lys Lys Arg Lys Lys Lys
                 85                  90                  95 gtg gtg aaa gag gtc cca agt ggg ttt gtt cat gtg aga gca agg agg      336
Val Val Lys Glu Val Pro Ser Gly Phe Val His Val Arg Ala Arg Arg
            100                 105                 110 ggt gaa gca aca gac agt cac agc ctt gct gaa agg gca aga aga gag      384
Gly Glu Ala Thr Asp Ser His Ser Leu Ala Glu Arg Ala Arg Arg Glu
        115                 120                 125 aaa atc agt gaa aga atg aag ctt ttg caa tca ctt gtt cct ggt tgt      432
Lys Ile Ser Glu Arg Met Lys Leu Leu Gln Ser Leu Val Pro Gly Cys
    130                 135                 140 gac aag ctc att ggc aag act ctc gta ctg gat gag ata atc aat tat      480
Asp Lys Leu Ile Gly Lys Thr Leu Val Leu Asp Glu Ile Ile Asn Tyr
145                 150                 155                 160 gtc aag tcc ctg cag aat caa gta gag ttc ctt gtg ggc aag ctt gct      528
Val Lys Ser Leu Gln Asn Gln Val Glu Phe Leu Val Gly Lys Leu Ala
                165                 170                 175 tct ata agc cct atg ctg att gga cat gaa gca aat ttg gat tca agc      576
Ser Ile Ser Pro Met Leu Ile Gly His Glu Ala Asn Leu Asp Ser Ser
            180                 185                 190 aca ctc caa tca gag aat ctt tgc agc ttt gga ccc ccg ctg cca tct      624
Thr Leu Gln Ser Glu Asn Leu Cys Ser Phe Gly Pro Pro Leu Pro Ser
        195                 200                 205 ctg ttg gca tgc aac tct acc cag ctt aat tct tat gca gaa aca tca      672
Leu Leu Ala Cys Asn Ser Thr Gln Leu Asn Ser Tyr Ala Glu Thr Ser
    210                 215                 220 ctc act tct tca ttt tca ctg caa cag gac cac ctc tct agt gtt gtt      720
Leu Thr Ser Ser Phe Ser Leu Gln Gln Asp His Leu Ser Ser Val Val
225                 230                 235                 240 tct cag aat gat ggg atc atc tta tgg gac atg gat gat caa gaa cag      768
Ser Gln Asn Asp Gly Ile Ile Leu Trp Asp Met Asp Asp Gln Glu Gln
                245                 250                 255 agc ctt ctt gat cag tat ggt ttc agc aac aga tac tct ttt              810
Ser Leu Leu Asp Gln Tyr Gly Phe Ser Asn Arg Tyr Ser Phe
            260                 265                 270

<210> SEQ ID NO 2
<211> LENGTH: 270
<212> TYPE: PRT
<213> ORGANISM: Vitis vinifera

<400> SEQUENCE: 2

Met Ala Ala Phe Ser Gln Gln Ser His His Leu His Pro His Lys Asn
1               5                   10                  15

Leu Arg Leu Asp Ser Thr Ile Val Pro Ser Met Ser Ala Val Phe Asp
            20                  25                  30

Asp Glu Lys Lys Pro Thr Thr Ser Ile Ser Cys Phe Ser Asp Asp Pro
        35                  40                  45

Val Lys Lys Ile Thr His Cys Ser Ser Met Gly Ala Glu Leu Gly Ala
    50                  55                  60

Pro Gly Met Ala Arg Lys Arg Lys Lys Ala Asp Phe Glu Glu Glu Arg
65                  70                  75                  80

Asp Val Glu Glu Lys Lys Gly Lys Ala Glu Lys Lys Arg Lys Lys Lys
                85                  90                  95

Val Val Lys Glu Val Pro Ser Gly Phe Val His Val Arg Ala Arg Arg
            100                 105                 110
```

Gly Glu Ala Thr Asp Ser His Ser Leu Ala Glu Arg Ala Arg Glu
            115                 120                 125

Lys Ile Ser Glu Arg Met Lys Leu Leu Gln Ser Leu Val Pro Gly Cys
    130                 135                 140

Asp Lys Leu Ile Gly Lys Thr Leu Val Leu Asp Glu Ile Ile Asn Tyr
145                 150                 155                 160

Val Lys Ser Leu Gln Asn Gln Val Glu Phe Leu Val Gly Lys Leu Ala
                165                 170                 175

Ser Ile Ser Pro Met Leu Ile Gly His Glu Ala Asn Leu Asp Ser Ser
            180                 185                 190

Thr Leu Gln Ser Glu Asn Leu Cys Ser Phe Gly Pro Pro Leu Pro Ser
        195                 200                 205

Leu Leu Ala Cys Asn Ser Thr Gln Leu Asn Ser Tyr Ala Glu Thr Ser
210                 215                 220

Leu Thr Ser Ser Phe Ser Leu Gln Gln Asp His Leu Ser Ser Val Val
225                 230                 235                 240

Ser Gln Asn Asp Gly Ile Ile Leu Trp Asp Met Asp Asp Gln Glu Gln
                245                 250                 255

Ser Leu Leu Asp Gln Tyr Gly Phe Ser Asn Arg Tyr Ser Phe
            260                 265                 270

<210> SEQ ID NO 3
<211> LENGTH: 810
<212> TYPE: DNA
<213> ORGANISM: Vitis vinifera

<400> SEQUENCE: 3
atggcagcct tttctcagca gtctcaccac cttcaccctc acaaaaatct taggcttgac      60
tctaccattg tgccatctat gtctgcagtt tttgatgatg agaagaaacc taccacctct    120
atctcttgtt tttctgatga tcctgtgaag aagatcactc attgttcatc tatgggggct    180
gagcttgggg ctccagggat ggctaggaag agaaagaagg ctgattttga ggaagagagg    240
gacgtggagg agaagaaggg taaagctgag aagaagagga agaagaagt ggtgaaagag    300 gtcccaagtg ggtttgttca gtgagagca aggaggggtg aagcaacaga cagtcactct    360
cttgctgaaa gggcaagaag agagaaaatc agtgaaagaa tgaaacttt gcaatcactt    420 gttcctggtt gtgacaaact tattggaaag actcttgttc ttgatgagat aatcaattat    480
gtcaagtctc ttcagaatca agttgagttc cttgtgggaa aacttgcttc tatatctcct    540
atgcttattg gacatgaagc aaatttggat tcatctacac ttcaatcaga gaatctttgc    600
tcttttggac ctccgcttcc atctcttttg gcatgcaact ctacccagct taattcttat    660
gcagaaacat cacttacttc ttcattttca cttcaacagg accacctttc tagtgttgtt    720
tctcagaatg atgggatcat cctttgggac atggatgatc aagaacagtc tcttcttgat    780
cagtatggtt tctctaacag atactctttt                                     810

<210> SEQ ID NO 4
<211> LENGTH: 810
<212> TYPE: DNA
<213> ORGANISM: Vitis vinifera

<400> SEQUENCE: 4
atggcvgcct tytctcarca rtctcaycay ctccayccwc ayaaraayct gcgyctggay      60
agcacsatyg tbccgagcat gagcgcvgtb ttygaygayg araaraarcc gacsacsagc    120

```
atyagctgyt tyagcgayga yccggtbaar aaratyac

```
gcvagcctgc tgctgacsga rgaycaraar gcvagcctga tyccgcargt bcargayggy      540
ggyagcttyg argaygtbgg yaarcayccg gcvcgyctgg aycayagctg yacsttytra      600

<210> SEQ ID NO 7
<211> LENGTH: 933
<212> TYPE: DNA
<213> ORGANISM: Theobroma cacao

<400> SEQUENCE: 7
atgagcgcrt tyccaaayca rcayttgccw agcgtsatya ayagcttygt bgarccgaay       60
acsctggayt gyatgagcgg yttyctgcgy gargaragca gcgcvacsaa racstgytty      120
agcagcaayt tyccggaygc rtgyttycar garatyatya gcggycarta ygcvcaraay      180
caygtbgcva csacsctgaa ygargtbaay ctggaygtbc cgttyacstt yccggtbaty      240
ccgttygcva tygcvaayca rgaratygay agcacsacsa tyccgatgct gctggarctg      300
garcarcgyg gygaygayca ycaratyacs ggygargtba gcgcvagcga raayaarcgy      360
aaraargtbg aracsaargt bgarcgygar aaraarcgyg araaraarca yaaraayaty      420
cgyggyctgc arcargcvaa rgaragccgy ctgaarccgg ayatyaaraa yaaraaraar      480
gtbccggara argtbgarac sgayaaytay gcvcaygtbc gygcvcgycg yggygargcv      540
acsgayaarc ayagcctggc vgarcgygtb cgycgygara aratyagcgt bcgyatgaar      600
ctgctgcara gcctggtbcc gggytgygay aarctgacsg gyaaracsca ratgctggay      660
garatyatyc gytaygtbca rtgyctgcar caycargtbg arttyatyag cacsgargcv      720
gargarttya gcagcctgga raargcvtgg ccgctgagct tygtbgarag cagcagcacs      780
ggycarttya argcvttyac sgcvgcvacs ccggcvccga csagcagcct gctgcaycar      840
acsgaygcvc arcarcgyct gaayatyacs acscgygaya argcvatytg ytayggyaar      900
cgycayatyc gyacsagcag cagcctggcv tra                                    933

<210> SEQ ID NO 8
<211> LENGTH: 1029
<212> TYPE: DNA
<213> ORGANISM: Ananas comosus

<400> SEQUENCE: 8
atggarttrt tyagcaatca rcaccaccar gcgagcctgc taagtccgag caayctgccg       60
aayagcttya tggaraaraa yttyccgccg carcarctgg gygaratgag caaygaracs      120
agctaytgyt tyccgtaytg ytayctgagc gargcvatyc cggarttyag caayaayagc      180
gayagcacsg cvcgygcvta ygaragcagc agcagcctgg ayacsgtbcg yaaygcvagc      240
agcgcvggya cscaratgag ccayagcgcv gtbatyacsg ayccgggyag cccgagcggy      300
aarcgycgya araaycgyga yagcacsagc ctgtgyctgg cvccgctgag caaygaygcv      360
atggaragca aracsaaraa rcaraarcgy ccgaayggyg gyctgaaraa rgtbgargar      420
aaraarccga arggygayga ratyaarcay aargargtbt gyggygarcc gcaygarggy      480
tayatycayg tbcgygcvcg ycgyggycar gcvacsgaya gccayagcct ggcvgarcgy      540
gtbcgycgyg araaratyaa yaarcgyatg aaratgctgc aragcctggt bccgggytgy      600
gayggygtba gcggyaargc vctgatgctg gaygaratya tyaaytaygt bcaragcctg      660
caraaycarg tbgarttyct gagcatgaar ctggcvagca tgaayccgat gttygaygar      720
ttyggygtbg ayttygartg yctgatgaay cayccggarg tbgcvcgyac saargcvaar      780
```

-continued

```
tgycarcaya csctgctgct gatytggccg atyagcctgg gyttygayat ygayctgacs      840
ctgtayagca tgccgcayga rcargtbccg acsgtbgayc aracsaayca yagccargcv      900
acsccgagcg argcvacsac sgtbaaytay caratggtbg ayaayagcac sccgatyctg      960
carcayggyc arggyccgac stayttyccg cargargcva ayagcacscg ycayaargay     1020 ggyacstra                                                             1029

<210> SEQ ID NO 9
<211> LENGTH: 1101
<212> TYPE: DNA
<213> ORGANISM: Fragaria vesca

<400> SEQUENCE: 9
atgggygarg cdgtwtaygg yatyggcaga gtwaaagcaa cbctgaarct gagcagcccg       60
ctgctgagca csccgctgat yagcagccgy atgatggtbc gycgyaargc vgcvagcacs      120
atgcgyatya tgctgccgct ggcvgcvggy acsccgaaya gcacsaayac saayaayctg      180
cayttyagcc aragccayta yccgagcgar ccgctggtbg arcaratgaa yatyccgggy      240
gaycaragcg cvcgygtbgc vgaragcagc agctgyatyg aycaragcag cgcvaaraty      300
gcvacsttya gcgayaayga rccgagcgtb acsaaraarc aragcccgga ragcagcagc      360
gtbgtbgaya arctggarac sggygarcar gtbacscara argtbacsac sccgatygar      420
cgyaarcgyc gyacscgyaa ytgyagcagc ccgagcagcg cvcaragcaa rgtbaaraar      480
caraaraarg cvgargarga raaraaragc aargcvgara araargarca raaraargcv      540
gtbcargarg tbgarccgcc gacsggytay atycaygtbc gygcvcgycg yggycargcv      600
acsgayagcc ayagcctggc vgarcgygtb cgycgygara aratyagcga rcgyatgaar      660
atgctgcarc gyctggtbcc gggytgygay aargtbacsg gycgygcvgt batgctggay      720
garatyatya aytaygtbca ragcctgcar aaycargtbg arttyctgag catgaarctg      780
gcvagcgtba ayccgatgtt ytaygartty ggyccggayc tgggygayct gatggtbaar      840
cargargcva gcccgttyag cacsggyccg cartgyagcc cgacscarcc gacsaaytty      900
gcvgayacsa gcacsacsgc vgcvacsacs acsttyacsg cvgcvacsaa yaaytayccg      960
ttyctggaya gcctgctgca ycaragcccg cgyccgacsg cvttycayca rgayaaygar     1020
agcctgctgt gggayggyga rgaycarcgy caragcttyc tgaayccgag cggyttyaay     1080
aayctgtgya gcttyaaytr a                                               1101
```